United States Patent
Yang et al.

(10) Patent No.: US 9,944,665 B2
(45) Date of Patent: Apr. 17, 2018

(54) BRIDGED BIS(INDENYL) TRANSITIONAL METAL COMPLEXES, PRODUCTION, AND USE THEREOF

(71) Applicant: ExxonMobil Chemical Patents Inc., Baytown, TX (US)

(72) Inventors: Jian Yang, Houston, TX (US); Matthew W. Holtcamp, Huffman, TX (US); Xiongdong Lian, Shanghai (CN); Gregory S. Day, Pasadena, TX (US)

(73) Assignee: ExxonMobil Chemical Patents Inc., Baytown, TX (US)

(*) Notice: Subject to any disclaimer, the term of this patent is extended or adjusted under 35 U.S.C. 154(b) by 0 days.

(21) Appl. No.: 14/572,195

(22) Filed: Dec. 16, 2014

(65) Prior Publication Data

US 2015/0183893 A1   Jul. 2, 2015

Related U.S. Application Data

(60) Provisional application No. 61/918,328, filed on Dec. 19, 2013.

(51) Int. Cl.
*C07F 17/00* (2006.01)
*C08F 4/6592* (2006.01)
(Continued)

(52) U.S. Cl.
CPC ............ *C07F 7/0818* (2013.01); *C07F 17/00* (2013.01); *C08F 4/65927* (2013.01);
(Continued)

(58) Field of Classification Search
CPC ....... C07F 17/00; C08F 4/65927; C08F 10/06
See application file for complete search history.

(56) References Cited

U.S. PATENT DOCUMENTS 6,306,658 B1   10/2001   Turner et al.
6,376,408 B1 *  4/2002   Burkhardt ............... C07F 17/00
                                                    502/103
(Continued)

FOREIGN PATENT DOCUMENTS

EP          2 360 163 A1    8/2011
KR    10-2006-0028603       3/2006
(Continued)

OTHER PUBLICATIONS

Boussie, Thomas R. et al., "*A Fully Integrated High-Throughput Screening Methodology for the Discovery of New Polyolefin Catalysts: Discovery of a New Class of High Temperature Single-Site Group (IV) Copolymerization Catalysts*," JACS, 2003, 125, pp. 4306-4317.
(Continued)

*Primary Examiner* — Caixia Lu

(57) ABSTRACT

The invention relates to a novel group bridged metallocene transition metal complexes, wherein the complex includes at least one indenyl ligand substituted at the 4-position with a phenyl group, the 4-phenyl group being preferably substituted at the 3', 4', and 5' positions with particular combinations of substituents, particularly wherein the 4'-substituent is a group of the formula $(XR'_n)^-$, wherein X is a Group 14-17 heteroatom having an atomic weight of 13 to 79 and R' is one of a hydrogen atom, halogen atom, a $C_1$-$C_{10}$ alkyl group, or a $C_6$-$C_{10}$ aryl group and n is 0, 1, 2, or 3. Catalyst systems including the transition metal complex, polymerization processes using the transition metal complex, and polymers made using the transition metal complex are also described.

51 Claims, 3 Drawing Sheets

(51) Int. Cl.
*C08F 10/06* (2006.01)
*C07F 7/08* (2006.01)
*C08F 210/16* (2006.01)
*C08F 4/659* (2006.01)

(52) U.S. Cl.
CPC .......... *C08F 10/06* (2013.01); *C08F 4/65912* (2013.01); *C08F 4/65916* (2013.01); *C08F 210/16* (2013.01)

(56) References Cited

U.S. PATENT DOCUMENTS

| | | |
|---|---|---|
| 6,455,316 B1 | 9/2002 | Turner et al. |
| 6,489,168 B1 | 12/2002 | Wang et al. |
| 7,223,878 B2 * | 5/2007 | Schulte .................. C07F 17/00 502/103 |
| 2011/0230622 A1 | 9/2011 | Nakano et al. |
| 2015/0025205 A1 | 1/2015 | Jian et al. |
| 2015/0025206 A1 | 1/2015 | Yang et al. |
| 2015/0025208 A1 | 1/2015 | Yang et al. |
| 2015/0119537 A1 | 4/2015 | Holtcamp et al. |
| 2015/0284418 A1 | 10/2015 | Lynch et al. |

FOREIGN PATENT DOCUMENTS

| | | |
|---|---|---|
| KR | 10-2013-0125311 | 11/2013 |
| WO | WO 98/403331 | 9/1998 |
| WO | WO 00/09255 | 2/2000 |
| WO | WO 02/002575 | 1/2002 |
| WO | WO 02/002576 | 1/2002 |
| WO | WO 02/102575 | 12/2002 |

OTHER PUBLICATIONS

Hans H. Brintzinger et al., Development of ansa-Metallocene catalysts for Isotactic Olefin polymerization, Adv. Polymer Science, 2013, vol. 258, pp. 29-42.

Leino, Reko et al., "*Homogeneous R-Olefin Polymerizations over Racemic Ethylene-Bridged ansa-Bis(2-(tert-butyldimethylsiloxy)-1-indenyl) and ansa-Bis(2-(tert-butyldimethylsiloxy)-4,5,6,7-tetrahydro-1-indenyl) Metallocene Dichlorides*," Macromolecules, 1997, vol. 30(12), pp. 3477-3483.

Nifant'ev, Ilya E. et al., "*5-Methoxy-Substituted Zirconium Bis-indenyl ansa-Complexes: Synthesis, Structure, and Catalytic Activity in the Polymerization and Copolymerization of Alkenes*," Organometallics, 2012, vol. 31(14), pp. 4962-4970.

\* cited by examiner

BRIDGED BIS(INDENYL) TRANSITIONAL METAL COMPLEXES, PRODUCTION, AND USE THEREOF

PRIORITY

This invention claims priority to and the benefit of U.S. Ser. No. 61/918,328, filed Dec. 19, 2013.

FIELD OF THE INVENTION

This invention relates to novel catalyst compounds comprising bridged bis(indenyl) transition metal complexes and processes for use in making such complexes. The transition metal complexes may be used as catalysts for alkene polymerization processes.

BACKGROUND OF THE INVENTION

Olefin polymerization catalysts are of great use in industry. Hence there is interest in finding new catalyst systems that increase the commercial usefulness of the catalyst and allow the production of polymers having improved properties.

Catalysts for olefin polymerization are often based on transition metal compounds, e.g., metallocenes, as catalyst precursors, which are activated either with the help of alumoxane, or with an activator containing a non-coordinating anion.

WO2002/002576 discloses metallocene compositions and their use in the preparation of catalyst systems for olefin polymerization, particularly propylene polymerization. The bridged bis(2-$R^3$-4-phenyl-indenyl)metallocenes described therein include those wherein at least one of the phenyl rings is substituted at the 3' and 5' positions by butyl groups which may be the same or different, e.g., tert-butyl.

Other references of interest include: WO98/403331; Organometallics 2012, 31, pp. 4962-4970; U.S. Pat. No. 6,489,168; US 2011/0230622; WO02/102575; and EP 2 360 163A1.

There is still a need in the art for new and improved catalyst systems for the polymerization of olefins, in order to achieve specific polymer properties, such as high melting point, high molecular weights, to increase conversion or comonomer incorporation, or to alter comonomer distribution without deteriorating the resulting polymer's properties. It is therefore an object of the present invention to provide novel catalyst compounds, catalysts systems comprising such compounds, and processes for the polymerization of olefins using such compounds and systems.

SUMMARY OF THE INVENTION

This invention relates to a novel bridged transition metal complexes represented by the formula (I):

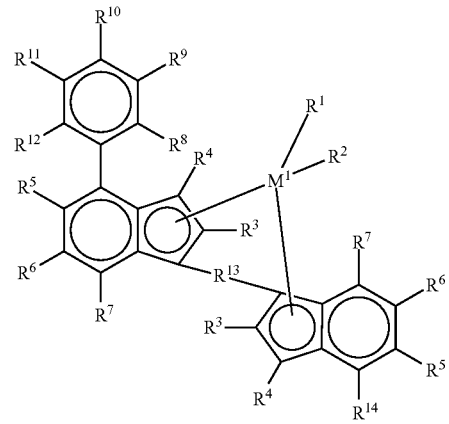

wherein $M^1$ is selected from the group consisting of titanium, zirconium, hafnium, vanadium, niobium, tantalum, chromium, molybdenum and tungsten;

$R^1$ and $R^2$ may be identical or different, and are each a hydrogen atom, a $C_1$-$C_{10}$ alkyl group, a $C_1$-$C_{10}$ alkoxy group, a $C_6$-$C_{10}$ aryl group, a $C_6$-$C_{10}$ aryloxy group, a $C_2$-$C_{10}$ alkenyl group, a $C_2$-$C_{40}$ alkenyl group, a $C_7$-$C_{40}$ arylalkyl group, a $C_7$-$C_{40}$ alkylaryl group, a $C_8$-$C_{40}$ (preferably $C_8$-$C_{30}$)arylalkenyl group, an OH group or a halogen atom, or a conjugated diene which is optionally substituted with one or more hydrocarbyl, tri(hydrocarbyl)silyl groups or tri(hydrocarbyl)silylhydrocarbyl groups, said diene having up to 30 atoms not counting hydrogen;

$R^3$ to $R^7$ may be identical or different and are each a hydrogen atom, a halogen atom, a $C_1$-$C_{10}$ alkyl group which may be halogenated, a $C_6$-$C_{10}$ aryl group which may be halogenated, a $C_2$-$C_{10}$ alkenyl group, a $C_7$-$C_{40}$ arylalkyl group, a $C_7$-$C_{40}$ alkylaryl group, a $C_8$-$C_{40}$ arylalkenyl group, a-NR'$_2$, —SR', —OR, —OSiR'$_3$ or —PR'$_2$ radical, wherein R' is one of a hydrogen atom, halogen atom, a $C_1$-$C_{10}$ alkyl group, or a $C_6$-$C_{10}$ aryl group or two or more adjacent radicals $R^5$ to $R^7$ together with the atoms of the indenyl group connecting them form one or more rings;

$R^{13}$ is —B($R^{15}$)—, —Al($R^{15}$)—, —Ge—, —Sn—, —O—, —S—, —SO—, —SO2-, —N($R^{15}$)—, —CO—, —P($R^{15}$)—, or —P(O)($R^{15}$)—, an amidoborane radical or meets one of the following:

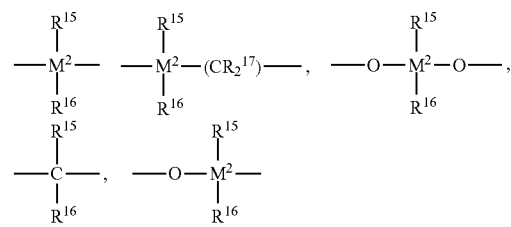

wherein: $R^{15}$, $R^{16}$, $R^{17}$ are identical or different and are a hydrogen atom, a halogen atom, a $C_1$-$C_{20}$ alkyl group, a $C_1$-$C_{20}$ fluoroalkyl or silaalkyl group, a $C_6$-$C_{30}$ aryl group, a $C_6$-$C_{30}$ fluoroaryl group, a $C_1$-$C_{20}$ alkoxy group, a $C_2$-$C_{20}$ alkenyl group, a $C_7$-$C_{40}$ arylalkyl group, a $C_8$-$C_{40}$ arylalkenyl group, a $C_7$-$C_{40}$ alkylaryl group, or one $R^{15}$ and one $R^{16}$, together with the atoms in $R^{13}$ connecting them, form one or more rings; $M^2$ is one or more carbons, silicon, germanium or tin;

$R^8$ and $R^{12}$ may be identical or different and are each a hydrogen atom, a halogen atom, a $C_1$-$C_{10}$ alkyl group which may be halogenated, a $C_6$-$C_{10}$ aryl group which may be halogenated, a $C_2$-$C_{10}$ alkenyl group, a $C_7$-$C_{40}$ arylalkyl group, a $C_7$-$C_{40}$ alkylaryl group, a $C_8$-$C_{40}$ (preferably $C_8$-$C_{30}$), arylalkenyl group, a-$NR'_2$, —$SR'$, —$OR$, —$OSiR'_3$ or —$PR'_2$ radical, wherein R' is as defined above;

wherein $R^9$ and $R^{11}$ are identical or different and selected from $C_2$-$C_{20}$ alkyl group which may be halogenated, a $C_6$-$C_{10}$ aryl group which may be halogenated, a $C_2$-$C_{10}$ alkenyl group, a $C_7$-$C_{20}$ arylalkyl group, a $C_7$-$C_{20}$ alkylaryl group, a $C_8$-$C_{20}$ arylalkenyl group; and wherein $R^{10}$ is $(XR'_n)^-$, wherein X is a Group 14, 15, 16 or 17 heteroatom having an atomic weight of 13 to 79 and R' is one of a hydrogen atom, halogen atom, a $C_1$-$C_{10}$ alkyl group, or a $C_6$-$C_{10}$ aryl group and n is 0, 1, 2 or 3; and $R^{14}$ is a hydrogen atom, a halogen atom, a $C_3$-$C_{10}$ alkyl group which may be halogenated, a $C_6$-$C_{10}$ aryl group which may be halogenated, a $C_2$-$C_{10}$ alkenyl group, a $C_7$-$C_{40}$ arylalkyl group, a $C_7$-$C_{40}$ alkylaryl group, a $C_8$-$C_{40}$ arylalkenyl group, a —$NR'_2$, —$SR'$, —$OR$, —$OSiR'_3$ or —$PR'_2$ radical, wherein R' is as defined above, preferably a substituted phenyl group.

In another aspect, embodiments of the invention provide a bridged bis(4-phenyl-indenyl) transition metal complex wherein: at least one of the 4-phenyl rings is substituted at the 3' and 5' positions by radicals which may be identical or different and selected from $C_2$-$C_{20}$ alkyl group which may be halogenated, a $C_6$-$C_{10}$ aryl group which may be halogenated, a $C_2$-$C_{10}$ alkenyl group, a $C_7$-$C_{20}$ arylalkyl group, a $C_7$-$C_{20}$ alkylaryl group, a $C_8$-$C_{20}$ arylalkenyl group, wherein at least one of the phenyl rings substituted at the 3' and 5' positions is also substituted at the 4' position with a group of the formula $(XR'_n)^-$, wherein X is a Group 14, 15 16, or 17 heteroatom having an atomic weight of 13 to 79 and R' is one of a hydrogen atom, halogen atom, a $C_1$-$C_{10}$ alkyl group, or a $C_6$-$C_{10}$ aryl group and n is 0, 1, 2, or 3; preferably at least one of the phenyl groups is substituted at the 4' position with one or more of —$NR'_2$, —$SR'$, —$OR'$, —$OSiR'_3$, —$SiR'_3$, or —$PR'_2$; and optionally, wherein one or more of the remaining positions on the phenyl and/or indenyl ring(s) of the transition metal complex are substituted, such as the 2 position.

More particularly, embodiments of the invention provide a transition metal complex represented by the formula (II):

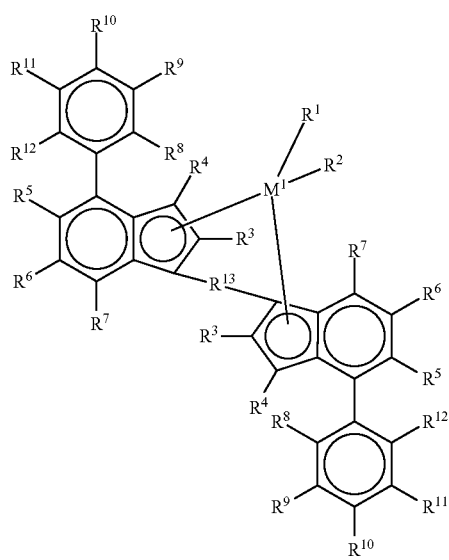

(II)

wherein $M^1$ is Zr, Hf or Ti; $R^1$ and $R^2$ are Cl; each $R^3$ is methyl; each $R^4$, $R^5$, $R^6$, and $R^7$ is a hydrogen atom; each $R^8$ and $R^{12}$ are each a hydrogen atom; $R^{13}$ is —$Si(CH_3)_2$—; each $R^9$ and $R^{11}$ is a tert-butyl group; and each $R^{10}$ is a methoxy group.

In yet another aspect, embodiments of the invention provide a catalyst system comprising an activator and a transition metal complex of described herein.

In still another aspect, embodiments of the invention provide a polymerization process comprising a) contacting one or more alkene monomers with a catalyst system comprising: i) an activator and ii) a transition metal complex described herein.

This invention further relates to polymer compositions produced by the methods described herein.

DETAILED DESCRIPTION

Figure 1:
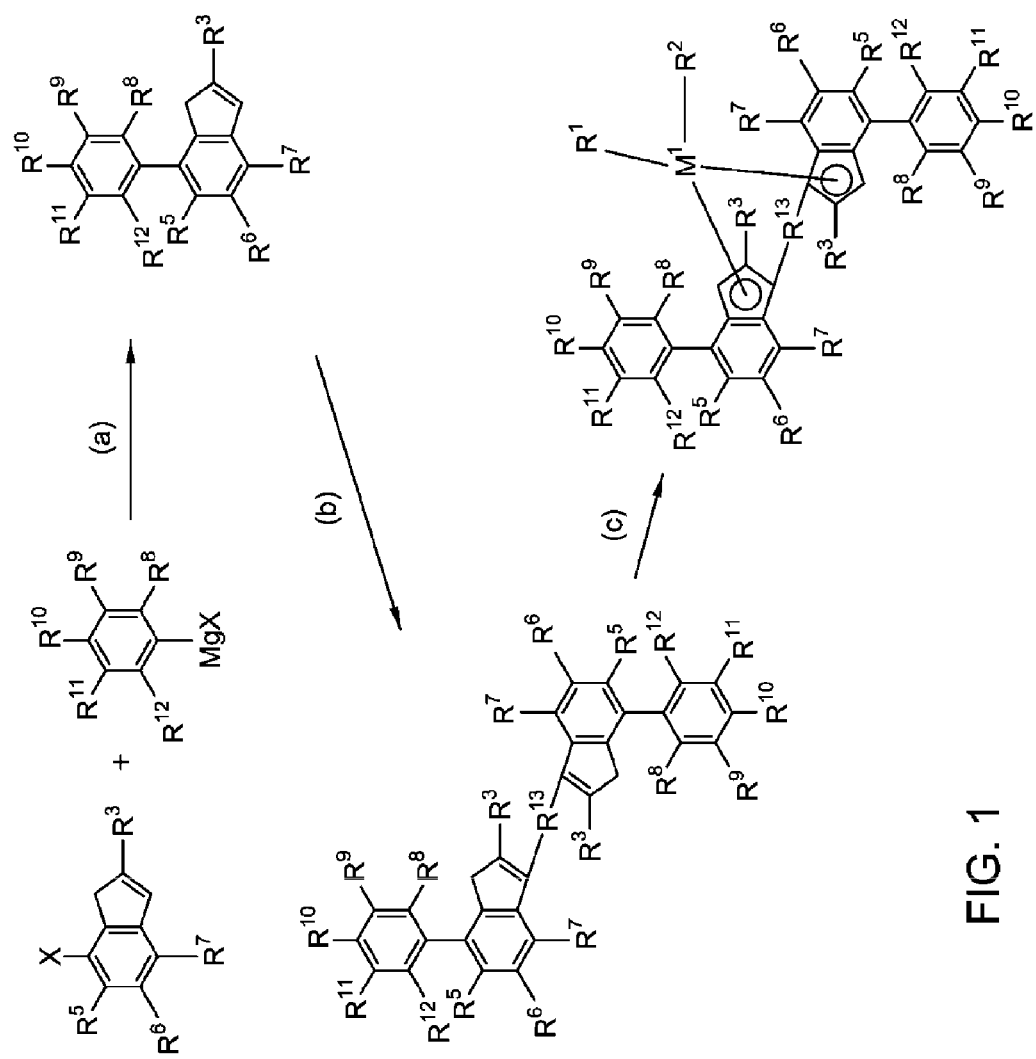
FIG. 1 illustrates a general reaction pathway suitable for preparing transition metal complexes described herein.

The specification describes transition metal complexes. The term complex is used to describe molecules in which an ancillary ligand is coordinated to a central transition metal atom. The ligand is bulky and stably bonded to the transition metal so as to maintain its influence during use of the catalyst, such as polymerization. The ligand may be coordinated to the transition metal by covalent bond and/or electron donation coordination or intermediate bonds. The transition metal complexes are generally subjected to activation to perform their polymerization or oligomerization function using an activator which is believed to create a cation as a result of the removal of an anionic group, often referred to as a leaving group, from the transition metal.

For the purposes of this invention and the claims thereto, the new numbering scheme for the Periodic Table Groups is used as described in Chemical and Engineering News, 63(5), pg. 27 (1985). Therefore, a "Group 4 metal" is an element from Group 4 of the Periodic Table, e.g., Hf, Ti, or Zr.

The following abbreviations are used through this specification: dme is 1,2-dimethoxyethane, Me is methyl, Ph is phenyl, Et is ethyl, Pr is propyl, iPr is isopropyl, n-Pr is normal propyl, Bu is butyl, cPR is cyclopropyl, iBu is isobutyl, tBu is tertiary butyl, p-tBu is para-tertiary butyl, nBu is normal butyl, sBu is sec-butyl, TMS is trimethylsilyl, TIBAL is triisobutylaluminum, TNOAL is tri(n-octyl)aluminum, MAO is methylalumoxane, p-Me is para-methyl, Ph is phenyl, Bn is benzyl (i.e., $CH_2Ph$), THF (also referred to as thf) is tetrahydrofuran, RT is room temperature (and is 23° C. unless otherwise indicated), tol is toluene, EtOAc is ethyl acetate, and Cy is cyclohexyl.

For purposes of this invention and claims thereto, the term "substituted" means that a hydrogen group has been replaced with a heteroatom, or a heteroatom containing group or where a cyclic hydrocarbyl has a hydrogen replaced by a non-hydrogen atom. For example, methoxycyclopentadiene is a cyclopentadiene substituted with a methoxy group and methyl-phenyl is a phenyl group substituted with a methyl group.

The terms "hydrocarbyl radical," "hydrocarbyl," "hydrocarbyl group," "alkyl radical," and "alkyl" are used interchangeably throughout this document. Likewise, the terms "group", "radical", and "substituent" are also used interchangeably in this disclosure. For purposes of this disclosure, "hydrocarbyl radical" is defined to be $C_1$-$C_{100}$ radicals, that may be linear, branched, or cyclic, and when cyclic, aromatic or non-aromatic. Examples of such radicals include, but are not limited to, methyl, ethyl, n-propyl, isopropyl, n-butyl, isobutyl, sec-butyl, tert-butyl, pentyl, iso-amyl, hexyl, octyl cyclopropyl, cyclobutyl, cyclopentyl, cyclohexyl, cyclooctyl, and the like including their substituted analogues. Substituted hydrocarbyl radicals are radicals in which at least one hydrogen atom of the hydrocarbyl radical has been substituted with at least one halogen (such as Br, Cl, F or I) or at least one functional group such as $NR*_2$, $OR*$, $SeR*$, $TeR*$, $PR*_2$, $AsR*_2$, $SbR*_2$, $SR*$, $BR*_2$, $SiR*_3$, $GeR*_3$, $SnR*_3$, $PbR*_3$, and the like, or where at least one heteroatom has been inserted within a hydrocarbyl ring.

The term "alkenyl" means a straight-chain, branched-chain, or cyclic hydrocarbon radical having one or more double bonds. These alkenyl radicals may be optionally substituted. Examples of suitable alkenyl radicals include, but are not limited to, ethenyl, propenyl, allyl, 1,4-butadienyl cyclopropenyl, cyclobutenyl, cyclopentenyl, cyclohexenyl, cyclooctenyl and the like including their substituted analogues.

The term "alkoxy" or "alkoxide" means an alkyl ether or aryl ether radical wherein the term alkyl is as defined above. Examples of suitable alkyl ether radicals include, but are not limited to, methoxy, ethoxy, n-propoxy, iso-propoxy, n-butoxy, iso-butoxy, sec-butoxy, tert-butoxy, phenoxyl, and the like.

The term "aryl" or "aryl group" means a six carbon aromatic ring and the substituted variants thereof, including but not limited to, phenyl, 2-methyl-phenyl, xylyl, 4-bromoxylyl. Likewise heteroaryl means an aryl group where a ring carbon atom (or two or three ring carbon atoms) has been replaced with a heteroatom, preferably N, O, or S. As used herein, the term "aromatic" also refers to pseudoaromatic heterocycles which are heterocyclic substituents that have similar properties and structures (nearly planar) to aromatic heterocyclic ligands, but are not by definition aromatic; likewise the term aromatic also refers to substituted aromatics.

Where isomers of a named alkyl, alkenyl, alkoxide, or aryl group exist (e.g., n-butyl, iso-butyl, sec-butyl, and tert-butyl) reference to one member of the group (e.g., n-butyl) shall expressly disclose the remaining isomers (e.g., iso-butyl, sec-butyl, and tert-butyl) in the family. Likewise, reference to an alkyl, alkenyl, alkoxide, or aryl group without specifying a particular isomer (e.g., butyl) expressly discloses all isomers (e.g., n-butyl, iso-butyl, sec-butyl, and tert-butyl).

The term "ring atom" means an atom that is part of a cyclic ring structure. By this definition, a benzyl group has six ring atoms and tetrahydrofuran has 5 ring atoms.

A heterocyclic ring is a ring having a heteroatom in the ring structure as opposed to a heteroatom substituted ring where a hydrogen on a ring atom is replaced with a heteroatom. For example, tetrahydrofuran is a heterocyclic ring and 4-N,N-dimethylamino-phenyl is a heteroatom substituted ring.

The term "catalyst system" is defined to mean a complex/activator pair. When "catalyst system" is used to describe such a pair before activation, it means the unactivated catalyst complex (precatalyst) together with an activator and, optionally, a co-activator. When it is used to describe such a pair after activation, it means the activated complex and the activator or other charge-balancing moiety. The transition metal compound may be neutral as in a precatalyst, or a charged species with a counter ion as in an activated catalyst system.

"Complex" as used herein, is also often referred to as catalyst precursor, precatalyst, catalyst, catalyst compound, transition metal compound, or transition metal complex. These words are used interchangeably. Activator and cocatalyst are also used interchangeably.

A scavenger is a compound that is typically added to facilitate polymerization by scavenging impurities. Some scavengers may also act as activators and may be referred to as co-activators. A co-activator, that is not a scavenger, may also be used in conjunction with an activator in order to form an active catalyst. In some embodiments a co-activator can be pre-mixed with the transition metal compound to form an alkylated transition metal compound.

Noncoordinating anion (NCA) is defined to mean an anion either that does not coordinate to the catalyst metal cation or that does coordinate to the metal cation, but only weakly. The term NCA is also defined to include multicomponent NCA-containing activators, such as N,N-dimethylanilinium tetrakis(pentafluorophenyl)borate, that contain an acidic cationic group and the non-coordinating anion. The term NCA is also defined to include neutral Lewis acids, such as tris(pentafluorophenyl)boron, that can react with a catalyst to form an activated species by abstraction of an anionic group. An NCA coordinates weakly enough that a neutral Lewis base, such as an olefinically or acetylenically unsaturated monomer can displace it from the catalyst center. Any metal or metalloid that can form a compatible, weakly coordinating complex may be used or contained in the noncoordinating anion. Suitable metals include, but are not limited to, aluminum, gold, and platinum. Suitable metalloids include, but are not limited to, boron, aluminum, phosphorus, and silicon. Activators containing non-coordinating anions can also be referred to as stoichiometric activators. A stoichiometric activator can be either neutral or ionic. The terms ionic activator and stoichiometric ionic activator can be used interchangeably. Likewise, the terms neutral stoichiometric activator and Lewis acid activator can be used interchangeably. The term non-coordinating anion activator includes neutral stoichiometric activators, ionic stoichiometric activators, ionic activators, and Lewis acid activators.

In the description herein, the metallocene catalyst may be described as a catalyst precursor, a pre-catalyst compound, metallocene catalyst compound or a transition metal compound, and these terms are used interchangeably. A polymerization catalyst system is a catalyst system that can polymerize monomers to polymer. An "anionic ligand" is a negatively charged ligand which donates one or more pairs of electrons to a metal ion. A "neutral donor ligand" is a neutrally charged ligand which donates one or more pairs of electrons to a metal ion.

A metallocene catalyst is defined as an organometallic compound with at least one π-bound cyclopentadienyl moiety (or substituted cyclopentadienyl moiety) and more frequently two π-bound cyclopentadienyl moieties or substituted cyclopentadienyl moieties.

For purposes of this invention and claims thereto in relation to metallocene catalyst compounds, the term "substituted" means that a hydrogen group has been replaced with a hydrocarbyl group, a heteroatom, or a heteroatom containing group. For example, methyl cyclopentadiene (Cp) is a Cp group substituted with a methyl group.

"Catalyst productivity" is a measure of how many grams of polymer (P) are produced using a polymerization catalyst comprising W g of catalyst (cat), over a period of time of T hours; and may be expressed by the following formula: P/(T×W) and expressed in units of gPgcat-1 hr-1. Conversion is the amount of monomer that is converted to polymer product, and is reported as mol % and is calculated based on the polymer yield and the amount of monomer fed into the reactor. Catalyst activity is a measure of how active the catalyst is and is reported as the mass of product polymer (P) produced per mole of catalyst (cat) used (kgP/molcat).

For purposes herein an "olefin," alternatively referred to as "alkene," is a linear, branched, or cyclic compound comprising carbon and hydrogen having at least one double bond. For purposes of this specification and the claims appended thereto, when a polymer or copolymer is referred to as comprising an olefin, the olefin present in such polymer or copolymer is the polymerized form of the olefin. For example, when a copolymer is said to have a "propylene" content of 35 wt % to 55 wt %, it is understood that the mer unit in the copolymer is derived from propylene in the polymerization reaction and said derived units are present at 35 wt % to 55 wt %, based upon the weight of the copolymer. A higher α-olefin is defined to be an α-olefin having 4 or more carbon atoms. For the purposes of this disclosure ethylene is considered an alpha-olefin.

For purposes herein a "polymer" has two or more of the same or different "mer" units. A "homopolymer" is a polymer having mer units that are the same. A "copolymer" is a polymer having two or more mer units that are different from each other. A "terpolymer" is a polymer having three mer units that are different from each other. "Different" in reference to mer units indicates that the mer units differ from each other by at least one atom or are different isomerically. Accordingly, the definition of copolymer, as used herein, includes terpolymers and the like. An oligomer is typically a polymer having a low molecular weight, such an Mn of less than 25,000 g/mol, or less than 2,500 g/mol, or a low number of mer units, such as 75 mer units or less or 50 mer units or less. An "ethylene polymer" or "ethylene copolymer" is a polymer or copolymer comprising at least 50 mole % ethylene derived units, a "propylene polymer" or "propylene copolymer" is a polymer or copolymer comprising at least 50 mole % propylene derived units, and so on.

As used herein, Mn is number average molecular weight, Mw is weight average molecular weight, and Mz is z average molecular weight, wt % is weight percent, and mol % is mole percent. Molecular weight distribution (MWD), also referred to as polydispersity (PDI), is defined to be Mw divided by Mn. Unless otherwise noted, all molecular weight units (e.g., Mw, Mn, Mz) are g/mol.

The term "continuous" means a system that operates without interruption or cessation. For example a continuous process to produce a polymer would be one where the reactants are continually introduced into one or more reactors and polymer product is continually withdrawn.

A solution polymerization means a polymerization process in which the polymer is dissolved in a liquid polymerization medium, such as an inert solvent or monomer(s) or their blends. A solution polymerization is typically homogeneous. A homogeneous polymerization is one where the polymer product is dissolved in the polymerization medium. Such systems are preferably not turbid as described in J. Vladimir Oliveira, C. Dariva and J. C. Pinto, Ind. Eng. Chem. Res. 29, 2000, 4627.

A bulk polymerization means a polymerization process in which the monomers and/or comonomers being polymerized are used as a solvent or diluent using little or no inert solvent as a solvent or diluent. A small fraction of inert solvent might be used as a carrier for catalyst and scavenger. A bulk polymerization system contains less than 25 wt % of inert solvent or diluent, preferably less than 10 wt %, preferably less than 1 wt %, preferably 0 wt %.

Transition Metal Complexes

In particular embodiments the invention relates to novel bridged metallocene transition metal complexes, where the complexes include at least one indenyl ligand substituted at the 4-position with a phenyl group, the phenyl group being substituted at the 3', 4', and 5' positions with particular combinations of substituents. In preferred embodiments, the 3' and 5' positions of the phenyl ring are selected to be sterically hindering (e.g., branched hydrocarbyl groups) and the 4'-substituent is selected from $(XR'_n)'$, wherein X is a Group 14, 15, 16 or 17 heteroatom having an atomic weight of 13 to 79 (preferably N, O, S, P, or Si) and R' is one of a hydrogen atom, halogen atom, a $C_1$-$C_{10}$ alkyl group (such as methyl, ethyl, propyl, butyl, pentyl, hexyl, octyl, nonyl, decyl or an isomer thereof), or a $C_6$-$C_{10}$ aryl group and n is 0, 1, 2, or 3; preferably $(XR'_n)^-$ is —$NR'_2$, —$SR'$, —$OR'$, —$OSiR'_3$, —$SiR'_3$, or —$PR'_2$, preferably $(XR'_n)'$ is —$NR'_2$, —$SR'$, —$OR'$, —$OSiR'_3$, or —$PR'_2$, preferably $(XR'_n)^-$ is —$SR'$, —$OR'$, or —$OSiR'_3$, preferably $(XR'_n)^-$ is —$NR'_2$ or —$PR'_2$, or preferably $(XR'_n)^-$ is —$OR'$.

In a preferred embodiment this invention relates to a catalyst compound, and catalyst systems comprising such compounds, represented by the formula (I):

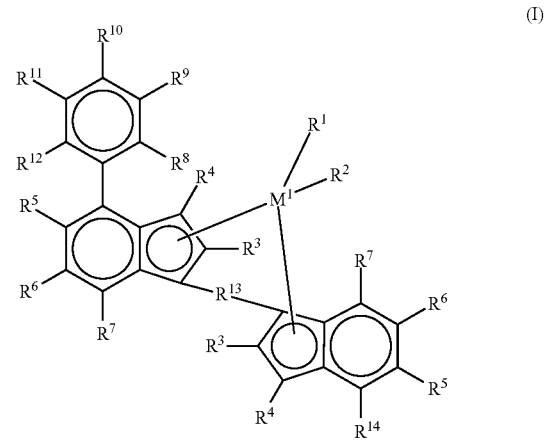

wherein $M^1$ is selected from the group consisting of titanium, zirconium, hafnium, vanadium, niobium, tantalum, chromium, molybdenum and tungsten (preferably titanium, zirconium, and hafnium);

$R^1$ and $R^2$ may be identical or different, and are each a hydrogen atom, a $C_1$-$C_{10}$ alkyl group (such as methyl, ethyl, propyl, butyl, pentyl, hexyl, octyl and isomers thereof), a $C_1$-$C_{10}$ alkoxy group, a $C_6$-$C_{10}$ aryl group, a $C_6$-$C_{10}$ aryloxy group, a $C_2$-$C_{10}$ alkenyl group, a $C_2$-$C_{40}$ alkenyl group, a $C_7$-$C_{40}$ arylalkyl group, a $C_7$-$C_{40}$ alkylaryl group, a $C_8$-$C_{40}$ arylalkenyl group, an OH group, a halogen atom, a conjugated diene which is optionally substituted with one or more hydrocarbyl, tri(hydrocarbyl)silyl groups or tri(hydrocarbyl)silylhydrocarbyl groups, said diene having up to 30 atoms not counting hydrogen, a hydride, an amides, a sulfide, a phosphides, an amine, a phosphines, an ethers, or a combination thereof;

each $R^3$ may be identical or different and are each a hydrogen atom, a halogen atom, a $C_1$-$C_{10}$ alkyl group (preferably $C_3$ to $C_{10}$ alkyl, preferably $C_4$ to $C_8$ alkyl) which may be halogenated, a $C_6$-$C_{10}$ aryl group which may be halogenated, a $C_2$-$C_{10}$ alkenyl group, a $C_7$-$C_{40}$ arylalkyl group, a $C_7$-$C_{40}$ alkylaryl group, a $C_8$-$C_{40}$, (preferably $C_8$-$C_{30}$)arylalkenyl group, a-$NR'_2$, —$SR'$, —$OR$, —$OSiR'_3$ or —$PR'_2$ radical, wherein $R'$ is one of a hydrogen atom, halogen atom, a $C_1$-$C_{10}$ alkyl group, or a $C_6$-$C_{10}$ aryl group or two or more adjacent radicals $R^5$ to $R^7$ together with the atoms of the indenyl group connecting them form one or more rings (preferably one or both $R^3$ are not hydrogen, preferably one or both $R^3$ are methyl, ethyl, propyl, butyl, pentyl, hexyl, heptyl, octyl, nonyl, decyl, undecyl, dodecyl, (usefully, an isomer thereof, such as cyclopropyl) or the like);

$R^4$, $R^5$, $R^6$, and $R^7$ may be identical or different and are each a hydrogen atom, a halogen atom, a $C_1$-$C_{10}$ alkyl group (preferably methyl, ethyl, propyl, butyl, pentyl, hexyl, heptyl, octyl, nonyl, decyl, undecyl, dodecyl or the like) which may be halogenated, a $C_6$-$C_{10}$ aryl group which may be halogenated, a $C_2$-$C_{10}$ alkenyl group, a $C_7$-$C_{40}$ arylalkyl group, a $C_7$-$C_{40}$ alkylaryl group, a $C_8$-$C_{40}$, arylalkenyl group, a-$NR'_2$, —$SR'$, —$OR$, —$OSiR'_3$ or —$PR'_2$ radical, wherein $R'$ is one of a hydrogen atom, halogen atom, a $C_1$-$C_{10}$ alkyl group, or a $C_6$-$C_{10}$ aryl group or two or more adjacent radicals $R^5$ to $R^7$ together with the atoms of the indenyl group connecting them forming one or more rings;

$R^{13}$ is —$B(R^{15})$—, —$Al(R^{15})$—, —$Ge$—, —$Sn$—, —$O$—, —$S$—, —$SO$—, —$SO2$-, —$N(R^{15})$—, —$CO$—, —$P(R^{15})$—, or —$P(O)(R^{15})$—, an amidoborane radical or is represented by one of the following formulae:

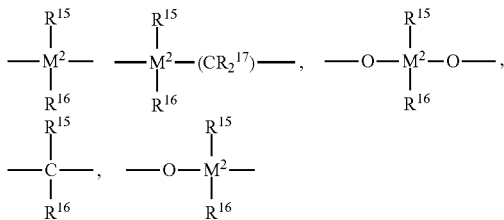

wherein: $R^{15}$, $R^{16}$, $R^{17}$ are identical or different and are a hydrogen atom, a halogen atom, a $C_1$-$C_{20}$ alkyl group, a $C_1$-$C_{20}$ fluoroalkyl or silaalkyl group, a $C_6$-$C_{30}$ aryl group, a $C_6$-$C_{30}$ fluoroaryl group, a $C_1$-$C_{20}$ alkoxy group, a $C_2$-$C_{20}$ alkenyl group, a $C_7$-$C_{40}$ arylalkyl group, a $C_8$-$C_{40}$ arylalkenyl group, a $C_7$-$C_{40}$ alkylaryl group, or one $R^{15}$ and one $R^{16}$, together with the atoms in $R^{13}$ connecting them, form one or more rings; $M^2$ is one or more of carbon, silicon, germanium or tin;

$R^8$ and $R^{12}$ may be identical or different and are each a hydrogen atom, a halogen atom, a $C_1$-$C_{10}$ alkyl group (preferably $C_2$ to $C_{10}$, preferably $C_3$ to $C_{10}$, preferably methyl, ethyl, propyl, butyl, pentyl, hexyl, heptyl, octyl, nonyl, decyl, undecyl, dodecyl or the like) which may be halogenated, a $C_6$-$C_{10}$ aryl group which may be halogenated, a $C_2$-$C_{10}$ alkenyl group, a $C_7$-$C_{40}$ arylalkyl group, a $C_7$-$C_{40}$ alkylaryl group, a $C_8$-$C_{40}$, arylalkenyl group, a-$NR'_2$, —$SR'$, —$OR$, —$OSiR'_3$ or —$PR'_z$ radical, wherein $R'$ is one of a hydrogen atom, halogen atom, a $C_1$-$C_{10}$ alkyl group, or a $C_6$-$C_{10}$ aryl group;

$R^9$ and $R^{11}$ are identical or different and selected from $C_2$-$C_{20}$ alkyl group (preferably $C_3$ to $C_{16}$, preferably $C_4$ to $C_{112}$, preferably butyl, pentyl, hexyl, heptyl, octyl, nonyl, decyl, undecyl, dodecyl and isomers thereof) which may be halogenated, a $C_6$-$C_{10}$ aryl group which may be halogenated, a $C_2$-$C_{10}$ alkenyl group, a $C_7$-$C_{20}$ arylalkyl group, a $C_7$-$C_{20}$ alkylaryl group, a $C_8$-$C_{20}$ arylalkenyl group; and $R^{10}$ is selected from $(XR'_n)^-$, wherein X is a Group 14, 15, 16 or 17 heteroatom having an atomic weight of 13 to 79 and $R'$ is one of a hydrogen atom, halogen atom, a $C_1$-$C_{10}$ alkyl group, or a $C_6$-$C_{10}$ aryl group and n is 0, 1, 2 or 3; particularly wherein $R^{10}$ is —$NR'_2$, —$SR'$, —$OR'$, —$OSiR'_3$, —$SiR'_3$, or —$PR'_2$, wherein $R^{10}$ selected from —$NR'_2$, —$SR'$, —$OR'$, —$OSiR'_3$, or —$PR'_2$, wherein $R^{10}$ is —$SR'$, —$OR'$, or —$OSiR'_3$, wherein $R^{10}$ is —$NR'_2$ or —$PR'_2$ radical, or wherein $R^{10}$ is —$OR'$; and $R^{14}$ is a hydrogen atom, a halogen atom, a $C_3$-$C_{10}$ alkyl group which may be halogenated, a $C_6$-$C_{10}$ aryl group which may be halogenated, a $C_2$-$C_{10}$ alkenyl group, a $C_7$-$C_{40}$ arylalkyl group, a $C_7$-$C_{40}$ alkylaryl group, a $C_8$-$C_{40}$ arylalkenyl group, a-$NR'_2$, —$SR'$, —$OR'$, —$OSiR'_3$, or —$PR'_2$ radical, wherein $R'$ is as defined above, preferably a substituted phenyl group, preferably a 3', 5' substituted phenyl group, preferably a 3', 4', 5' substituted phenyl group.

In a preferred embodiment of the invention, particularly useful transition metal complexes of the present invention can be represented the formula (II):

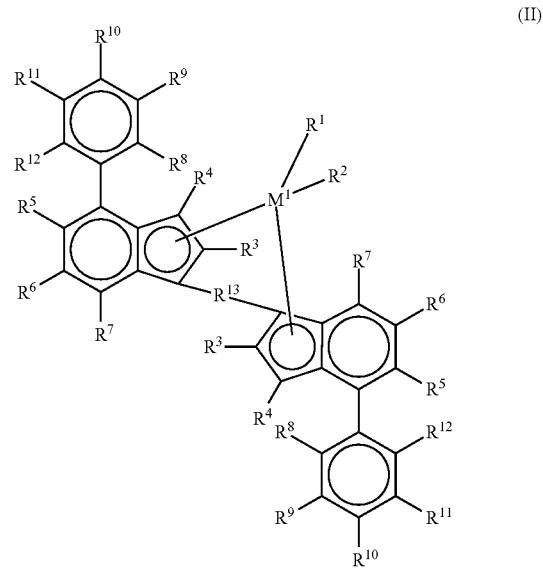

wherein $M^1$, $M^2$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{15}$, $R^{16}$, and $R^{17}$ are as described above.

In a preferred embodiment of the invention in any embodiment of any formula described herein, $M^1$ is Hf, Zr or Ti, preferably Hf or Zr, preferably Zr.

In a preferred embodiment of the invention in any embodiment of any formula described herein, $M^2$ is Si, C or Ge, preferably C or Si, preferably Si.

In a preferred embodiment of the invention in any embodiment of any formula described herein, $R^{15}$, $R^{16}$, and $R^{17}$ are preferably methyl, ethyl, propyl, butyl, pentyl, hexyl, heptyl, octyl, nonyl, decyl, undecyl, or dodecyl.

In a preferred embodiment of the invention in any embodiment of any formula described herein, $R^{13}$ is represented by the formula $R_2{}^aJ$, where J is C, Si, or Ge, and each $R^a$ is, independently, hydrogen, halogen, $C_1$ to $C_{20}$ hydrocarbyl (such as methyl, ethyl, propyl, butyl, pentyl, hexyl, heptyl, octyl, nonyl, decyl, undecyl, or dodecyl) or a $C_1$ to $C_{20}$ substituted hydrocarbyl, and two $R^a$ can form a cyclic structure including aromatic, partially saturated, or saturated cyclic or fused ring system. Preferably, $R^{13}$ is a bridging group comprising carbon or silica, such as dialkylsilyl, preferably $R^{13}$ is selected from $CH_2$, $CH_2CH_2$, $C(CH_3)_2$, $SiMe_2$, $SiPh_2$, $SiMePh$, silylcyclobutyl ($Si(CH_2)_3$), $(Ph)_2C$, $(p\text{-}(Et)_3SiPh)_2C$, and cyclopentasilylene ($Si(CH_2)_4$).

In an alternate embodiment, in any formula described herein, each $R^1$ and $R^2$ is, independently, selected from the group consisting of hydrocarbyl radicals having from 1 to 20 carbon atoms, hydrides, amides, alkoxides, sulfides, phosphides, halides, dienes, amines, phosphines, ethers, and a combination thereof, ($R^1$ and $R^2$ may form a part of a fused ring or a ring system), preferably each $R^1$ and $R^2$ is independently selected from halides and $C_1$ to $C_5$ alkyl groups (preferably methyl groups). Preferably $R^1$ and $R^2$ are selected from chloro, bromo, methyl, ethyl, propyl, butyl, pentyl, hexyl, heptyl, octyl, nonyl, decyl, undecyl, and dodecyl.

Alternatively, $R^1$ and $R^2$ may also be joined together to form an alkanediyl group or a conjugated $C_4$-$C_{40}$ diene ligand which is coordinated to $M^1$ in a metallocyclopentene fashion; $R^1$ and $R^2$ may also be identical or different conjugated dienes, optionally substituted with one or more hydrocarbyl, tri(hydrocarbyl)silyl groups or tri(hydrocarbyl) silylhydrocarbyl groups, said dienes having up to 30 atoms not counting hydrogen and forming a π-complex with $M^1$.

Exemplary groups suitable for $R^1$ and or $R^2$ include 1,4-diphenyl, 1,3-butadiene, 1,3-pentadiene, 2-methyl 1,3-pentadiene, 2,4-hexadiene, 1-phenyl, 1,3-pentadiene, 1,4-dibenzyl, 1,3-butadiene, 1,4-ditolyl-1,3-butadiene, 1,4-bis (trimethylsilyl)-1,3-butadiene, and 1,4-dinaphthyl-1,3-butadiene; preferably $R^1$ and $R^2$ are identical and are a $C_1$-$C_3$ alkyl or alkoxy group, a $C_6$-$C_g$ aryl or aryloxy group, a $C_2$-$C_4$ alkenyl group, a $C_7$-$C_{10}$ arylalkyl group, a $C_7$-$C_{12}$ alkylaryl group, or a halogen atom, particularly chlorine.

In any embodiment of the invention, including any formula described here (particularly formula I or II), the 2 position of the indenyl group or groups, e.g., $R^3$ in formula I or II may be selected from hydrogen, methyl, ethyl, n-propyl, isopropyl, n-butyl, isobutyl, sec-butyl, tert-butyl, pentyl, iso-amyl, hexyl, octyl cyclopropyl, cyclobutyl, cyclopentyl, cyclohexyl, cyclooctyl, or a substituted or unsubstituted phenyl, particularly methyl, ethyl, n-propyl, isopropyl, n-butyl, isobutyl, sec-butyl, tert-butyl, more particularly hydrogen or methyl. In any embodiment of the invention, including any formula described here (particularly formula I and II), the 2 position of the indenyl group or groups, e.g., $R^3$ in formula I or II, is not substituted with a heteroatom, preferably each is independently a hydrocarbyl radical having from 1 to 20 carbon atoms that is not substituted with a heteroatom.

In any embodiment of the invention, including any formula described here (particularly formula I or II), $R^4$, $R^5$, $R^6$, and $R^7$ may be identical or different and are each a hydrogen atom, a halogen atom, a $C_1$-$C_{10}$ alkyl group (methyl, ethyl, propyl, butyl, pentyl, hexyl, heptyl, octyl, nonyl, decyl, undecyl, dodecyl or an isomer thereof) which may be halogenated, or a $C_6$-$C_{10}$ aryl group which may be halogenated.

In any embodiment of the invention, including any formula described here (particularly formula I or II), $R^8$ and $R^{12}$ may be identical or different and are each a hydrogen atom, a halogen atom, a $C_1$-$C_{10}$ alkyl group (preferably $C_2$ to $C_{10}$, preferably $C_3$ to $C_{10}$, preferably methyl, ethyl, propyl, butyl, pentyl, hexyl, heptyl, octyl, nonyl, decyl, undecyl, dodecyl or an isomer thereof) which may be halogenated, a $C_6$-$C_{10}$ aryl group which may be halogenated, preferably methyl, ethyl, propyl, butyl, pentyl, hexyl, phenyl, octyl, nonyl, decyl, undecyl, dodecyl, preferably methyl, ethyl, or phenyl.

In any embodiment of the invention, including any formula described here (particularly formula I or II), $R^9$ and $R^{11}$ are identical or different and selected from $C_2$-$C_{20}$ alkyl group (preferably $C_3$ to $C_{16}$, preferably $C_4$ to $C_{12}$, preferably butyl, pentyl, hexyl, heptyl, octyl, nonyl, decyl, undecyl, dodecyl and isomers thereof) which may be halogenated, a $C_6$-$C_{10}$ aryl group which may be halogenated. In some embodiments, $R^9$ and $R^{11}$ may be the same or different and are each a butyl group, an aryl group, an isopropyl group, or a fluoroalkyl group, particularly wherein each of $R^9$ and $R^{11}$ is selected from the group consisting of propyl, isopropyl, n-propyl, n-butyl-, iso-butyl-, and tert-butyl groups. In a preferred embodiment of the invention $R^9$ and $R^{11}$ are identical or different and are a $C_4$ to $C_{20}$, preferably $C_4$ to $C_{12}$ alkyl group and each $R^3$ is independently a hydrocarbyl radical having from 1 to 20 carbon atoms that is not substituted with a heteroatom.

In any embodiment of the invention, including any formula described here (particularly formula I or II), $R^{10}$ is selected from $-NR'_2$, $-SR'$, $-OR'$, $-OSiR'_3$ or $-PR'_2$ radical, wherein R' is one of a hydrogen atom, halogen atom, a $C_1$-$C_{10}$ alkyl group, or a $C_6$-$C_{10}$ aryl group, particularly wherein $R^{10}$ is OR' wherein R' is a $C_1$-$C_{10}$ alkyl group, particularly a methoxy, ethoxy, n-propoxy, isopropoxy, n-butoxy, iso-butoxy, sec-butoxy, or t-butoxy group, most particularly methoxy.

In any embodiment of the invention, including any formula described here (particularly formula I or II), $R^{14}$ is a substituted or unsubstituted $C_6$-$C_{10}$ aryl group (preferably phenyl, naphthyl, indenyl, preferably phenyl) which may be substituted (such as halogenated), e.g., a substituted or unsubstituted phenyl, napthyl, or indenyl. Preferably, $R^{14}$ may be phenyl, particularly 3'- and/or 5'-substituted phenyl, more particularly wherein the 3' and/or 5' substituents are selected from $C_2$-$C_{20}$ alkyl group which may be halogenated, a $C_6$-$C_{10}$ aryl group which may be halogenated, a $C_2$-$C_{10}$ alkenyl group, a $C_7$-$C_{20}$ arylalkyl group, a $C_7$-$C_{20}$ alkylaryl group, a $C_8$-$C_{20}$ arylalkenyl group. In certain embodiments of the invention, where $R^{14}$ is phenyl, the 3' and 5' positions may be the same or different and are each a butyl group, an aryl group, an isopropyl group, or a fluoroalkyl group, particularly wherein each is selected from the group consisting of n-butyl-, iso-butyl-, and tert-butyl groups, most particularly wherein each is a tert-butyl group. In certain embodiments of the invention, where $R^{14}$ is phenyl, the 3' and 5' positions may be the same or different and are each a butyl group, an aryl group, an isopropyl group, or a fluoroalkyl group (particularly wherein each is selected from the group consisting of n-butyl-, iso-butyl-, and tert-butyl groups, most particularly wherein each is a tert-butyl group); and the phenyl is also substituted at the 4' position with a $-NR'_2$, $-SR'$, $-OR'$, $-OSiR'_3$ or $-PR'_2$ radical, wherein R' is one of a hydrogen atom, halogen atom, a $C_1$-$C_{10}$ alkyl group, or a $C_6$-$C_{10}$ aryl group, preferably alkyloxy, preferably methoxy, ethoxy, n-propoxy, iso-propoxy, n-butoxy, iso-butoxy, sec-butoxy, or t-butoxy group.

In some embodiments, $R^3$ is a selected from hydrogen and methyl; each of $R^9$ and $R^{11}$ is selected from the group consisting of n-butyl-, iso-butyl-, and particularly tert-butyl groups. In still other embodiments, $R^3$ is selected from hydrogen and methyl; each of $R^9$ and $R^{11}$ is selected from the group consisting of n-butyl-, iso-butyl-, and particularly tert-butyl groups; and $R^{10}$ is a methoxy, ethoxy, n-propoxy, isopropoxy, n-butoxy, iso-butoxy, sec-butoxy, or t-butoxy group, particularly a methoxy group.

In some embodiments, $R^3$ is selected from hydrogen and cyclopropyl; each of $R^9$ and $R^{11}$ is selected from the group consisting of n-butyl-, iso-butyl-, and particularly tert-butyl groups. In still other embodiments, $R^3$ is a selected from hydrogen and cyclopropyl; each of $R^9$ and $R^{11}$ is selected from the group consisting of n-butyl-, iso-butyl-, and particularly tert-butyl groups; and $R^{10}$ is a methoxy, ethoxy, n-propoxy, isopropoxy, n-butoxy, iso-butoxy, sec-butoxy, or t-butoxy group, particularly a methoxy group.

Some transition metal complexes useful herein may be described as bridged bis(4-phenyl-indenyl) transition metal complexes wherein: at least one of the 4-phenyl rings is substituted at the 3' and 5' positions by radicals which may be identical or different and selected from $C_2$-$C_{20}$ alkyl group which may be halogenated, a $C_6$-$C_{10}$ aryl group which may be halogenated, a $C_2$-$C_{10}$ alkenyl group, a $C_7$-$C_{20}$ arylalkyl group, a $C_7$-$C_{20}$ alkylaryl group, a $C_8$-$C_{20}$ arylalkenyl group, wherein at least one of the phenyl rings substituted at the 3' and 5' positions is also substituted at the 4' position with a —NR'$_2$, —SR', —OR', —OSiR'$_3$ or —PR'$_2$ radical, wherein R' is one of a hydrogen atom, halogen atom, a $C_1$-$C_{10}$ alkyl group, or a $C_6$-$C_{10}$ aryl group; and optionally, wherein one or more of the remaining positions on the phenyl and/or indenyl ring(s) of the transition metal complex are substituted. In particular embodiments, each of the 4-phenyl rings is substituted at the 3' and 5' positions by radicals which may be identical or different and selected from $C_2$-$C_{20}$ alkyl group which may be halogenated, a $C_6$-$C_{10}$ aryl group which may be halogenated, a $C_2$-$C_{10}$ alkenyl group, a $C_7$-$C_{20}$ arylalkyl group, a $C_7$-$C_{20}$ alkylaryl group, a $C_8$-$C_{20}$ arylalkenyl group. In some transition metal complexes at least one or both of the 4-pheny-indenyl ligands comprises an $R^3$ group at the 2-position of 4-pheny-indenyl ligand, wherein $R^3$ may be a hydrogen atom, a halogen atom, a $C_1$-$C_{10}$ alkyl group which may be halogenated, a $C_6$-$C_{10}$ aryl group which may be halogenated, a $C_2$-$C_{10}$ alkenyl group, a $C_7$-$C_{40}$ arylalkyl group, a $C_7$-$C_{40}$ alkylaryl group, a $C_8$-$C_{40}$ arylalkenyl group, a-NR'$_2$, —SR', —OR', —OSiR'$_3$ or —PR'$_2$ radical, wherein R' is one of a halogen atom, a $C_1$-$C_{10}$ alkyl group, or a $C_6$-$C_{10}$ aryl group. In particular embodiments, when either $R^3$ is a hydrogen atom, a methyl or ethyl group, then both phenyl rings are substituted at the 3' and 5' positions by butyl groups which may be the same or different. In some transition metal complexes at least one 4-phenyl group is substituted at the 3' and 5' position with a tert-butyl group and at the 4' position with a OR' radical, wherein R' is one of a hydrogen atom, halogen atom, a $C_1$-$C_{10}$ alkyl group, particularly methoxy, or a $C_6$-$C_{10}$ aryl group.

Particularly useful transition metal complexes are Zr- or Hf-based complexes. Additionally, some such transition metal complexes are bridged by a dialkylsiladiyl group or a diisopropylamidoborane group.

Particularly preferred transition metal complexes of the present invention are represented the formula (II) above wherein: $M^1$ is selected from the group consisting of titanium, zirconium, and hafnium, particularly zirconium or hafnium, more typically zirconium; $R^1$ and $R^2$ are identical or different, and are one of a hydrogen atom, a $C_1$-$C_{10}$ alkyl group (preferably methyl, ethyl, butyl, pentyl, hexyl, heptyl, octyl, nonyl, decyl, undecyl, dodecyl and isomers thereof), or a halogen atom (preferably Cl, Br, F or I).

In particular embodiments complexes according to formula (II), the $R^3$ groups may be identical or different and are each a hydrogen atom, a halogen atom, a $C_1$-$C_{10}$ alkyl group (preferably $C_2$ to $C_{10}$, preferably $C_3$ to $C_8$, preferably methyl, ethyl, butyl, pentyl, hexyl, heptyl, octyl, nonyl, decyl, undecyl, dodecyl or an isomer thereof) which may be halogenated, a $C_6$-$C_{10}$ aryl group which may be halogenated. In some embodiments, each $R^3$ may be the same or different and are each a $C_1$-$C_{10}$ alkyl group. In particular embodiments, $R^3$ is not a hydrogen atom, e.g., in particular embodiments, each $R^3$ is identical and is a fluorine, chlorine or bromine, a $C_1$-$C_4$ alkyl group which may be halogenated, a $C_6$-$C_8$ aryl group which may be halogenated, a-NR'$_2$, —SR', —OR, —OSiR'$_3$ or —PR'$_2$ radical, wherein R' is one of a chlorine atom, a $C_1$-$C_4$ alkyl group, or a $C_6$-$C_8$ aryl group; preferably $R^3$ are identical and are each a $C_1$-$C_3$ alkyl group, preferably each $R_3$ is a $C_1$-$C_2$ (e.g., —$CH_3$ or —$CH_2CH_3$) group.

In a preferred embodiment, in formula (II), the $R^4$ to $R^7$ groups are identical or different and may be hydrogen, a halogen atom, a $C_1$-$C_{10}$ alkyl group (preferably methyl, ethyl, butyl, pentyl, hexyl, heptyl, octyl, nonyl, decyl, undecyl, dodecyl or an isomer thereof) which may be halogenated, a $C_6$-$C_{10}$ aryl group which may be halogenated. In particular embodiments, two or more adjacent radicals $R^5$ to $R^7$ together with the atoms connecting them form one or more rings, preferably a 6-membered ring, preferably 4-8 membered ring.

In a preferred embodiment, in formula (II) $R^{13}$ is —SiR"$_2$— wherein the R" groups may be the same or different and are each selected from a hydrogen or a $C_1$-$C_{10}$ alkyl group, preferably a $C_1$-$C_2$ alkyl group (e.g., methyl or ethyl) or wherein $R^{13}$ is a $C_1$-$C_{10}$ dialkylamidoborane.

In a preferred embodiment, in formula (II), each $R^8$ and $R^{12}$ may be identical or different and are each a hydrogen atom, a halogen atom, a $C_3$-$C_{10}$ alkyl group which may be halogenated, a $C_6$-$C_{10}$ aryl group which may be halogenated.

In a preferred embodiment, in formula (II), each $R^9$ and $R^{11}$ may be identical or different and are each a $C_1$-$C_{20}$ alkyl group which may be halogenated, a $C_6$-$C_{10}$ aryl group which may be halogenated, a $C_2$-$C_{10}$ alkenyl group, a $C_7$-$C_{20}$ arylalkyl group, a $C_7$-$C_{20}$ alkylaryl group, or a $C_8$-$C_{20}$ arylalkenyl group. In particular embodiments according to formula (II), each $R^9$ and each $R^{11}$ is selected from the group consisting of primary, secondary or tertiary butyl groups, aryl groups, isopropyl groups, fluoroalkyl groups, trialkyl silyl groups, or other groups of similar size, preferably a tertiary butyl group, particularly n-butyl-, iso-butyl-, and tert-butyl groups.

In any embodiment of the invention, including any formula described here (particularly formula I or II, particularly formula (II)), each $R^{10}$ is selected from $(XR'_n)^-$, wherein X is a Group 14-17 heteroatom having an atomic weight of 13 to 79 and R' is one of a hydrogen atom, halogen atom, a $C_1$-$C_{10}$ alkyl group, or a $C_6$-$C_{10}$ aryl group and n is 0, 1, 2, or 3; preferably $R^{10}$ is —NR'$_2$, —SR', —OR', —OSiR'$_3$, —SiR'$_3$, or —PR'$_2$, preferably $R^{10}$ is —NR'$_2$, —SR', —OR', —OSiR'$_3$, or —PR'$_2$, wherein $R^{10}$ is —SR', —OR', or —OSiR'$_3$, preferably $R^{10}$ is a —NR'$_2$ or —PR'$_2$ radical, preferably $R^{10}$ is —OR'. Preferably, each $R^{10}$ is selected from the group consisting of —$NH_2$, —NH(methyl), —NH (ethyl), —NH(n-propyl), —NH(iso-propyl), —NH(phenyl), N(methyl)$_2$, —N(methyl)(ethyl), —N(n-propyl)(phenyl), —N(iso-propyl)(phenyl), —N(methyl)(phenyl), N(ethyl) (ethyl), —N(ethyl)(n-propyl), —N(ethyl)(iso-propyl), —N(n-propyl)(phenyl), —N(phenyl)(phenyl), etc.; —SH, —S(methyl), —S(ethyl), —S(n-propyl), —S(iso-propyl), —S(n-butyl), —S(iso-butyl), —S(sec-butyl), —S(tert-butyl), —S(phenyl) etc.; —OH, —O(methyl), —O(ethyl), —O(n-propyl), —O(iso-propyl), —O(n-butyl), —O(iso-butyl), —O(sec-butyl), —O(tert-butyl), —O(phenyl), etc.; —OSiH$_3$, —OSiH$_2$(methyl), —OSiH(methyl)$_2$, —OSi(methyl)$_3$, —OSiH$_2$(ethyl), —OSiH(ethyl)$_2$, —OSi(ethyl)$_3$, —OSiH$_2$(propyl), —OSiH(propyl)$_2$, —OSi(propyl)$_3$, —OSiH$_2$(butyl), —OSiH(butyl)$_2$, —OSi(butyl)$_3$, —OSiH(methyl)(ethyl), —OSi(methyl)(ethyl)$_2$, —OSiH(methyl)(propyl), —OSi(methyl)(propyl)$_2$, —O SiH(methyl)(butyl), —OSi(methyl)(butyl)$_2$, —OSiH(ethyl)(propyl), —OSi(ethyl)(propyl)$_2$, —OSiH(ethyl)(butyl), —OSi(ethyl)(butyl)$_2$, etc., —PH$_2$, —PH(methyl), —PH(ethyl), —PH(n-propyl), —PH(iso-propyl), —PH(phenyl), —P(methyl)$_2$, —P(methyl)(ethyl), —P(n-propyl)(phenyl), —P(iso-propyl)(phenyl), —P(methyl)(phenyl), P(ethyl)(ethyl), —P(ethyl)(n-propyl), —P(ethyl)(iso-propyl), —P(n-propyl)(phenyl), —P(phenyl)(phenyl), etc.; —SiH$_3$, —SiH$_2$(methyl), —SiH(methyl)$_2$, —Si(methyl)$_3$, —SiH$_2$(ethyl), —SiH(ethyl)$_2$, —OSi(ethyl)$_3$, —SiH$_2$(propyl), —SiH(propyl)$_2$, —Si(propyl)$_3$, —SiH$_2$(butyl), —SiH(butyl)$_2$, —Si(butyl)$_3$, —SiH(methyl)(ethyl), —Si(methyl)(ethyl)$_2$, —SiH(methyl)(propyl), —Si(methyl)(propyl)$_2$, —SiH(methyl)(butyl), —Si(methyl)(butyl)$_2$, —OSiH(ethyl)(propyl), —OSi(ethyl)(propyl)$_2$, —OSiH(ethyl)(butyl), —OSi(ethyl)(butyl)$_2$, and the like.

In any embodiment of the invention, including any formula described here (particularly formula I or II), each $R^9$ and each $R^{11}$ is selected from the group consisting of primary, secondary or tertiary butyl groups, aryl groups, isopropyl groups, preferably a tert-butyl group, particularly a tert-butyl group; and at least one $R^{10}$ is —OH, —O(methyl), —O(ethyl), —O(n-propyl), —O(iso-propyl), —O(n-butyl), —O(iso-butyl), —O(sec-butyl), —O(tert-butyl), —O(phenyl), particularly —O(methyl). In particular, in such embodiments, each $R^{10}$ is selected from —OH, —O(methyl), —O(ethyl), —O(n-propyl), —O(iso-propyl), —O(n-butyl), —O(iso-butyl), —O(sec-butyl), —O(tert-butyl), —O(phenyl), particularly wherein each $R^{10}$ is —O(methyl).

More specifically, in certain embodiments, each $R^1$ and $R^2$ may be the same or different and are each a halogen atom, preferably Cl; each $R^3$ may be the same or different and are each a $C_1$-$C_{10}$ alkyl group, preferably methyl; each $R^4$, $R^5$, $R^6$, and $R^7$ may be the same or different and are each a hydrogen atom or $C_1$-$C_{10}$ alkyl group, preferably each is a hydrogen atom; each $R^8$ and $R^{12}$ are each a hydrogen atom; $R^{13}$ is —SiR"$_2$— wherein each R" may be the same or different and are each a hydrogen or $C_1$-$C_{10}$ alkyl group, preferably methyl; each $R^9$ and $R^{11}$ is a $C_1$-$C_{10}$ alkyl group, particularly n-butyl-, iso-butyl-, and tert-butyl, more particularly a tert-butyl group; and wherein each $R^{10}$ is —OH, —O(methyl), —O(ethyl), —O(n-propyl), —O(iso-propyl), —O(n-butyl), —O(iso-butyl), —O(sec-butyl), —O(tert-butyl), —O(phenyl), particularly —O(methyl).

In particular embodiments, transition metal complexes according to formula (II) include those wherein each $R^1$ and $R^2$ are chlorine; each $R^3$ is methyl; each $R^4$, $R^5$, $R^6$, and $R^7$, $R^8$, and $R^{12}$ are hydrogen; $R^{13}$ is —Si(CH$_3$)$_2$—; wherein each $R^9$ and $R^{11}$ is a tert-butyl group; and wherein each $R^{10}$ is a methoxy group.

The following particular zirconium-containing metallocenes and their hafnium-containing analogs are expressly disclosed: rac-dimethylsiladiyl (2-methyl, 4-[3',5'-di-tert-butyl-4'-methoxyphenyl]indenyl)$_2$ZrCl$_2$; rac-dimethylsiladiyl (2-ethyl, 4-[3',5'-di-tert-butyl-4'-methoxyphenyl]indenyl)$_2$ZrCl$_2$; rac-dimethylsiladiyl (2-propyl, 4-[3',5'-di-tert-butyl-4'-methoxyphenyl]indenyl)$_2$ZrCl$_2$; rac-dimethylsiladiyl (2-butyl, 4-[3',5'-di-tert-butyl-4'-methoxyphenyl]indenyl)$_2$ZrCl$_2$; rac-dimethylsiladiyl (2-methyl, 4-[3',5'-bistrifluoromethyl-4'-methoxyphenyl]indenyl)$_2$ZrCl$_2$; rac-dimethylsiladiyl (2-ethyl, 4-[3',5'-bistrifluoromethyl-4'-methoxyphenyl]indenyl)$_2$ZrCl$_2$; rac-dimethylsiladiyl (2-propyl, 4-[3',5'-bistrifluoromethyl-4'-methoxyphenyl]indenyl)$_2$ZrCl$_2$; rac-dimethylsiladiyl (2-butyl, 4-[3',5'-bistrifluoromethyl-4'-methoxyphenyl]indenyl)$_2$ZrCl$_2$; rac-dimethylsiladiyl (2-methyl, 4-[3',5'-di-iso-propyl-4'-methoxyphenyl]indenyl)$_2$ZrCl$_2$; rac-dimethylsiladiyl (2-ethyl, 4-[3',5'-di-iso-propyl-4'-methoxyphenyl]indenyl)$_2$ZrCl$_2$; rac-dimethylsiladiyl (2-propyl, 4-[3',5'-di-iso-propyl-4'-methoxyphenyl]indenyl)$_2$ZrCl$_2$; rac-dimethylsiladiyl (2-butyl, 4-[3',5'-di-iso-propyl-4'-methoxyphenyl]indenyl)$_2$ZrCl$_2$; rac-dimethylsiladiyl (2-methyl, 4-[3',5'-di-phenyl-4'-methoxyphenyl]indenyl)$_2$ZrCl$_2$; rac-dimethylsiladiyl (2-ethyl, 4-[3',5'-di-phenyl-4'-methoxyphenyl]indenyl)$_2$ZrCl$_2$; rac-dimethylsiladiyl (2-propyl, 4-[3',5'-di-phenyl-4'-methoxyphenyl]indenyl)$_2$ZrCl$_2$; rac-dimethylsiladiyl (2-butyl, 4-[3',5'-di-phenyl-4'-methoxyphenyl]indenyl)$_2$ZrCl$_2$; rac-dimethylamidoborane (2-methyl, 4-[3',5'-di-tert-butyl-4'-methoxyphenyl]indenyl)$_2$ZrCl$_2$; rac-dimethylamidoborane (2-ethyl, 4-[3',5'-di-tert-butyl-4'-methoxyphenyl]indenyl)$_2$ZrCl$_2$; rac-dimethylamidoborane (2-propyl, 4-[3',5'-di-tert-butyl-4'-methoxyphenyl]indenyl)$_2$ZrCl$_2$; rac-dimethylamidoborane (2-butyl, 4-[3',5'-di-tert-butyl-4'-methoxyphenyl]indenyl)$_2$ZrCl$_2$; rac-dimethylamidoborane (2-methyl, 4-[3',5'-bistrifluoromethyl-4'-methoxyphenyl]indenyl)$_2$ZrCl$_2$; rac-dimethylamidoborane (2-ethyl, 4-[3',5'-bistrifluoromethyl-4'-methoxyphenyl]indenyl)$_2$ZrCl$_2$; rac-dimethylamidoborane (2-propyl, 4-[3',5'-bistrifluoromethyl-4'-methoxyphenyl]indenyl)$_2$ZrCl$_2$; rac-dimethylamidoborane (2-butyl, 4-[3',5'-bistrifluoromethyl-4'-methoxyphenyl]indenyl)$_2$ZrCl$_2$; rac-dimethylamidoborane (2-methyl, 4-[3',5'-di-iso-propyl-4'-methoxyphenyl]indenyl)$_2$ZrCl$_2$; rac-dimethylamidoborane (2-ethyl, 4-[3',5'-di-iso-propyl-4'-methoxyphenyl]indenyl)$_2$ZrCl$_2$; rac-dimethylamidoborane (2-propyl, 4-[3',5'-di-iso-propyl-4'-methoxyphenyl]indenyl)$_2$ZrCl$_2$; rac-dimethylamidoborane (2-tert-butyl, 4-[3',5'-di-iso-propyl-4'-methoxyphenyl]indenyl)$_2$ZrCl$_2$; rac-dimethylamidoborane (2-methyl, 4-[3',5'-di-phenyl-4'-methoxyphenyl]indenyl)$_2$ZrCl$_2$; rac-dimethylamidoborane (2-ethyl, 4-[3',5'-di-phenyl-4'-methoxyphenyl]indenyl)$_2$ZrCl$_2$; rac-dimethylamidoborane (2-propyl, 4-[3',5'-diphenyl-4'-methoxyphenyl]indenyl)$_2$ZrCl$_2$; rac-dimethylamidoborane (2-butyl, 4-[3',5'-diphenyl-4'-methoxyphenyl]indenyl)$_2$ZrCl$_2$; rac-di-iso-propylamidoborane (2-methyl, 4-[3',5'-di-tert-butyl-4'-methoxyphenyl]indenyl)$_2$ZrCl$_2$; rac-di-iso-propylamidoborane (2-ethyl, 4-[3',5'-di-tert-butyl-4'-methoxyphenyl]indenyl)$_2$ZrCl$_2$; rac-di-iso-propylamidoborane (2-propyl, 4-[3',5'-di-tert-butyl-4'-methoxyphenyl]indenyl)$_2$ZrCl$_2$; rac-di-iso-propylamidoborane (2-butyl, 4-[3',5'-di-tert-butyl-4'-methoxyphenyl]indenyl)$_2$ZrCl$_2$; rac-di-iso-propylamidoborane (2-methyl, 4-[3',5'-bistrifluoromethyl-4'-methoxyphenyl]indenyl)$_2$ZrCl$_2$; rac-di-iso-propylamidoborane (2-ethyl, 4-[3',5'-bistrifluoromethyl-4'-methoxyphenyl]indenyl)$_2$ZrCl$_2$; rac-di-iso-propylamidoborane (2-propyl, 4-[3',5'-bistrifluoromethyl-4'-methoxyphenyl]indenyl)$_2$ZrCl$_2$; rac-di-iso-propylamidoborane (2-butyl, 4-[3',5'-bistrifluoromethyl-4'-methoxyphenyl]indenyl)$_2$ZrCl$_2$; rac-di-iso-propylamidoborane (2-methyl, 4-[3',5'-di-iso-propyl-4'-methoxyphenyl]indenyl)$_2$ZrCl$_2$; rac-di-iso-propylamidoborane (2-ethyl, 4-[3',5'-di-iso-propyl-4'-methoxyphenyl] indenyl)$_2$ZrCl$_2$; rac-di-iso-propylamidoborane (2-propyl, 4-[3',5'-di-iso-propyl-4'-methoxyphenyl]indenyl)$_2$ZrCl$_2$; rac-di-iso-propylamidoborane (2-tert-butyl, 4-[3',5'-di-iso-propyl-4'-methoxyphenyl]indenyl)$_2$ZrCl$_2$; rac-di-iso-propylamidoborane (2-methyl, 4-[3',5'-diphenyl-4'-methoxyphenyl]indenyl)$_2$ZrCl$_2$; rac-di-iso-propylamidoborane (2-ethyl, 4-[3',5'-di-phenyl-4'-methoxyphenyl]indenyl)$_2$ZrCl$_2$; rac-di-iso-propylamidoborane (2-propyl, 4-[3',5'-diphenyl-4'-methoxyphenyl]indenyl)$_2$ZrCl$_2$; rac-di-iso-propylamidoborane (2-butyl, 4-[3',5'-diphenyl-4'-methoxyphenyl]indenyl)$_2$ZrCl$_2$; rac-bis(trimethylsilyl)amidoborane (2-methyl, 4-[3',5'-di-tert-butyl-4'-methoxyphenyl]indenyl)$_2$ZrCl$_2$; rac-bis(trimethylsilyl)amidoborane (2-ethyl, 4-[3',5'-di-tert-butyl-4'-methoxyphenyl]indenyl)$_2$ZrCl$_2$; rac-bis(trimethylsilyl)amidoborane (2-propyl, 4-[3',5'-di tbutyl-4'-methoxyphenyl]indenyl)$_2$ZrCl$_2$; rac-bis(trimethylsilyl)amidoborane (2-butyl, 4-[3',5'-di tbutyl-4'-methoxyphenyl]indenyl)$_2$ZrCl$_2$; rac-bis(trimethylsilyl)amidoborane (2-methyl, 4-[3',5'-bis trifluoromethyl-4'-methoxyphenyl]indenyl)$_2$ZrCl$_2$; rac-bis(trimethylsilyl)amidoborane (2-ethyl, 4-[3',5'-bis trifluoromethyl-4'-methoxyphenyl]indenyl)$_2$ZrCl$_2$; rac-bis(trimethylsilyl)amidoborane (2-propyl, 4-[3',5'-bis trifluoromethyl-4'-methoxyphenyl]indenyl)$_2$ZrCl$_2$; rac-bis(trimethylsilyl)amidoborane (2-butyl, 4-[3',5'-bis-trifluoromethyl-4'-methoxyphenyl]indenyl)$_2$ZrCl$_2$; rac-bis(trimethylsilyl)amidoborane (2-methyl, 4-[3',5'-di-iso-propyl-4'-methoxyphenyl]indenyl)$_2$ZrCl$_2$; rac-bis(trimethylsilyl)amidoborane (2-ethyl, 4-[3',5'-di-iso-propyl-4'-methoxyphenyl]indenyl)$_2$ZrCl$_2$; rac-bis(trimethylsilyl)amidoborane (2-propyl, 4-[3',5'-di-iso-propyl-4'-methoxyphenyl]indenyl)$_2$ZrCl$_2$; rac-bis(trimethylsilyl)amidoborane (2-butyl, 4-[3',5'-di-iso-propyl-4'-methoxyphenyl]indenyl)$_2$ZrCl$_2$; rac-bis(trimethylsilyl)amidoborane (2-methyl, 4-[3',5'-diphenyl-4'-methoxyphenyl]indenyl)$_2$ZrCl$_2$; rac-bis(trimethylsilyl)amidoborane (2-ethyl, 4-[3',5'-diphenyl-4'-methoxyphenyl]indenyl)$_2$ZrCl$_2$; rac-bis(trimethylsilyl)amidoborane (2-propyl, 4-[3',5'-diphenyl-4'-methoxyphenyl]indenyl)$_2$ZrCl$_2$; rac-bis(trimethylsilyl)amidoborane (2-butyl, 4-[3',5'-diphenyl-4'-methoxyphenyl]indenyl)$_2$ZrCl$_2$.

While 4'-methoxy (i.e, O(methyl)) analogs are enumerated above, —O(ethyl), —O(n-propyl), —O(iso-propyl), —O(n-butyl), —O(iso-butyl), —O(sec-butyl), —O(tert-butyl), —O(phenyl), etc.; —OSiH$_3$, —OSiH$_2$(methyl), —OSiH(methyl)$_2$, —OSi(methyl)$_3$, —OSiH$_2$(ethyl), —OSiH(ethyl)$_2$, —OSi(ethyl)$_3$, —OSiH$_2$(propyl), —OSiH(propyl)$_2$, —OSi(propyl)$_3$, —OSiH$_2$(butyl), —OSiH(butyl)$_2$, —OSi(butyl)$_3$, —OSiH(methyl)(ethyl), —OSi(methyl)(ethyl)$_2$, —OSiH(methyl)(propyl), —OSi(methyl)(propyl)$_2$, —OSiH(methyl)(butyl), —OSi(methyl)(butyl)$_2$, —OSiH(ethyl)(propyl), —OSi(ethyl)(propyl)$_2$, —OSiH(ethyl)(butyl), —OSi(ethyl)(butyl)$_2$ analogs are also expressly disclosed. Likewise, while the dichloro-substituted compounds (—ZrCl$_2$ and —HfCl$_2$) are enumerated above, the compounds where each of the chloride are replaced with methyl groups (e.g., —Zr((CH$_3$)$_2$ and —Hf(CH$_3$)$_2$)) are also expressly disclosed. And while the complexes above are substituted at the 2-position of the indene ring, analogs wherein the substitution occurs instead at the 1, 3, 4, 5, 6, and/or 7 position of the indene ring are also envisioned.

In another embodiment of the invention the 2, 4 and 6 positions of the indenyl ring are substituted, e.g., in formula I, $R^3$, $R^{14}$ and $R_6$ are not H and in formula (II) $R^3$ and $R_6$ are not H.

In a preferred embodiment of the invention in any of the processes described herein one catalyst compound is used, e.g., the catalyst compounds are not different. For purposes of this invention one metallocene catalyst compound is considered different from another if they differ by at least one atom. For example "bisindenyl ZrCl$_2$" is different from (indenyl)(2-methylindenyl) ZrCl$_2$" which is different from "(indenyl)(2-methylindenyl) HfCl$_2$." Catalyst compounds that differ only by isomer are considered the same for purposes if this invention, e.g., rac-dimethylsilylbis(2-methyl 4-phenyl)Hf(Me)$_2$ is considered to be the same as meso-dimethylsilylbis(2-methyl 4-phenyl)Hf(Me)$_2$.

In some embodiments, two or more different catalyst compounds are present in the catalyst system used herein. In some embodiments, two or more different catalyst compounds are present in the reaction zone where the process (es) described herein occur. When two transition metal compound based catalysts are used in one reactor as a mixed catalyst system, the two transition metal compounds are preferably chosen such that the two are compatible. A simple screening method such as by $^1$H or $^{13}$C NMR, known to those of ordinary skill in the art, can be used to determine which transition metal compounds are compatible. It is preferable to use the same activator for the transition metal compounds, however, two different activators, such as a non-coordinating anion activator and an alumoxane, can be used in combination. If one or more transition metal compounds contain an $R^1$ or $R^2$ ligand which is not a hydride, hydrocarbyl, or substituted hydrocarbyl, then the alumoxane should be contacted with the transition metal compounds prior to addition of the non-coordinating anion activator.

The two transition metal compounds (pre-catalysts) may be used in any ratio. Preferred molar ratios of (A) transition metal compound to (B) transition metal compound fall within the range of (A:B) 1:1000 to 1000:1, alternatively 1:100 to 500:1, alternatively 1:10 to 200:1, alternatively 1:1 to 100:1, and alternatively 1:1 to 75:1, and alternatively 5:1 to 50:1. The particular ratio chosen will depend on the exact pre-catalysts chosen, the method of activation, and the end product desired. In a particular embodiment, when using the two pre-catalysts, where both are activated with the same activator, useful mole percents, based upon the molecular weight of the pre-catalysts, are 10 to 99.9% A to 0.1 to 90% B, alternatively 25 to 99% A to 0.5 to 50% B, alternatively 50 to 99% A to 1 to 25% B, and alternatively 75 to 99% A to 1 to 10% B.

Methods to Prepare the Catalyst Compounds

All air sensitive syntheses are carried out in nitrogen purged dry boxes. All solvents are available from commercial sources. 4-Bromo-2-methyl indene, 4-chloro-2-methyl-indene and tris(perfluorophenyl)borane in toluene are available from commercial sources. Aluminum alkyls are available as hydrocarbon solutions from commercial sources. Methylalumoxane ("MAO") is available from Albemarle as a 30 wt % solution in toluene. Racemic dimethylsiladiyl (2-methyl-4-phenylindenyl)$_2$ZrCl$_2$ is obtainable from commercial sources as well.

Generally, metallocenes of this type may be synthesized according to the schematic reaction procedure described in FIG. 1 where (i) is a deprotonation via a metal salt of alkyl anion (e.g. n-BuLi) to form an indenide; (ii) is reaction of indenide with an appropriate bridging precursor (e.g. Me$_2$SiCl$_2$); (iii) is reaction of the above product with AgOTf; (iv) is reaction of the above triflate compound with another equivalent of indenide; (v) is double deprotonation via an alkyl anion (e.g. n-BuLi) to form a dianion; (vi) is reaction of the dianion with a metal halide (e.g. ZrCl$_4$). The final products are obtained by recrystallization of the crude solids.

Activators

After the complexes have been synthesized, catalyst systems may be formed by combining them with activators in any manner known from the literature, including by supporting them for use in slurry or gas phase polymerization. The catalyst systems may also be added to or generated in solution polymerization or bulk polymerization (in the monomer). The catalyst system typically comprises a transition metal complex as described above and an activator such as alumoxane or a non-coordinating anion activator. Activation may be performed using alumoxane solution including methyl alumoxane, referred to as MAO, as well as modified MAO, referred to herein as MMAO, which contains some higher alkyl groups to improve the solubility. Particularly useful MAO can be purchased from Albemarle, typically in a 10 wt % solution in toluene. The catalyst system employed in the present invention preferably uses an activator selected from alumoxanes, such as methyl alumoxane, modified methyl alumoxane, ethyl alumoxane, iso-butyl alumoxane, and the like.

When an alumoxane or modified alumoxane is used, the complex-to-activator molar ratio is from about 1:3000 to 10:1; alternatively 1:2000 to 10:1; alternatively 1:1000 to 10:1; alternatively 1:500 to 1:1; alternatively 1:300 to 1:1; alternatively 1:200 to 1:1; alternatively 1:100 to 1:1; alternatively 1:50 to 1:1; alternatively 1:10 to 1:1. When the activator is an alumoxane (modified or unmodified), some embodiments select the maximum amount of activator at a 5000-fold molar excess over the catalyst precursor (per metal catalytic site). The preferred minimum activator-to-complex ratio is 1:1 molar ratio.

Activation may also be performed using non-coordinating anions, referred to as NCA's, of the type described in EP 277 003 A1 and EP 277 004 A1. NCA may be added in the form of an ion pair using, for example, [DMAH]+ [NCA]– in which the N,N-dimethylanilinium (DMAH) cation reacts with a basic leaving group on the transition metal complex to form a transition metal complex cation and [NCA]—. The cation in the precursor may, alternatively, be trityl. Alternatively, the transition metal complex may be reacted with a neutral NCA precursor, such as $B(C_6F_5)_3$, which abstracts an anionic group from the complex to form an activated species. Useful activators include N,N-dimethylanilinium tetrakis(pentafluorophenyl)borate (i.e., $[PhNMe_2H]B(C_6F_5)_4$) and N,N-dimethylanilinium tetrakis(heptafluoronaphthyl) borate, where Ph is phenyl, and Me is methyl.

Additionally preferred activators useful herein include those described in U.S. Pat. No. 7,247,687 at column 169, line 50 to column 174, line 43, particularly column 172, line 24 to column 173, line 53.

In an embodiment of the invention described herein, the non-coordinating anion activator is represented by the following formula (1):

$$(Z)^{d+}(A^{d-}) \qquad (1)$$

wherein Z is (L-H) or a reducible Lewis acid, L is a neutral Lewis base, H is hydrogen and $(L-H)^+$ is a Bronsted acid; $A^{d-}$ is a non-coordinating anion having the charge d–; and d is an integer from 1 to 3.

When Z is (L-H) such that the cation component is $(L-H)^{d+}$, the cation component may include Bronsted acids such as protonated Lewis bases capable of protonating a moiety, such as an alkyl or aryl, from the catalyst precursor, resulting in a cationic transition metal species, or the activating cation $(L-H)^{d+}$ is a Bronsted acid, capable of donating a proton to the catalyst precursor resulting in a transition metal cation, including ammoniums, oxoniums, phosphoniums, silyliums, and mixtures thereof, or ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxoniums from ethers, such as dimethyl ether diethyl ether, tetrahydrofuran, and dioxane, sulfoniums from thioethers, such as diethyl thioethers and tetrahydrothiophene, and mixtures thereof.

When Z is a reducible Lewis acid, it may be represented by the formula: $(Ar_3C+)$, where Ar is aryl or aryl substituted with a heteroatom, or a $C_1$ to $C_{40}$ hydrocarbyl, the reducible Lewis acid may be represented by the formula: $(Ph_3C+)$, where Ph is phenyl or phenyl substituted with a heteroatom, and/or a $C_1$ to $C_{40}$ hydrocarbyl. In an embodiment, the reducible Lewis acid is triphenyl carbenium.

Embodiments of the anion component $A^{d-}$ include those having the formula $[M^k+Q^n]^{d-}$ wherein k is 1, 2, or 3; n is 1, 2, 3, 4, 5 or 6, or 3, 4, 5 or 6; n–k=d; M is an element selected from Group 13 of the Periodic Table of the Elements, or boron or aluminum, and Q is independently a hydride, bridged or unbridged dialkylamido, halide, alkoxide, aryloxide, hydrocarbyl radicals, said Q having up to 20 carbon atoms with the proviso that in not more than one occurrence is Q a halide, and two Q groups may form a ring structure. Each Q may be a fluorinated hydrocarbyl radical having 1 to 20 carbon atoms, or each Q is a fluorinated aryl radical, or each Q is a pentafluoryl aryl radical. Examples of suitable Ad– components also include diboron compounds as disclosed in U.S. Pat. No. 5,447,895, which is fully incorporated herein by reference.

In an embodiment in any of the NCA's represented by Formula 1 described above, the anion component Ad– is represented by the formula $[M*k*+Q*n*]d*-$ wherein k* is 1, 2, or 3; n* is 1, 2, 3, 4, 5, or 6 (or 1, 2, 3, or 4); n*–k*=d*; M* is boron; and Q* is independently selected from hydride, bridged or unbridged dialkylamido, halogen, alkoxide, aryloxide, hydrocarbyl radicals, said Q* having up to 20 carbon atoms with the proviso that in not more than 1 occurrence is Q* a halogen.

This invention also relates to a method to polymerize olefins comprising contacting olefins (such as propylene) with a catalyst complex as described above and an NCA activator represented by the Formula (2):

$$R_nM**(ArNHal)^{4-n} \qquad (2)$$

where R is a monoanionic ligand; M** is a Group 13 metal or metalloid; ArNHal is a halogenated, nitrogen-containing aromatic ring, polycyclic aromatic ring, or aromatic ring assembly in which two or more rings (or fused ring systems) are joined directly to one another or together; and n is 0, 1, 2, or 3. Typically the NCA comprising an anion of Formula 2 also comprises a suitable cation that is essentially non-interfering with the ionic catalyst complexes formed with the transition metal compounds, or the cation is Zd+ as described above.

In an embodiment in any of the NCA's comprising an anion represented by Formula 2 described above, R is selected from the group consisting of $C_1$ to $C_{30}$ hydrocarbyl radicals. In an embodiment, $C_1$ to $C_{30}$ hydrocarbyl radicals may be substituted with one or more $C_1$ to $C_{20}$ hydrocarbyl radicals, halide, hydrocarbyl substituted organometalloid, dialkylamido, alkoxy, aryloxy, alkysulfido, arylsulfido, alkylphosphido, arylphosphide, or other anionic substituent; fluoride; bulky alkoxides, where bulky means $C_4$ to $C_{20}$ hydrocarbyl radicals; —SRa, —NRa₂, and —PRa₂, where each Ra is independently a monovalent C$_4$ to C$_{20}$ hydrocarbyl radical comprising a molecular volume greater than or equal to the molecular volume of an isopropyl substitution or a C$_4$ to C$_{20}$ hydrocarbyl substituted organometalloid having a molecular volume greater than or equal to the molecular volume of an isopropyl substitution.

In an embodiment in any of the NCA's comprising an anion represented by Formula 2 described above, the NCA also comprises cation comprising a reducible Lewis acid represented by the formula: (Ar$_3$C+), where Ar is aryl or aryl substituted with a heteroatom, and/or a C$_1$ to C$_{40}$ hydrocarbyl, or the reducible Lewis acid represented by the formula: (Ph$_3$C+), where Ph is phenyl or phenyl substituted with one or more heteroatoms, and/or C$_1$ to C$_{40}$ hydrocarbyls.

In an embodiment in any of the NCA's comprising an anion represented by Formula 2 described above, the NCA may also comprise a cation represented by the formula, (L-H)$^{d+}$, wherein L is an neutral Lewis base; H is hydrogen; (L-H) is a Bronsted acid; and d is 1, 2, or 3, or (L-H)$^{d+}$ is a Bronsted acid selected from ammoniums, oxoniums, phosphoniums, silyliums, and mixtures thereof.

Further examples of useful activators include those disclosed in U.S. Pat. Nos. 7,297,653 and 7,799,879, which are fully incorporated by reference herein.

In an embodiment, an activator useful herein comprises a salt of a cationic oxidizing agent and a noncoordinating, compatible anion represented by the Formula (3):

$$(OX^{e+})_d(A^{d-})_e \qquad (3)$$

wherein OX$^{e+}$ is a cationic oxidizing agent having a charge of e+; e is 1, 2 or 3; d is 1, 2 or 3; and A$^{d-}$ is a non-coordinating anion having the charge of d− (as further described above). Examples of cationic oxidizing agents include: ferrocenium, hydrocarbyl-substituted ferrocenium, Ag$^+$, or Pb$^{+2}$. Suitable embodiments of Ad− include tetrakis(pentafluorophenyl)borate.

Activators useful in catalyst systems herein include: trimethylammonium tetrakis(perfluoronaphthyl)borate, N,N-dimethylanilinium tetrakis(perfluoronaphthyl)borate, N,N-diethylanilinium tetrakis(perfluoronaphthyl)borate, triphenylcarbenium tetrakis(perfluoronaphthyl)borate, trimethylammonium tetrakis(perfluorobiphenyl)borate, N,N-dimethylanilinium tetrakis(perfluorobiphenyl)borate, triphenylcarbenium tetrakis(perfluorobiphenyl)borate, and the types disclosed in U.S. Pat. No. 7,297,653, which is fully incorporated by reference herein.

Suitable activators also include: N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, triphenylcarbenium tetrakis(perfluorophenyl)borate, [Ph$_3$C$^+$][B(C$_6$F$_5$)$_4^-$], [Me$_3$NH$^+$][B(C$_6$F$_5$)$_4^-$]; 1-(4-(tris(pentafluorophenyl)borate)-2,3,5,6-tetrafluorophenyl)pyrrolidinium; and tetrakis(pentafluorophenyl)borate, 4-(tris(pentafluorophenyl)borate)-2,3,5,6-tetrafluoropyridine.

In an embodiment, the activator comprises a triaryl carbonium (such as triphenylcarbenium tetraphenylborate, triphenylcarbenium tetrakis(pentafluorophenyl)borate, triphenylcarbenium tetrakis-(2,3,4,6-tetrafluorophenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate).

In an embodiment, two NCA activators may be used in the polymerization and the molar ratio of the first NCA activator to the second NCA activator can be any ratio. In an embodiment, the molar ratio of the first NCA activator to the second NCA activator is 0.01:1 to 10,000:1, or 0.1:1 to 1000:1, or 1:1 to 100:1.

In an embodiment of the invention, the NCA activator-to-catalyst ratio is a 1:1 molar ratio, or 0.1:1 to 100:1, or 0.5:1 to 200:1, or 1:1 to 500:1 or 1:1 to 1000:1. In an embodiment, the NCA activator-to-catalyst ratio is 0.5:1 to 10:1, or 1:1 to 5:1.

In an embodiment, the catalyst compounds can be combined with combinations of alumoxanes and NCA's (see for example, U.S. Pat. No. 5,153,157, U.S. Pat. No. 5,453,410, EP 0 573 120 B 1, WO 94/07928, and WO 95/14044 which discuss the use of an alumoxane in combination with an ionizing activator, all of which are incorporated by reference herein).

In a preferred embodiment of the invention, when an NCA (such as an ionic or neutral stoichiometric activator) is used, the complex-to-activator molar ratio is typically from 1:10 to 1:1; 1:10 to 10:1; 1:10 to 2:1; 1:10 to 3:1; 1:10 to 5:1; 1:2 to 1.2:1; 1:2 to 10:1; 1:2 to 2:1; 1:2 to 3:1; 1:2 to 5:1; 1:3 to 1.2:1; 1:3 to 10:1; 1:3 to 2:1; 1:3 to 3:1; 1:3 to 5:1; 1:5 to 1:1; 1:5 to 10:1; 1:5 to 2:1; 1:5 to 3:1; 1:5 to 5:1; 1:1 to 1:1.2.

Alternately a co-activator, such as a group 1, 2, or 13 organometallic species (e.g., an alkyl aluminum compound such as tri-n-octyl aluminum), may also be used in the catalyst system herein. The complex-to-co-activator molar ratio is from 1:100 to 100:1; 1:75 to 75:1; 1:50 to 50:1; 1:25 to 25:1; 1:15 to 15:1; 1:10 to 10:1; 1:5 to 5:1; 1:2 to 2:1; 1:100 to 1:1; 1:75 to 1:1; 1:50 to 1:1; 1:25 to 1:1; 1:15 to 1:1; 1:10 to 1:1; 1:5 to 1:1; 1:2 to 1:1; 1:10 to 2:1.

Optional Support Materials

In embodiments herein, the catalyst system may comprise an inert support material. Preferably the supported material is a porous support material, for example, talc, and inorganic oxides. Other support materials include zeolites, clays, organoclays, or any other organic or inorganic support material and the like, or mixtures thereof.

Preferably, the support material is an inorganic oxide in a finely divided form. Suitable inorganic oxide materials for use in metallocene catalyst systems herein include Groups 2, 4, 13, and 14 metal oxides, such as silica, alumina, and mixtures thereof. Other inorganic oxides that may be employed either alone or in combination with the silica, or alumina are magnesia, titania, zirconia, and the like. Other suitable support materials, however, can be employed, for example, finely divided functionalized polyolefins, such as finely divided polyethylene. Particularly useful supports include magnesia, titania, zirconia, montmorillonite, phyllosilicate, zeolites, talc, clays, and the like. Also, combinations of these support materials may be used, for example, silica-chromium, silica-alumina, silica-titania, and the like. Preferred support materials include Al$_2$O$_3$, ZrO$_2$, SiO$_2$, and combinations thereof, more preferably SiO$_2$, Al$_2$O$_3$, or SiO$_2$/Al$_2$O$_3$.

It is preferred that the support material, most preferably an inorganic oxide, has a surface area in the range of from about 10 to about 700 m2/g, pore volume in the range of from about 0.1 to about 4.0 cc/g and average particle size in the range of from about 5 to about 500 μm. More preferably, the surface area of the support material is in the range of from about 50 to about 500 m2/g, pore volume of from about 0.5 to about 3.5 cc/g and average particle size of from about 10 to about 200 μm. Most preferably the surface area of the support material is in the range is from about 100 to about 400 m2/g, pore volume from about 0.8 to about 3.0 cc/g and average particle size is from about 5 to about 100 μm. The average pore size of the support material useful in the invention is in the range of from 10 to 1000 Å, preferably 50 to about 500 Å, and most preferably 75 to about 350 Å. In some embodiments, the support material is a high surface area, amorphous silica (surface area=300 m2/gm; pore volume of 1.65 cm3/gm). Preferred silicas are marketed under the tradenames of Davison 952 or Davison 955 by the Davison Chemical Division of W.R. Grace and Company. In other embodiments DAVISON 948 is used.

The support material should be dry, that is, free of absorbed water. Drying of the support material can be effected by heating or calcining at about 100° C. to about 1000° C., preferably at least about 600° C. When the support material is silica, it is heated to at least 200° C., preferably about 200° C. to about 850° C., and most preferably at about 600° C.; and for a time of about 1 minute to about 100 hours, from about 12 hours to about 72 hours, or from about 24 hours to about 60 hours. The calcined support material must have at least some reactive hydroxyl (OH) groups to produce supported catalyst systems of this invention. The calcined support material is then contacted with at least one polymerization catalyst comprising at least one metallocene compound and an activator.

The support material, having reactive surface groups, typically hydroxyl groups, is slurried in a non-polar solvent and the resulting slurry is contacted with a solution of a metallocene compound and an activator. In some embodiments, the slurry of the support material is first contacted with the activator for a period of time in the range of from about 0.5 hours to about 24 hours, from about 2 hours to about 16 hours, or from about 4 hours to about 8 hours. The solution of the metallocene compound is then contacted with the isolated support/activator. In some embodiments, the supported catalyst system is generated in situ. In alternate embodiment, the slurry of the support material is first contacted with the catalyst compound for a period of time in the range of from about 0.5 hours to about 24 hours, from about 2 hours to about 16 hours, or from about 4 hours to about 8 hours. The slurry of the supported metallocene compound is then contacted with the activator solution.

The mixture of the metallocene, activator and support is heated to about 0° C. to about 70° C., preferably to about 23° C. to about 60° C., preferably at room temperature. Contact times typically range from about 0.5 hours to about 24 hours, from about 2 hours to about 16 hours, or from about 4 hours to about 8 hours.

Suitable non-polar solvents are materials in which all of the reactants used herein, i.e., the activator, and the metallocene compound, are at least partially soluble and which are liquid at reaction temperatures. Preferred non-polar solvents are alkanes, such as isopentane, hexane, n-heptane, octane, nonane, and decane, although a variety of other materials including cycloalkanes, such as cyclohexane, aromatics, such as benzene, toluene, and ethylbenzene, may also be employed.

Polymerization Processes

In embodiments herein, the invention relates to polymerization processes where monomer (such as propylene), and optionally comonomer, are contacted with a catalyst system comprising an activator and at least one metallocene compound, as described above. The catalyst compound and activator may be combined in any order, and are combined typically prior to contacting with the monomer.

Monomers useful herein include substituted or unsubstituted $C_2$ to $C_{40}$ alpha olefins, preferably $C_2$ to $C_{20}$ alpha olefins, preferably $C_2$ to $C_{12}$ alpha olefins, preferably ethylene, propylene, butene, pentene, hexene, heptene, octene, nonene, decene, undecene, dodecene and isomers thereof. In a preferred embodiment of the invention, the monomer comprises propylene and an optional comonomers comprising one or more ethylene or $C_4$ to $C_{40}$ olefins, preferably $C_4$ to $C_{20}$ olefins, or preferably $C_6$ to $C_{12}$ olefins. The $C_4$ to $C_{40}$ olefin monomers may be linear, branched, or cyclic. The $C_4$ to $C_{40}$ cyclic olefins may be strained or unstrained, monocyclic or polycyclic, and may optionally include heteroatoms and/or one or more functional groups. In another preferred embodiment, the monomer comprises ethylene and an optional comonomers comprising one or more $C_3$ to $C_{40}$ olefins, preferably $C_4$ to $C_{20}$ olefins, or preferably $C_6$ to $C_{12}$ olefins. The $C_3$ to $C_{40}$ olefin monomers may be linear, branched, or cyclic. The $C_3$ to $C_{40}$ cyclic olefins may be strained or unstrained, monocyclic or polycyclic, and may optionally include heteroatoms and/or one or more functional groups.

Exemplary $C_2$ to $C_{40}$ olefin monomers and optional comonomers include ethylene, propylene, butene, pentene, hexene, heptene, octene, nonene, decene, undecene, dodecene, norbornene, norbornadiene, dicyclopentadiene, cyclopentene, cycloheptene, cyclooctene, cyclooctadiene, cyclododecene, 7-oxanorbornene, 7-oxanorbornadiene, substituted derivatives thereof, and isomers thereof, preferably hexene, heptene, octene, nonene, decene, dodecene, cyclooctene, 1,5-cyclooctadiene, 1-hydroxy-4-cyclooctene, 1-acetoxy-4-cyclooctene, 5-methylcyclopentene, cyclopentene, dicyclopentadiene, norbornene, norbornadiene, and their respective homologs and derivatives, preferably norbornene, norbornadiene, and dicyclopentadiene.

In a preferred embodiment one or more dienes are present in the polymer produced herein at up to 10 weight %, preferably at 0.00001 to 1.0 weight %, preferably 0.002 to 0.5 weight %, even more preferably 0.003 to 0.2 weight %, based upon the total weight of the composition. In some embodiments 500 ppm or less of diene is added to the polymerization, preferably 400 ppm or less, preferably or 300 ppm or less. In other embodiments at least 50 ppm of diene is added to the polymerization, or 100 ppm or more, or 150 ppm or more.

Preferred diolefin monomers useful in this invention include any hydrocarbon structure, preferably $C_4$ to $C_{30}$, having at least two unsaturated bonds, wherein at least two of the unsaturated bonds are readily incorporated into a polymer by either a stereospecific or a non-stereospecific catalyst(s). It is further preferred that the diolefin monomers be selected from alpha, omega-diene monomers (i.e. di-vinyl monomers). More preferably, the diolefin monomers are linear di-vinyl monomers, most preferably those containing from 4 to 30 carbon atoms. Examples of preferred dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, particularly preferred dienes include 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1000 g/mol). Preferred cyclic dienes include cyclopentadiene, vinylnorbornene, norbornadiene, ethylidene norbornene, divinylbenzene, dicyclopentadiene or higher ring containing diolefins with or without substituents at various ring positions.

In some embodiments, where butene is the comonomer, the butene source may be a mixed butene stream comprising various isomers of butene. The 1-butene monomers are expected to be preferentially consumed by the polymerization process. Use of such mixed butene streams will provide an economic benefit, as these mixed streams are often waste streams from refining processes, for example, $C_4$ raffinate streams, and can therefore be substantially less expensive than pure 1-butene.

Polymerization processes of this invention can be carried out in any manner known in the art. Any suspension, homogeneous, bulk, solution, slurry, or gas phase polymerization process known in the art can be used. Such processes can be run in a batch, semi-batch, or continuous mode. Homogeneous polymerization processes and slurry processes are preferred. (A homogeneous polymerization process is defined to be a process where at least 90 wt % of the product is soluble in the reaction media.) A bulk homogeneous process is particularly preferred. (A bulk process is defined to be a process where monomer concentration in all feeds to the reactor is 70 volume % or more.) Alternately, no solvent or diluent is present or added in the reaction medium, (except for the small amounts used as the carrier for the catalyst system or other additives, or amounts typically found with the monomer; e.g., propane in propylene). In another embodiment, the process is a slurry process. As used herein the term "slurry polymerization process" means a polymerization process where a supported catalyst is employed and monomers are polymerized on the supported catalyst particles. At least 95 wt % of polymer products derived from the supported catalyst are in granular form as solid particles (not dissolved in the diluent).

Suitable diluents/solvents for polymerization include non-coordinating, inert liquids. Examples include straight and branched-chain hydrocarbons, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof, such as can be found commercially (Isopar™); perhalogenated hydrocarbons, such as perfluorinated $C_4$-$C_{10}$ alkanes, chlorobenzene, and aromatic and alkylsubstituted aromatic compounds, such as benzene, toluene, mesitylene, and xylene. Suitable solvents also include liquid olefins which may act as monomers or comonomers including ethylene, propylene, 1-butene, 1-hexene, 1-pentene, 3-methyl-1-pentene, 4-methyl-1-pentene, 1-octene, 1-decene, and mixtures thereof. In a preferred embodiment, aliphatic hydrocarbon solvents are used as the solvent, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof. In another embodiment, the solvent is not aromatic, preferably aromatics are present in the solvent at less than 1 wt %, preferably less than 0.5 wt %, preferably less than 0 wt % based upon the weight of the solvents.

In a preferred embodiment, the feed concentration of the monomers and comonomers for the polymerization is 60 vol % solvent or less, preferably 40 vol % or less, or preferably 20 vol % or less, based on the total volume of the feedstream. Preferably the polymerization is run in a bulk process.

Preferred polymerizations can be run at any temperature and/or pressure suitable to obtain the desired ethylene polymers. Typical temperatures and/or pressures include a temperature in the range of from about 0° C. to about 300° C., preferably about 20° C. to about 200° C., preferably about 35° C. to about 150° C., preferably from about 40° C. to about 120° C., preferably from about 45° C. to about 80° C.; and at a pressure in the range of from about 0.35 MPa to about 10 MPa, preferably from about 0.45 MPa to about 6 MPa, or preferably from about 0.5 MPa to about 4 MPa.

In a typical polymerization, the run time of the reaction is up to 300 minutes, preferably in the range of from about 5 to 250 minutes, or preferably from about 10 to 120 minutes.

In a some embodiments hydrogen is present in the polymerization reactor at a partial pressure of 0.001 to 50 psig (0.007 to 345 kPa), preferably from 0.01 to 25 psig (0.07 to 172 kPa), more preferably 0.1 to 10 psig (0.7 to 70 kPa).

In an alternate embodiment, the activity of the catalyst is at least 50 g/mmol/hour, preferably 500 or more g/mmol/hour, preferably 5000 or more g/mmol/hr, preferably 50,000 or more g/mmol/hr. In an alternate embodiment, the conversion of olefin monomer is at least 10%, based upon polymer yield and the weight of the monomer entering the reaction zone, preferably 20% or more, preferably 30% or more, preferably 50% or more, preferably 80% or more. In particular embodiments, the catalyst has an activity of 150,000 to about 320,000 g/mmol/hour, particularly and is capable of producing a polypropylene having a Tm of 158° C. to 162° C., e.g., 158.5° C., 159.0° C., 159.5° C., 160.0° C., 160.5° C., 161.0° C., 161.5° C., or 162.0° C.)

In a preferred embodiment, little or no alumoxane is used in the process to produce the polymers. Preferably, alumoxane is present at zero mol %, alternately the alumoxane is present at a molar ratio of aluminum to transition metal less than 500:1, preferably less than 300:1, preferably less than 100:1, preferably less than 1:1.

In a preferred embodiment, little or no scavenger is used in the process to produce the ethylene polymer. Preferably, scavenger (such as tri alkyl aluminum) is present at zero mol %, alternately the scavenger is present at a molar ratio of scavenger metal to transition metal of less than 100:1, preferably less than 50:1, preferably less than 15:1, preferably less than 10:1.

In a preferred embodiment, the polymerization: 1) is conducted at temperatures of 0 to 300° C. (preferably 25 to 150° C., preferably 40 to 120° C., preferably 45 to 80° C.); 2) is conducted at a pressure of atmospheric pressure to 10 MPa (preferably 0.35 to 10 MPa, preferably from 0.45 to 6 MPa, preferably from 0.5 to 4 MPa); 3) is conducted in an aliphatic hydrocarbon solvent (such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof; preferably where aromatics are preferably present in the solvent at less than 1 wt %, preferably less than 0.5 wt %, preferably at 0 wt % based upon the weight of the solvents); and 4) the productivity of the catalyst compound is at least 80,000 g/mmol/hr (preferably at least 150,000 g/mmol/hr, preferably at least 200,000 g/mmol/hr, preferably at least 250,000 g/mmol/hr, preferably at least 300,000 g/mmol/hr). In a preferred embodiment, the catalyst system used in the polymerization comprises no more than one catalyst compound. A "reaction zone" also referred to as a "polymerization zone" is a vessel where polymerization takes place, for example a batch reactor. When multiple reactors are used in either series or parallel configuration, each reactor is considered as a separate polymerization zone. For a multi-stage polymerization in both a batch reactor and a continuous reactor, each polymerization stage is considered as a separate polymerization zone. In a preferred embodiment, the polymerization occurs in one reaction zone. Room temperature is 23° C. unless otherwise noted.

Other additives may also be used in the polymerization, as desired, such as one or more scavengers, promoters, modifiers, chain transfer agents (such as diethyl zinc), reducing agents, oxidizing agents, hydrogen, aluminum alkyls, or silanes.

Useful chain transfer agents are typically alkylalumoxanes, a compound represented by the formula $AlR_3$, $ZnR_2$ (where each R is, independently, a $C_1$-$C_8$ aliphatic radical, preferably methyl, ethyl, propyl, butyl, phenyl, hexyl octyl or an isomer thereof) or a combination thereof, such as diethyl zinc, methylalumoxane, trimethylaluminum, tri-isobutylaluminum, trioctylaluminum, or a combination thereof.

Polyolefin Products

This invention also relates to compositions of matter produced by the methods described herein.

In a preferred embodiment, the process described herein produces propylene homopolymers or propylene copolymers, such as propylene-ethylene and/or propylene-alphaolefin (preferably $C_3$ to $C_{20}$) copolymers (such as propylene-hexene copolymers or propylene-octene copolymers) having an Mw/Mn of greater than 1 to 4 (preferably greater than 1 to 3).

Likewise, the process of this invention produces olefin polymers, preferably polyethylene and polypropylene homopolymers and copolymers. In a preferred embodiment, the polymers produced herein are homopolymers of ethylene or propylene, are copolymers of ethylene preferably having from 0 to 25 mole % (alternately from 0.5 to 20 mole %, alternately from 1 to 15 mole %, preferably from 3 to 10 mole %) of one or more $C_3$ to $C_{20}$ olefin comonomer (preferably $C_3$ to $C_{12}$ alpha-olefin, preferably propylene, butene, hexene, octene, decene, dodecene, preferably propylene, butene, hexene, octene), or are copolymers of propylene preferably having from 0 to 25 mole % (alternately from 0.5 to 20 mole %, alternately from 1 to 15 mole %, preferably from 3 to 10 mole %) of one or more of $C_2$ or $C_4$ to $C_{20}$ olefin comonomer (preferably ethylene or $C_4$ to $C_{12}$ alpha-olefin, preferably ethylene, butene, hexene, octene, decene, dodecene, preferably ethylene, butene, hexene, octene).

In a preferred embodiment, the monomer is propylene and the comonomer is hexene, preferably from 1 to 15 mole % hexene, alternately 1 to 10 mole %.

Typically, the polymers produced herein have an Mw of 5,000 to 1,000,000 g/mol (preferably 25,000 to 750,000 g/mol, preferably 50,000 to 500,000 g/mol), and/or an Mw/Mn of greater than 1 to 40 (alternately 1.2 to 20, alternately 1.3 to 10, alternately 1.4 to 5, 1.5 to 4, alternately 1.5 to 3).

In a preferred embodiment the polymer produced herein has a unimodal or multimodal molecular weight distribution as determined by Gel Permeation Chromatography (GPC). By "unimodal" is meant that the GPC trace has one peak or inflection point. By "multimodal" is meant that the GPC trace has at least two peaks or inflection points. An inflection point is that point where the second derivative of the curve changes in sign (e.g., from negative to positive or vice versus).

In a preferred embodiment the polymer produced herein has a composition distribution breadth index (CDBI) of 50% or more, preferably 60% or more, preferably 70% or more. CDBI is a measure of the composition distribution of the monomer within the polymer chains and is measured by the procedure described in PCT publication WO 93/03093, published Feb. 18, 1993, specifically columns 7 and 8 as well as in Wild et al, J. Poly. Sci., Poly. Phys. Ed., Vol. 20, p. 441 (1982) and U.S. Pat. No. 5,008,204, including that fractions having a weight average molecular weight (Mw) below 15,000 are ignored when determining CDBI.

In another embodiment, the polymers produced herein using catalyst compound where both R10 groups are the same or different groups and are represented by the formula: $(XR'_n)^-$, wherein X is a Group 14, 15, 16 or 17 heteroatom having an atomic weight of 13 to 79 and R' is one of a hydrogen atom, halogen atom, a $C_1$-$C_{10}$ alkyl group, or a $C_6$-$C_{10}$ aryl group and n is 0, 1, 2 or 3, have at least 20% higher Mw (alternately at least 30%, alternately at least 40%) as compared to the polymer produced by the same catalyst compound, except that both R10 groups are hydrogen, combined with the same activator and polymerized under the same conditions with the same monomers (such as ethylene and propylene). In a useful embodiment, each R10 is independently $-NR'_2$, $-SR'$, $-OR'$, $-OSiR'_3$, $-SiR'_3$, or $-PR'_2$, more particularly $R^{10}$ is selected from $-NR'_2$, $-SR'$, $-OR'$, $-OSiR'_3$, or $-PR'_2$, preferably $-OR'$; wherein R' is a $C_1$-$C_{10}$ alkyl group, particularly each R10 is a methoxy, ethoxy, n-propoxy, isopropoxy, n-butoxy, iso-butoxy, sec-butoxy, or t-butoxy group, most particularly methoxy.

In another embodiment, the polymers comprising ethylene and propylene produced herein using catalyst compound where both R10 groups are the same or different groups and are represented by the formula: OR', where R' is a $C_1$-$C_{10}$ alkyl group, have at least 20% higher Mw (alternately at least 30%, alternately at least 40%) as compared to the polymer produced by the same catalyst compound, except that both R10 groups are hydrogen, combined with the same activator and polymerized under the same conditions with the same monomers. In a useful embodiment, each R10 is independently a methoxy, ethoxy, n-propoxy, isopropoxy, n-butoxy, iso-butoxy, sec-butoxy, or t-butoxy group, usefully both R10 are methoxy.

In a particularly useful embodiment, ethylene propylene copolymer produced herein using catalyst compound where both R10 groups are methoxy, has at least 20% higher Mw (alternately at least 30%, alternately at least 40%) as compared to the polymer produced by the same catalyst compound, except that both R10 groups are hydrogen, combined with the same activator and polymerized under the same conditions with the same monomers.

Blends

In another embodiment, the polymer (preferably the polyethylene or polypropylene) produced herein is combined with one or more additional polymers prior to being formed into a film, molded part or other article. Other useful polymers include polyethylene, isotactic polypropylene, highly isotactic polypropylene, syndiotactic polypropylene, random copolymer of propylene and ethylene, and/or butene, and/or hexene, polybutene, ethylene vinyl acetate, LDPE, LLDPE, HDPE, ethylene vinyl acetate, ethylene methyl acrylate, copolymers of acrylic acid, polymethylmethacrylate or any other polymers polymerizable by a high-pressure free radical process, polyvinylchloride, polybutene-1, isotactic polybutene, ABS resins, ethylene-propylene rubber (EPR), vulcanized EPR, EPDM, block copolymer, styrenic block copolymers, polyamides, polycarbonates, PET resins, cross linked polyethylene, copolymers of ethylene and vinyl alcohol (EVOH), polymers of aromatic monomers such as polystyrene, poly-1 esters, polyacetal, polyvinylidine fluoride, polyethylene glycols, and/or polyisobutylene.

In a preferred embodiment, the polymer (preferably the polyethylene or polypropylene) is present in the above blends, at from 10 to 99 wt %, based upon the weight of the polymers in the blend, preferably 20 to 95 wt %, even more preferably at least 30 to 90 wt %, even more preferably at least 40 to 90 wt %, even more preferably at least 50 to 90 wt %, even more preferably at least 60 to 90 wt %, even more preferably at least 70 to 90 wt %.

The blends described above may be produced by mixing the polymers of the invention with one or more polymers (as described above), by connecting reactors together in series to make reactor blends or by using more than one catalyst in the same reactor to produce multiple species of polymer. The polymers can be mixed together prior to being put into the extruder or may be mixed in an extruder.

The blends may be formed using conventional equipment and methods, such as by dry blending the individual components and subsequently melt mixing in a mixer, or by mixing the components together directly in a mixer, such as, for example, a Banbury mixer, a Haake mixer, a Brabender internal mixer, or a single or twin-screw extruder, which may include a compounding extruder and a side-arm extruder used directly downstream of a polymerization process, which may include blending powders or pellets of the resins at the hopper of the film extruder. Additionally, additives may be included in the blend, in one or more components of the blend, and/or in a product formed from the blend, such as a film, as desired. Such additives are well known in the art, and can include, for example: fillers; antioxidants (e.g., hindered phenolics such as IRGANOX™ 1010 or IRGANOX™ 1076 available from Ciba-Geigy); phosphites (e.g., IRGAFOS™ 168 available from Ciba-Geigy); anti-cling additives; tackifiers, such as polybutenes, terpene resins, aliphatic and aromatic hydrocarbon resins, alkali metal and glycerol stearates, and hydrogenated rosins; UV stabilizers; heat stabilizers; anti-blocking agents; release agents; anti-static agents; pigments; colorants; dyes; waxes; silica; fillers; talc; and the like.

Films

Specifically, any of the foregoing polymers, such as the foregoing polypropylenes or blends thereof, may be used in a variety of end-use applications. Such applications include, for example, mono- or multi-layer blown, extruded, and/or shrink films. These films may be formed by any number of well known extrusion or coextrusion techniques, such as a blown bubble film processing technique, wherein the composition can be extruded in a molten state through an annular die and then expanded to form a uni-axial or biaxial orientation melt prior to being cooled to form a tubular, blown film, which can then be axially slit and unfolded to form a flat film. Films may be subsequently unoriented, uniaxially oriented, or biaxially oriented to the same or different extents. One or more of the layers of the film may be oriented in the transverse and/or longitudinal directions to the same or different extents. The uniaxially orientation can be accomplished using typical cold drawing or hot drawing methods. Biaxial orientation can be accomplished using tenter frame equipment or a double bubble processes and may occur before or after the individual layers are brought together. For example, a polyethylene layer can be extrusion coated or laminated onto an oriented polypropylene layer or the polyethylene and polypropylene can be coextruded together into a film then oriented. Likewise, oriented polypropylene could be laminated to oriented polyethylene or oriented polyethylene could be coated onto polypropylene then optionally the combination could be oriented even further. Typically the films are oriented in the Machine Direction (MD) at a ratio of up to 15, preferably between 5 and 7, and in the Transverse Direction (TD) at a ratio of up to 15, preferably 7 to 9. However, in another embodiment the film is oriented to the same extent in both the MD and TD directions.

The films may vary in thickness depending on the intended application; however, films of a thickness from 1 to 50 μm are usually suitable. Films intended for packaging are usually from 10 to 50 μm thick. The thickness of the sealing layer is typically 0.2 to 50 μm. There may be a sealing layer on both the inner and outer surfaces of the film or the sealing layer may be present on only the inner or the outer surface.

In another embodiment, one or more layers may be modified by corona treatment, electron beam irradiation, gamma irradiation, flame treatment, or microwave. In a preferred embodiment, one or both of the surface layers is modified by corona treatment.

Particular Embodiments

This invention further relates to:

Embodiment A: A transition metal complex represented by the formula (I):

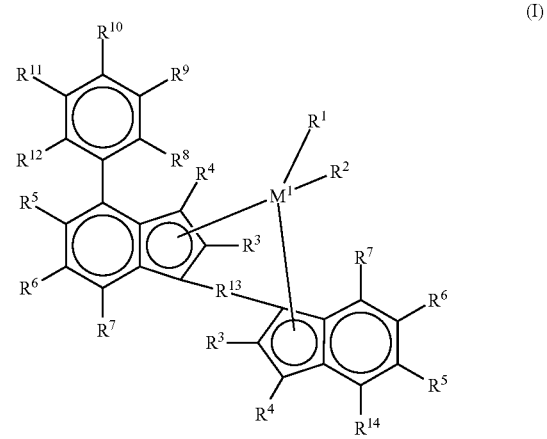

wherein $M^1$ is selected from the group consisting of titanium, zirconium, hafnium, vanadium, niobium, tantalum, chromium, molybdenum and tungsten; $R^1$ and $R^2$ may be identical or different, and are each a hydrogen atom, a $C_1$-$C_{10}$ alkyl group, a $C_1$-$C_{10}$ alkoxy group, a $C_6$-$C_{10}$ aryl group, a $C_6$-$C_{10}$ aryloxy group, a $C_2$-$C_{10}$ alkenyl group, a $C_2$-$C_{40}$ alkenyl group, a $C_7$-$C_{40}$ arylalkyl group, a $C_7$-$C_{40}$ alkylaryl group, a $C_8$-$C_{40}$ arylalkenyl group, an OH group or a halogen atom, or a conjugated diene which is optionally substituted with one or more hydrocarbyl, tri(hydrocarbyl)silyl groups or tri(hydrocarbyl)silylhydrocarbyl groups, said diene having up to 30 atoms not counting hydrogen; $R^3$ to $R^7$ may be identical or different and are each a hydrogen atom, a halogen atom, a $C_1$-$C_{10}$ alkyl group which may be halogenated, a $C_6$-$C_{10}$ aryl group which may be halogenated, a $C_2$-$C_{10}$ alkenyl group, a $C_7$-$C_{40}$ arylalkyl group, a $C_7$-$C_{40}$ alkylaryl group, a $C_8$-$C_{40}$ arylalkenyl group, a-NR'$_2$, —SR', —OR, —OSiR'$_3$ or —PR'$_z$ radical, wherein R' is one of a hydrogen atom, halogen atom, a $C_1$-$C_{10}$ alkyl group, or a $C_6$-$C_{10}$ aryl group or two or more adjacent radicals $R^5$ to $R^7$ together with the atoms of the indenyl group connecting them form one or more rings; $R^{13}$ is —B($R^{15}$)—, —Al($R^{15}$)—, —Ge—, —Sn—, —O—, —S—, —SO—, —SO2-, —N($R^{15}$)—, —CO—, —P($R^{15}$)—, or —P(O)($R^{15}$)—, an amidoborane radical or meets one of the following:

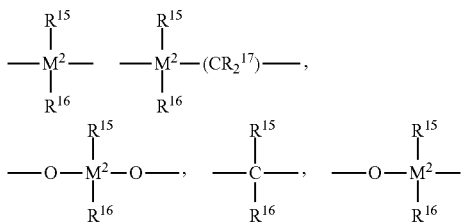

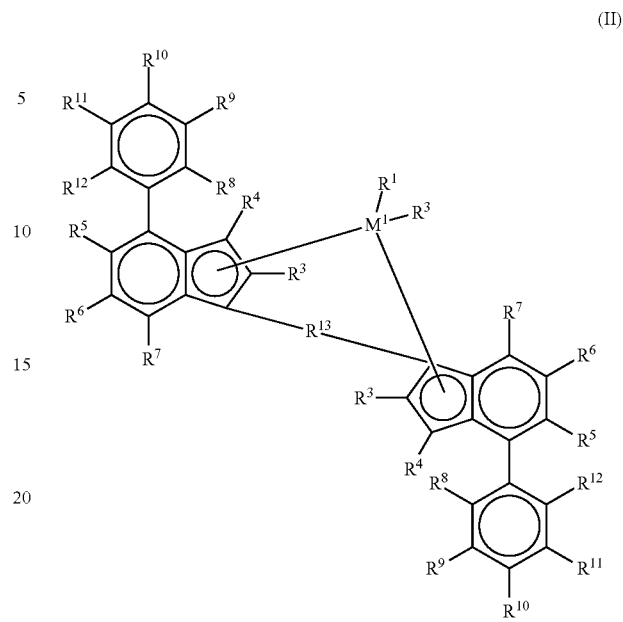

(II)

wherein: $R^{15}$, $R^{16}$, $R^{17}$ are identical or different and are a hydrogen atom, a halogen atom, a $C_1$-$C_{20}$ alkyl group, a $C_1$-$C_{20}$ fluoroalkyl or silaalkyl group, a $C_6$-$C_{30}$ aryl group, a $C_6$-$C_{30}$ fluoroaryl group, a $C_1$-$C_{20}$ alkoxy group, a $C_2$-$C_{20}$ alkenyl group, a $C_7$-$C_{40}$ arylalkyl group, a $C_8$-$C_{40}$ arylalkenyl group, a $C_7$-$C_{40}$ alkylaryl group, or one $R^{15}$ and one $R^{16}$, together with the atoms in $R^{13}$ connecting them, form one or more rings; $M^2$ is one or more carbons, silicon, germanium or tin;

wherein $R^8$, $R^{12}$, and $R^{14}$ may be identical or different and are each a hydrogen atom, a halogen atom, a $C_3$-$C_{10}$ alkyl group which may be halogenated, a $C_6$-$C_{10}$ aryl group which may be halogenated, a $C_2$-$C_{10}$ alkenyl group, a $C_7$-$C_{40}$ arylalkyl group, a $C_7$-$C_{40}$ alkylaryl group, a $C_8$-$C_{40}$ arylalkenyl group, a-$NR'_2$, —$SR'$, —$OR$, —$OSiR'_3$ or —$PR'_2$ radical, wherein $R'$ is one of a hydrogen atom, halogen atom, a $C_1$-$C_{10}$ alkyl group, or a $C_6$-$C_{10}$ aryl group;

wherein $R^9$ and $R^{11}$ are identical or different and selected from $C_2$-$C_{20}$ alkyl group which may be halogenated, a $C_6$-$C_{10}$ aryl group which may be halogenated, a $C_2$-$C_{10}$ alkenyl group, a $C_7$-$C_{20}$ arylalkyl group, a $C_7$-$C_{20}$ alkylaryl group, a $C_8$-$C_{20}$ arylalkenyl group; and wherein $R^{10}$ is selected from $(XR'_n)^-$, wherein X is a Group 14-17 heteroatom having an atomic weight of 13 to 79 and $R'$ is one of a hydrogen atom, a halogen atom, a $C_1$-$C_{10}$ alkyl group, or a $C_6$-$C_{10}$ aryl group and n is an integer of 0-3; particularly wherein $R^{10}$ is —$NR'_2$, —$SR'$, —$OR'$, —$OSiR'_3$, —$SiR'_3$, or —$PR'_2$, wherein $R^{10}$ selected from —$NR'_2$, —$SR'$, —$OR'$, —$OSiR'_3$, or —$PR'_2$, wherein $R^{10}$ is —$SR'$, —$OR'$, or —$OSiR'_3$, wherein $R^{10}$ is —$NR'_2$ or —$PR'_2$ radical, or wherein $R^{10}$ is —$OR'$.

Embodiment B: The transition metal complex of Embodiment A, wherein $R^{14}$ is a substituted or unsubstituted $C_6$-$C_{10}$ aryl group which may be halogenated.

Embodiment C: the transition metal complex of Embodiment A or B, wherein $R^{14}$ is a substituted or unsubstituted phenyl.

Embodiment D: The transition metal complex of any of Embodiments A to C, wherein $R^3$ is a $C_1$-$C_{10}$ alkyl group or a $C_6$-$C_{10}$ aryl group.

Embodiment E: The transition metal complex of any of Embodiments A to D, wherein $R^3$ is methyl.

Embodiment F: The transition metal complex of any of Embodiments A to E, wherein $R^9$ and $R^{11}$ may be the same or different and are each a butyl group, an aryl group, an isopropyl group, or a fluoroalkyl group.

Embodiment G: The transition metal complex of any of Embodiments A to F, wherein $R^9$ and $R^{11}$ are each selected from the group consisting of n-butyl-, iso-butyl-, and tert-butyl groups and $R_{10}$ is $OR'$ wherein $R'$ is a $C_1$-$C_{10}$ alkyl group.

Embodiment H: The transition metal complex of Embodiment A, represented by the formula (II):

wherein each $R^8$ and $R^{12}$ may be identical or different and are each a hydrogen atom, a halogen atom, a $C_3$-$C_{10}$ alkyl group which may be halogenated, a $C_6$-$C_{10}$ aryl group which may be halogenated, a $C_2$-$C_{10}$ alkenyl group, a $C_7$-$C_{40}$ arylalkyl group, a $C_7$-$C_{40}$ alkylaryl group, a $C_8$-$C_{40}$ arylalkenyl group, a-$NR'_2$, —$SR'$, —$OR$, —$OSiR'_3$ or —$PR'_2$ radical, wherein $R'$ is one of a hydrogen atom, halogen atom, a $C_1$-$C_{10}$ alkyl group, or a $C_6$-$C_{10}$ aryl group; wherein each $R^9$ and $R^{11}$ are identical or different and are each a $C_2$-$C_{20}$ alkyl group which may be halogenated, a $C_6$-$C_{10}$ aryl group which may be halogenated, a $C_2$-$C_{10}$ alkenyl group, a $C_7$-$C_{20}$ arylalkyl group, a $C_7$-$C_{20}$ alkylaryl group, or a $C_8$-$C_{20}$ arylalkenyl group; and wherein $R^{10}$ is selected from $(XR'_n)^-$, wherein X is a Group 14-17 heteroatom having an atomic weight of 13 to 79 and $R'$ is one of a hydrogen atom, halogen atom, a $C_1$-$C_{10}$ alkyl group, or a $C_6$-$C_{10}$ aryl group and n is an integer of 0-3; particularly wherein $R^{16}$ is —$NR'_2$, —$SR'$, —$OR'$, —$OSiR'_3$, —$SiR'_3$, or —$PR'_2$, wherein $R^{16}$ is selected from —$NR'_2$, —$SR'$, —$OR'$, —$OSiR'_3$, or —$PR'_2$, wherein $R^{16}$ is —$SR'$, —$OR'$, or —$OSiR'_3$, wherein $R^{16}$ is —$NR'_2$ or —$PR'_2$ radical, or wherein $R^{10}$ is —$OR'$.

Embodiment I: The transition metal complex of Embodiment H, wherein each $R^9$ and each $R^{11}$ is selected from the group consisting of n-butyl-, iso-butyl-, and tert-butyl groups and each $R^{10}$ is $OR'$ wherein $R'$ is a $C_1$-$C_{10}$ alkyl group.

Embodiment J: The transition metal complex of Embodiment H or I, wherein each $R^9$ and each $R^{11}$ is a tert-butyl group and at least one $R^{10}$ is a methoxy group.

Embodiment K: The transition metal complex of any of Embodiments H to J, wherein each $R^3$ may be the same or different and are each a $C_1$-$C_{10}$ alkyl group.

Embodiment L: The transition metal complex of any of Embodiments H to K, wherein each $R^1$ and $R^2$ may be the same or different and are each a halogen atom, preferably Cl; wherein each $R^3$ may be the same or different and are each a $C_1$-$C_{10}$ alkyl group, preferably methyl; wherein each $R^4$, $R^5$, $R^6$, and $R^7$ may be the same or different and are each a hydrogen atom or $C_1$-$C_{10}$ alkyl group, preferably each is a hydrogen atom; wherein each $R^8$ and $R^{12}$ are each a hydrogen atom; $R^{13}$ is —SiR"$_2$— wherein each R" may be the same or different and are each a hydrogen or methyl, preferably methyl; wherein each $R^9$ and $R^{11}$ is a tert-butyl group; and wherein each $R^{10}$ is a methoxy group.

Embodiment M: The transition metal complex of any of Embodiments H to L, wherein $M^1$ is Zr or HE Embodiment N: A transition metal complex represented by the formula (II):

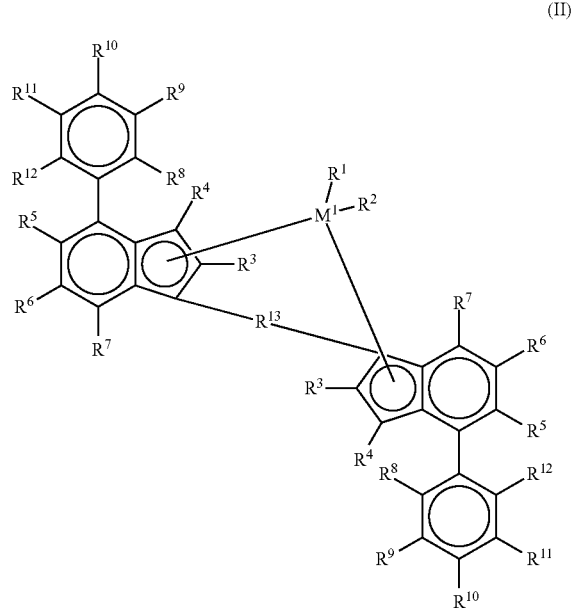

(II)

wherein each $R^1$ and $R^2$ are Cl; each $R^3$ is methyl; each $R^4$, $R^5$, $R^6$, and $R^7$ is a hydrogen atom; each $R^8$ and $R^{12}$ are each a hydrogen atom; $R^{13}$ is —Si(CH$_3$)$_2$—; wherein each $R^9$ and $R^{11}$ is a tert-butyl group; and wherein each $R^{10}$ is a methoxy group.

Embodiment O: A bridged bis(4-phenyl-indenyl) transition metal complex wherein: at least one of the 4-phenyl rings being substituted at the 3' and 5' positions by radicals which may be identical or different and selected from $C_2$-$C_{20}$ alkyl group which may be halogenated, a $C_6$-$C_{10}$ aryl group which may be halogenated, a $C_2$-$C_{10}$ alkenyl group, a $C_7$-$C_{20}$ arylalkyl group, a $C_7$-$C_{20}$ alkylaryl group, a $C_8$-$C_{20}$ arylalkenyl group, wherein at least one of the phenyl rings substituted at the 3' and 5' positions is also substituted at the 4' position with a group selected from (XR'$_n$)$^-$, wherein X is a Group 14-17 heteroatom having an atomic weight of 13 to 79 and R' is one of a hydrogen atom, halogen atom, a $C_1$-$C_{10}$ alkyl group, or a $C_6$-$C_{10}$ aryl group and n is an integer of 0-3; particularly wherein (XR'$_n$)$^-$ is —NR'$_2$, —SR', —OR', —OSiR'$_3$, —SiR'$_3$, or —PR'$_2$, wherein (XR'$_n$)$^-$ is selected from —NR'$_2$, —SR', —OR', —OSiR'$_3$, or —PR'$_2$, wherein (XR'$_n$)$^-$ is —SR', —OR', or —OSiR'$_3$, wherein (XR'$_n$)$^-$ is —NR'$_2$ or —PR'$_2$ radical, or wherein (XR'$_n$)$^-$ is —OR'., wherein R' is one of a hydrogen atom, halogen atom, a $C_1$-$C_{10}$ alkyl group, or a $C_6$-$C_{10}$ aryl group; and optionally, wherein one or more of the remaining positions on the phenyl and/or indenyl ring(s) of the transition metal complex are substituted.

Embodiment P: The transition metal compound of Embodiment O, wherein each of the 4-phenyl rings is substituted at the 3' and 5' positions by radicals which may be identical or different and selected from $C_2$-$C_{20}$ alkyl group which may be halogenated, a $C_6$-$C_{10}$ aryl group which may be halogenated, a $C_2$-$C_{10}$ alkenyl group, a $C_7$-$C_{20}$ arylalkyl group, a $C_7$-$C_{20}$ alkylaryl group, a $C_8$-$C_{20}$ arylalkenyl group.

Embodiment Q: The transition metal complex of Embodiment O or P, wherein: at least one of the 4-pheny-indenyl ligands comprises an $R^3$ group at the 2-position of 4-pheny-indenyl ligand, wherein $R^3$ may be a hydrogen atom, a halogen atom, a $C_1$-$C_{10}$ alkyl group which may be halogenated, a $C_6$-$C_{10}$ aryl group which may be halogenated, a $C_2$-$C_{10}$ alkenyl group, a $C_7$-$C_{40}$ arylalkyl group, a $C_7$-$C_{40}$ alkylaryl group, a $C_8$-$C_{40}$ arylalkenyl group, a-NR'$_2$, —SR', —OR', —OSiR'$_3$ or —PR'$_2$ radical, wherein R is one of a halogen atom, a $C_1$-$C_{10}$ alkyl group, or a $C_6$-$C_{10}$ aryl group.

Embodiment R: The transition metal complex of any of Embodiments O to Q, wherein each of the 4-phenyl-indenyl ligands comprises an $R^3$ substituent at the 2-position of the 4-phenyl-indenyl ligands, wherein $R^3$ may be identical or different and are each a hydrogen atom, halogen atom, a $C_1$-$C_{10}$ alkyl group which may be halogenated, a $C_6$-$C_{10}$ aryl group which may be halogenated, a $C_2$-$C_{10}$ alkenyl group, a $C_7$-$C_{40}$ arylalkyl group, a $C_7$-$C_{40}$ alkylaryl group, a $C_8$-$C_{40}$ arylalkenyl group, a-NR'$_2$, —SR', —OR', —OSiR'$_3$ or —PR'$_2$ radical, wherein R is one of a halogen atom, a $C_1$-$C_{10}$ alkyl group, or a $C_6$-$C_{10}$ aryl group.

Embodiment S: The transition metal complex of any of Embodiments Q to R, with the proviso that when either $R^3$ is a hydrogen atom, a methyl or ethyl group, then both phenyl rings are substituted at the 3' and 5' positions by butyl groups which may be the same or different.

Embodiment T: The transition metal complex of any of Embodiments O to S, wherein at least one 4-phenyl group is substituted at the 3' and 5' position with a tert-butyl group and at the 4' position with a OR' radical, wherein R' is one of a hydrogen atom, halogen atom, a $C_1$-$C_{10}$ alkyl group, or a $C_6$-$C_{10}$ aryl group.

Embodiment U: The transition metal complex of Embodiment T, wherein the OR' radical is a methoxy group.

Embodiment V: The transition metal complex of any of Embodiments O to U, wherein the transition metal is Zr or Hf.

Embodiment W: A catalyst system comprising an activator and the transition metal complex of any of Embodiments A to V.

Embodiment X: The catalyst system of Embodiment W, wherein the activator comprises an alumoxane.

Embodiment Y: The catalyst system of Embodiment W or X, wherein the activator comprises a non-coordinating anion.

Embodiment Z: The catalyst system of any of Embodiments W to Y, wherein the activator comprises one or more of: trimethylammonium tetrakis(perfluoronaphthyl)borate, N,N-dimethylanilinium tetrakis(perfluoronaphthyl)borate, N,N-diethylanilinium tetrakis(perfluoronaphthyl)borate, triphenylcarbenium tetrakis(perfluoronaphthyl)borate, trimethylammonium tetrakis(perfluorobiphenyl)borate, N,N-dimethylanilinium tetrakis(perfluorobiphenyl)borate, triphenylcarbenium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, triphenylcarbenium tetrakis(perfluorophenyl)borate, [Ph$_3$C$^+$][B(C$_6$F$_5$)$_4$$^-$], [Me$_3$NH$^+$][B(C$_6$F$_5$)$_4$$^-$], 1-(4-(tris (pentafluorophenyl)borate)-2,3,5,6-tetrafluorophenyl) pyrrolidinium, tetrakis(pentafluorophenyl)borate, 4-(tris (pentafluorophenyl)borate)-2,3,5,6-tetrafluoropyridine, triphenylcarbenium tetraphenylborate, and triphenylcarbenium tetrakis-(2,3,4,6-tetrafluorophenyl)borate.

Embodiment AA: A polymerization process comprising a) contacting one or more alkene monomers with a catalyst system comprising: i) an activator and ii) the transition metal complex of Any of Embodiments A to V.

Embodiment AB: The process of Embodiment AA, wherein the activator comprises an alumoxane.

Embodiment AC: The process of Embodiment AA, wherein the activator comprises a non-coordinating anion.

Embodiment AD: The process of any of Embodiments AA to AC, wherein the one or more alkene monomers comprises propylene.

Embodiment AE: The process of any of Embodiments AA to AD, wherein the catalyst compound is supported.

Embodiment AF: The process any of Embodiments AA to AE wherein the process occurs at a temperature of from about 0° C. to about 300° C., at a pressure in the range of from about 0.35 MPa to about 10 MPa, and at a time up to 300 minutes.

Embodiment AG: The process of any of Embodiments AA to AF further comprising obtaining polymer.

Embodiment AH: The process of Embodiment AG wherein the polymer comprises a polyprolyene having a melting point>152.0° C., particularly >155.0° C., >158.0° C., >160.0° C., >162.0° C., or >165.0° C. (e.g., 152.0° C. to about 162.0° C.; 155.0° C. to about 162.0° C.; 158.0° C. to about 162.0° C.; or 160.0° C. to about 162.0° C.); $M_w$ 60,000 to 1,400,000 g/mol, particularly 60,000 to 1,200,000 g/mol, particularly, 200,000 to 700,000 g/mol, or 400,000 to 600,000 g/mol; and an MWD of >1.0 to 5, particularly 1.2 to 4.5, particularly 1.5 to 4.0, particularly 1.5 to 3.5, particularly 1.8 to 3.0, particularly 2.0 to 2.5. In some embodiments of the invention, such as when two catalysts are used, the MWD can be >1.0 to 25, particularly 1.2 to 20, particularly 1.5 to 10, particularly 1.5 to 5, particularly 1.8 to 3.0, particularly 2.0 to 2.5.

Experimental $^1$H NMR for Metallocene Characterization: Amounts of rac and meso isomers are determined by proton NMR. $^1$H NMR data are collected at 23° C. in a 5 mm probe using a 400 MHz Bruker spectrometer with deuterated methylene chloride or deuterated benzene. Data is recorded using a maximum pulse width of 45°, 8 seconds between pulses and signal averaging 16 transients. The spectrum is normalized to protonated benzene in the deuterated benzene, which is expected to show a peak at 7.16 ppm.

Catalyst 1 is rac-dimethylsilyl bis(2-methyl-4-(3',5'-di-tert-butyl-4'-methoxy-phenyl)-indenyl)zirconium dichloride.

Catalyst 2 is rac-dimethylsilyl bis(2-methyl-4-phenyl-indenyl)zirconium dichloride.

Catalyst 3 is rac-dimethylsilyl bis(4-(3',5'-di-tert-butyl-phenyl)-2-cyclopropyl-indenyl)zirconium dichloride.

Catalyst 4 is rac-dimethylsilyl bis(4-(3',5'-di-tert-butyl-4'-methoxyphenyl)-2-cyclopropyl-indenyl)zirconium dichloride.

Catalyst 5 is rac-dimethylsilyl (4-o-biphenyl-2-cyclopropyl-indenyl)(2-methyl-4-(3',5'-di-tert-butyl-4'-methoxy-phenyl)-indenyl)zirconium dichloride.

Catalyst 6 is rac-dimethylsilyl (4-o-biphenyl-2-cyclopropyl-indenyl)(4-(3',5'-di-tert-butylphenyl)-2-methyl-indenyl) zirconium dichloride.

Catalyst 7 is rac-dimethylsilyl bis(2-methyl-4-(3',5'-di-tert-butylphenyl)-indenyl)zirconium dichloride.

MAO is methyl alumoxane (30 wt % in toluene) obtained from Albemarle.

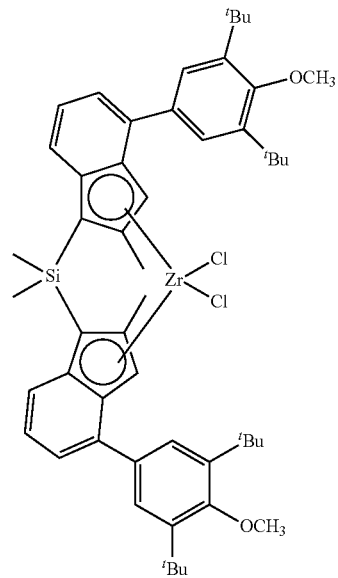

1

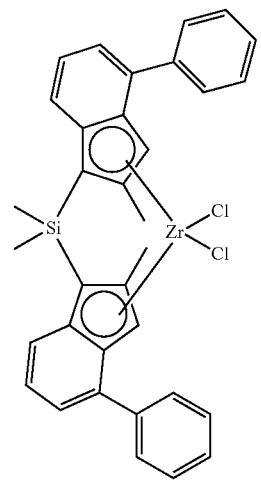

2

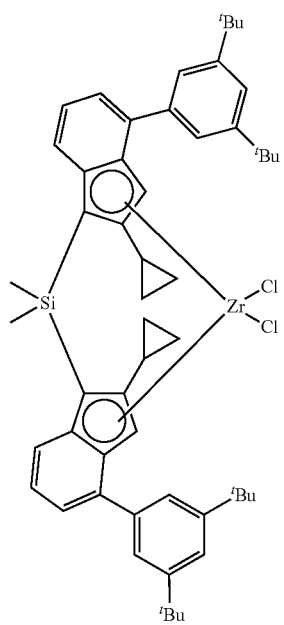

3

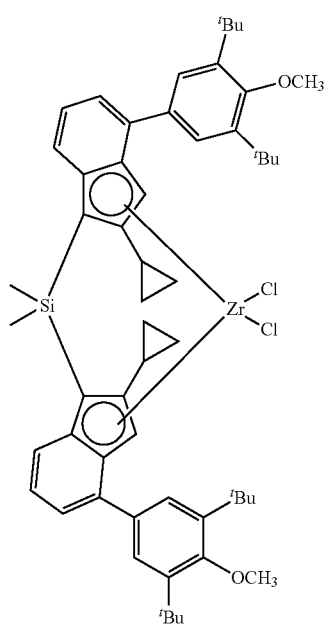
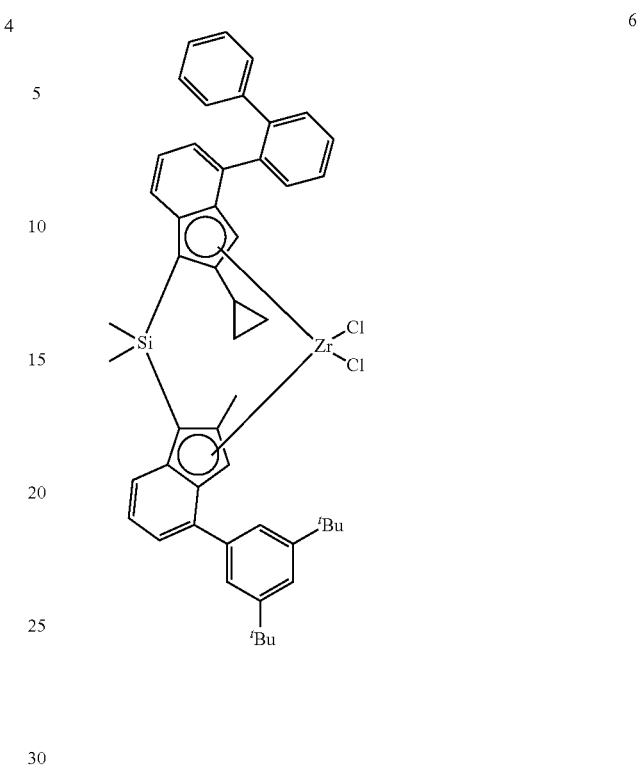
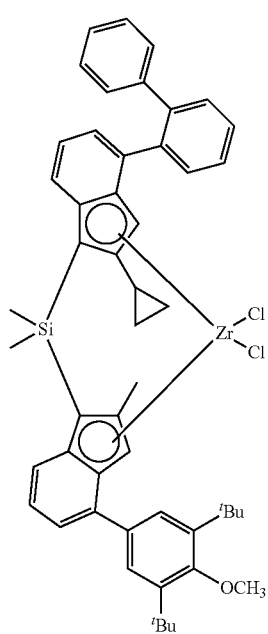
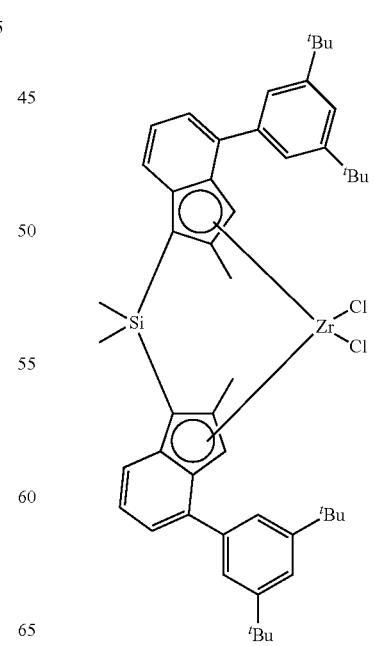

EXAMPLES

Synthesis of rac-dimethylsilyl bis(2-methyl-4-(3',5'-di-tert-butyl-4'-methoxy-phenyl)indenyl zirconium dichloride (Catalyst 1)

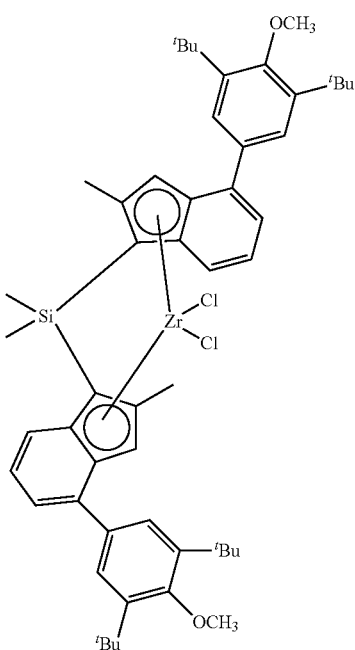

Lithium {1-[2-methyl-4-(3',5'-di-tert-butyl-4'-methoxy-phenyl)indenide]}

A solution of 2-methyl-7-(3',5'-di-tert-butyl-4'-methoxy-phenyl)-indene (7.15 g, 20.515 mmol) in diethyl ether (50 mL) was precooled at −35° C. for 20 min. n-BuLi (2.5 M, 8.5 mL, 21.25 mmol) was added. The solution was stirred at room temperature for 4 hours. All volatiles were evaporated. The residue was washed with pentane (20 mL×3) and dried under vacuum to give a crude product containing 0.06 equiv. of $Et_2O$ (8.05 g).

Chloro(2-methyl-4-(3',5'-di-tert-butyl-4'-methoxy-phenyl)-indenyl)dimethylsilane $Me_2SiCl_2$ (23 g) was added to a precooled solution of lithium {1-[2-methyl-4-(3',5'-di-tert-butyl-4'-methoxy-phenyl)indenide]}$(Et_2O)_{0.06}$ (4.1 g) in diethyl ether (50 mL). The slurry was stirred at room temperature for 17 hours. All volatiles were removed in vacuo. The residue was extracted with pentane (40 mL×2). The pentane filtrate was evaporated to dryness under vacuum to give chloro(2-methyl-4-(3',5'-di-tert-butyl-4'-methoxy-phenyl)-indenyl)dimethylsilane as an off-white sticky solid (3.765 g).

(2-methyl-4-(3',5'-di-tert-butyl-4'-methoxy-phenyl)-indenyl)dimethylsilyl trifluoromethanesulfonate Toluene (25 mL) was added to a solid mixture of silver trifluoromethanesulfonate (1.21 g) and chloro(2-methyl-4-(3',5'-di-tert-butyl-4'-methoxy-phenyl)-indenyl)dimethylsilane (2 g). The slurry was stirred at room temperature for 4 hours. Toluene was removed under vacuum. The residue was extracted with pentane (40 mL). The pentane filtrate was concentrated under vacuum to give the crude product (containing about 0.26 equivalents of toluene and about 10% unknown compounds) (2.56 g). This crude product was used without further purification.

Bis(2-methyl-4-(3',5'-di-tert-butyl-4'-methoxy-phenyl)-indenyl)dimethylsilane

A precooled solution of above lithium {1-[2-methyl-4-(3',5'-di-tert-butyl-4'-methoxy-phenyl)indenide]}$(Et_2O)_{0.06}$ (1.575 g) in diethyl ether (20 mL) was added to a precooled solution (−35° C. for 15 min) of above (2-methyl-4-(3,5-di-tert-butyl-4-methoxy-phenyl)-indenyl)dimethylsilyl trifluoromethanesulfonate (2.54 g) in diethyl ether (15 mL). The reaction was stirred at room temperature for 2 days. All volatiles were removed under vacuum. The residue was extracted with hexane (20 mL×2). The hexane filtrate was concentrated to dryness to give off-white solid. The solids were dissolved in hexane (10 mL). The solution was concentrated to about 5 mL and put into −35° C. freezer. The precipitates were separated, washed with cold hexane, and dried under vacuum (3.2 g). This crude product was used without further purification.

Dilithium dimethylsilyl bis{1-[2-methyl-4-(3',5'-di-tert-butyl-4'-methoxy-phenyl)indenide]} n-BuLi (2.5 M, 3.5 mL, 8.75 mmol) was added to a precooled slurry of the above crude product (3.12 g) in diethyl ether (30 mL). The solution was stirred at room temperature for 22 hours. The slurry was then cooled to −35° C. for 0.5 hours. The slurry was filtered. The solids were collected, washed with cold diethyl ether (10 mL×2), and dried under vacuum to give the dilithium compound as an $Et_2O$ (0.9 equiv.) adduct (2.15 g).

Rac-dimethylsilyl bis(2-methyl-4-(3',5'-di-tert-butyl-4'-methoxy-phenyl)-indenyl)zirconium dichloride $ZrCl_4$ (0.6 g, 2.575 mmol) was added to a precooled slurry (−35° C. for 15 min) of above dilithium dimethylsilyl bis{1-[2-methyl-4-(3',5'-di-tert-butyl-4'-methoxy-phenyl)indenide]}$[Et_2O]_{0.9}$ (2.14 g, 2.573 mmol) in toluene (30 mL). Additional toluene (10 mL) (precooled at −35° C. for 15 min) was also added. The orange slurry was stirred at room temperature for 16 hours. The reaction mixture was then filtered and the insoluble solid was further washed with toluene (10 mL×2). The filtrates and washings were combined and evaporated to dryness under vacuum. Hexane (45 mL) and toluene (6 mL) were added. The slurry was mixed well and allowed to stay at room temperature overnight. The precipitates were separated and washed with hexane (6 mL×4) and dried under vacuum to give 1.85 g of metallocenes with a rac/meso ratio of about 1.08:1. Further fractional crystallization afforded 0.31 g (12%) of rac metallocene (rac/meso>50/1, containing about 1.2 equivalents of toluene) (this fraction was used for synthesis of supported catalyst below). Additional fractions of rac metallocene (rac/meso>25/1) were also obtained (0.438 g, containing 1.2-1.3 equivalents of toluene).

$^1$H NMR (400 MHz, $C_6D_6$, 23° C.): rac: δ 7.93 (s, 4H), 7.47 (d, 2H), 7.43 (d, 2H), 7.13 (s, 2H), 6.91 (m, 2H), 3.44 (s, 6H, —$OCH_3$), 2.01 (s, 6H, ind-$CH_3$), 1.60 (s, 36H, 4×$^tBu$), 0.79 (s, 6H, $SiMe_2$).

Synthesis of rac-dimethylsilyl bis(2-cyclopropyl-4-(3',5'-di-tert-butylphenyl)-indenyl)zirconium dichloride (Catalyst 3, Comparative)

Indene Synthesis

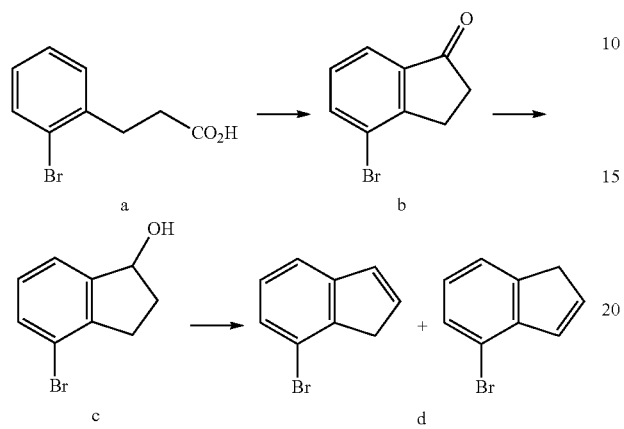

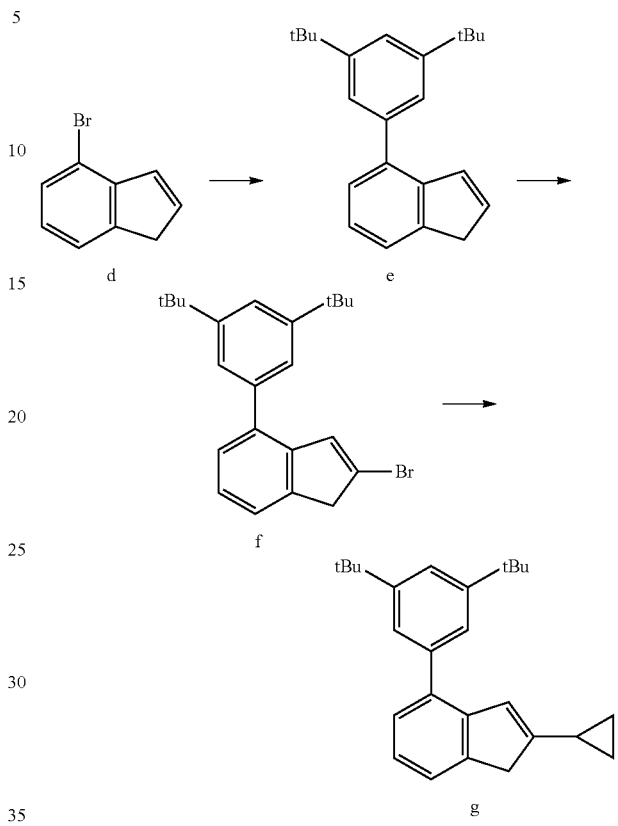

4-Bromo-2,3-dihydro-1H-inden-1-one (b): 3-(2-Bromophenyl)propanoic acid (a) (550 g, 2.4 mol, 1 equiv) was dissolved in 1,2-dichloroethane (5.5 L). Thionyl chloride (437.8 mL, 6 mol, 2.5 equiv) was added to the solution and the mixture was refluxed for 24 hours. The reaction was cooled to room temperature and concentrated under reduced pressure. The residue was dissolved in methylene chloride (1 L) and added dropwise to a mechanically stirred suspension of anhydrous aluminum chloride (526.9 g, 3.96 mol, 1.65 equiv) in dichloromethane (1 L) while keeping the reaction temperature below 27° C. The reaction was stirred at room temperature for three hours before being quenched into a five gallon bucket which was half-full of ice. The resulting mixture was extracted with dichloromethane (3×3 L). The combined organic layers were washed sequentially with saturated brine (2 L) and saturated sodium bicarbonate (2 L). The organic layer was dried over sodium sulfate, and concentrated under reduced pressure. The resulting solid was dried overnight in a vacuum oven at 30° C. to give compound b (435 g, 86% yield) as an off-white solid.

4-Bromo-2,3-dihydro-1H-inden-1-ol (c): A solution of compound b (435 g, 2.06 mol, 1 equiv) in ethanol (5 L) was treated with sodium borohydride (101.6 g, 2.68 mol, 1.3 equiv) and stirred overnight at room temperature. The reaction was concentrated under reduced pressure and the residue partitioned between 4 L of dichloromethane and 4 L of 10% aqueous hydrochloric acid. The layers were separated and the aqueous layer was extracted with dichloromethane (3×1 L). The combined organic layers were washed with saturated brine (2 L), dried over sodium sulfate and concentrated under reduced pressure. The resulting solid was dried overnight in a vacuum oven at 30° C. to give compound c (422 g, 96% yield) as an off-white solid.

4-Bromo-1H-indene (d): Compound c (150 g, 704 mmol, 1 equiv) was suspended in a mixture of concentrated sulfuric acid (250 mL) and water (1.25 L). The mixture was refluxed overnight. The reaction was cooled and extracted with 1.5 L of dichloromethane. The organic layer was washed with saturated sodium bicarbonate (1.5 L), dried over sodium sulfate, and concentrated under reduced pressure. The residue was purified over silica gel (800 g), eluting with heptanes to give compound d (95 g, 69% yield) as a light yellow oil.

4-(3',5'-Di-tert-butylphenyl)-1H-indene (e): Mixture of compound d (60 g, 308 mmol, 1 equiv), 2-(3,5-di-tert-butylphenyl)-4,4,5,5-tetramethyl-1,3,2-dioxaborolane (126 g, 400 mmol, 1.3 equiv), powdered potassium carbonate (128 g, 924 mmol, 3 equiv) and bis(triphenylphosphine)palladium(II)dichloride (25.3 g, 31 mmol, 0.1 equiv), 1,4-dioxane (300 mL) and water (150 mL) was heated overnight at 80° C. The reaction was poured into 700 mL of water and extracted with ethyl acetate (3×500 mL). The combined organic layers were washed with saturated brine (1 L), dried over sodium sulfate, and concentrated under reduced pressure. The resulting residue was purified over silica gel (1 Kg) eluting with heptanes to give compound e (59 g, 63% yield) as a light yellow oil.

2-Bromo-4-(3',5'-di-tert-butylphenyl)-1H-indene (f): A cold solution (5° C.) of compound e (49 g, 161 mmol, 1 equiv), dimethyl sulfoxide (500 mL) and water (5 mL) was treated in one portion with N-bromosuccinimide (43 g, 241 mmol, 1.5 equiv). The bath was removed and the reaction allowed to stir at room temperature overnight. The reaction was poured into water (1 L) and the mixture extracted with ethyl acetate (2×500 mL). The combined organic layers were washed with saturated brine (1 L), dried over sodium sulfate and concentrated under reduced pressure. The resulting residue was dissolved in toluene (500 mL) and p-toluenesulfonic acid (6.2 g, 32.6 mmol, 0.2 equiv) was added. The mixture was refluxed for 20 hours while removing water with a Dean-Stark trap. The reaction was cooled to room temperature and concentrated under reduced pressure. The resulting residue was purified over silica gel (1 Kg) eluting with heptanes to give compound f (41 g, 66% yield) as a white solid.

2-Cyclopropyl-4-(3',5'-di-tert-butylphenyl)-1H-indene (g): A solution of compound f (16.1 g, 42.0 mmol, 1 equiv) and anhydrous toluene (200 mL) was treated with [1,1'-bis(diphenylphosphino)ferrocene]dichlopalladium(II) DCM adduct (3.43 g, 4.2 mmol, 0.1 equiv). After stirring for 10 minutes, 0.5 M cyclopropylmagnesium bromide in tetrahydrofuran (420 mL, 210 mmol, 5 equiv) was added dropwise. The reaction was heated at 60° C. overnight. The reaction was cooled with an ice bath, acidified with 1N HCl to pH 3 and extracted with ethyl acetate (3×500 mL). The combined organic layers were washed with saturated brine (800 mL), dried over sodium sulfate, and concentrated under reduced pressure. The residue was purified on an AnaLogix (65-200 g) column with dry-loading, eluting with heptanes to give compound g (7.0 g, 48% yield) as a white solid.

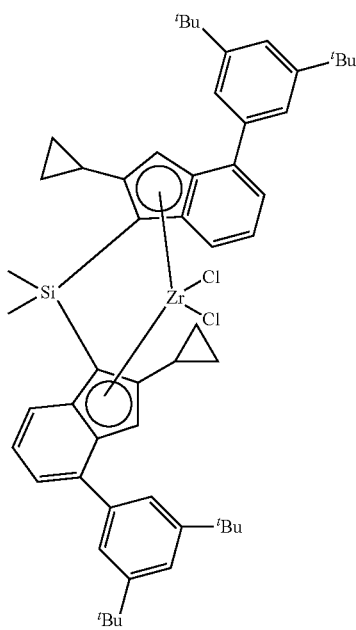

Lithium {1-[2-cyclopropyl-4-(3',5'-di-tert-butylphenyl)indenide]}: A solution of 2-cyclopropyl-7-(3',5'-di-tert-butylphenyl)-indene (g) (5.93 g, 17.21 mmol) in diethyl ether (40 mL) was precooled at −35° C. for 30 min. n-BuLi (2.5 M, 7 mL, 17.5 mmol) was added. The solution was stirred at room temperature for 16 h. All volatiles were evaporated. The residue was washed with pentane (10 mL×4, 40 mL×1) and dried under vacuum to give the crude product (4.68 g).

Chloro(2-cyclopropyl-4-(3',5'-di-tert-butylphenyl)-indenyl)dimethylsilane: A solution of lithium {1-[2-cyclopropyl-4-(3,5-di-tert-butylphenyl)indenide]} (2.38 g, 6.791 mmol) in diethyl ether (30 mL) was precooled at −35° C. for 10 min. Me$_2$SiCl$_2$ (12.9 g, 99.95 mmol) was added and the white slurry was stirred at room temperature for 28 h. All volatiles were evaporated. The residue was extracted with pentane (40 mL). The pentane filtrate was evaporated to dryness under vacuum to give chloro(2-cyclopropyl-4-(3',5'-di-tert-butylphenyl)-indenyl)dimethylsilane as a white sticky solid (1.68 g).

(2-Cyclopropyl-4-(3',5'-di-tert-butylphenyl)-indenyl)dimethylsilyl trifluoromethanesulfonate: A solution of chloro(2-cyclopropyl-4-(3,5-di-tert-butylphenyl)-indenyl)dimethylsilane (1.64 g, 3.752 mmol) in toluene (10 mL) was added to stirring mixture of silver trifluoromethanesulfonate (1 g, 3.892 mmol) in toluene (10 mL). The slurry was stirred at room temperature for 3 h. Toluene was removed under vacuum and the residue was extracted with pentane (40 mL). The pentane filtrate was concentrated under vacuum to give crude (2-cyclopropyl-4-(3,5-di-tert-butylphenyl)-indenyl)dimethylsilyl trifluoromethanesulfonate (1.93 g).

Bis(2-cyclopropyl-4-(3',5'-di-tert-butylphenyl)-indenyl)dimethylsilane:

A precooled solution of lithium {1-[2-cyclopropyl-4-(3,5-di-tert-butylphenyl)indenide]} (1.26 g, 3.595 mmol) in diethyl ether (20 mL) was added to a precooled solution (−35° C. for 30 min) of (2-cyclopropyl-4-(3,5-di-tert-butylphenyl)-indenyl)dimethylsilyl trifluoromethanesulfonate (1.93 g, 3.504 mmol) in diethyl ether (10 mL). The mixture was stirred at room temperature for 23 hr. All volatiles were removed under vacuum. The residue was extracted with pentane (40 mL). The pentane filtrate was evaporated to dryness to give the crude product (2.6 g).

Dilithium dimethylsilyl bis{1-[2-cyclopropyl-4-(3',5'-di-tert-butylphenyl)indenide]}: Then the above crude product (2.54 g, 3.408 mmol) was dissolved in diethyl ether (25 mL) and precooled at −20° C. for 1 h. n-BuLi (2.5 M, 2.8 mL, 7 mmol) was added. The solution was stirred at room temperature for 22 h. All volatiles were removed under vacuum. The residue was washed with pentane (5 mL×3) and dried under vacuum to give the dilithium compound as an Et$_2$O (0.88 eq) adduct (2.66 g).

Dimethylsilyl bis(2-cyclopropyl-4-(3',5'-di-tert-butylphenyl)-indenyl)zirconium dichloride: A precooled solution of {dilithium dimethylsilyl bis{1-[2-cyclopropyl-4-(3,5-di-tert-butylphenyl)indenide]}}[Et$_2$O]$_{0.88}$ (2.64 g, 3.211 mmol) in Et$_2$O (15 mL) was added to precooled ZrCl$_4$ (0.75 g, 3.218 mmol) in Et$_2$O (20 mL). The slurry was stirred at room temperature for 20 h. The mixture was evaporated to dryness. The residue was extracted with pentane (15 mL once, 5 mL once) (Fraction 1). The residue was then extracted with toluene (15 mL) (Fraction 2).

Fraction 1: The pentane filtrate was concentrated to dryness under vacuum to give the crude metallocene. Crystallization of the crude product in pentane (20 mL) at −15° C. affords the metallocene with a rac/meso-ratio of 7:1 (0.79 g, 27%). Further fractional crystallization separation yields rac-dimethylsilyl bis(2-cyclopropyl-4-(3,5-di-tert-butylphenyl)-indenyl) zirconium dichloride as a yellow solid (0.15 g, 5.2%) having a rac/meso ratio of greater than 20:1.

Fraction 2: Toluene filtrate was concentrated to dryness to give 0.74 g (25%) of metallocenes with a rac/meso ratio of 1:28. Further washing 0.5 g of this material with pentane affords 0.4 g of metallocene with a rac/meso ratio of 1:56.

$^1$H NMR (400 MHz, C$_6$D$_6$, 23° C.): rac: δ 7.95 (m, 4H), 7.62 (m, 2H), 7.49 (m, 4H), 6.98 (s, 2H), 6.90 (m, 2H), 1.84 (m, 2H), 1.42 (s, 36H), 0.99 (s, 6H, SiMe$_2$), 0.86 (m, 2H), 0.66 (m, 2H), 0.50 (m, 2H), 0.13 (m, 2H). meso: 7.92 (m, 4H), 7.61 (m, 2H), 7.59-7.27 (m, 4H), 6.86-6.82 (m, 4H), 1.91 (m, 2H), 1.44 (s, 36H), 1.27 (m, 2H), 1.09 (s, 3H, SiMe), 0.91 (s, 3H, SiMe), 0.68 (m, 2H), 0.61 (m, 2H), 0.13 (m, 2H).

Synthesis of rac-dimethylsilyl bis(4-(3',5'-di-tert-butyl-4'-methoxyphenyl)-2-cyclopropyl-indenyl) zirconium dichloride (Catalyst 4)

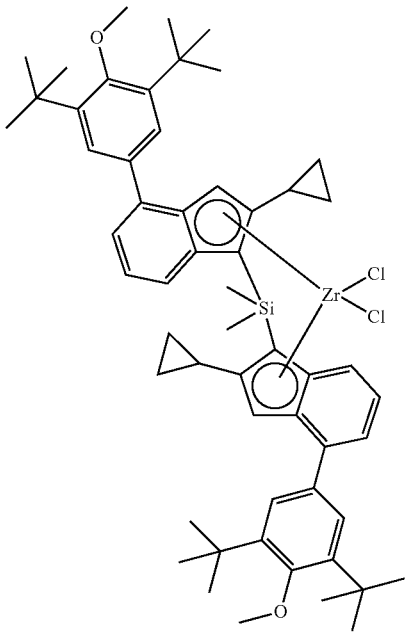

2-(1H-inden-4-yl)-4,4,5,5-tetramethyl-1,3,2-dioxaborolane: A mixture of 4-bromo-1H-indene (21.0 g, 107.7 mmol), bis(pinacolato)diboron (30.0 g, 118.1 mmol), powdered anhydrous potassium acetate (21.0 g, 214.3 mmol), bis(triphenylphosphine) palladium(II) dichloride (2.4 g, 3.4 mmol), and DMF (100 mL) was heated under $N_2$ for 5 hours at 110° C. The mixture was poured into 500 mL of water and extracted with hexane (2×100 mL). The combined organic phases were washed with water (50 mL) and concentrated under reduced pressure. The resulting residue was purified over silica gel (eluent: hexane) to yield 2-(1H-inden-4-yl)-4,4,5,5-tetramethyl-1,3,2-dioxaborolane (21.63 g, 83%) as colorless oil.

4-(3,5-Di-tert-butyl-4-methoxyphenyl)-1H-indene: A mixture of 5-bromo-1,3-di-tert-butyl-2-methoxybenzene (11.0 g, 36.9 mmol), 2-(1H-inden-4-yl)-4,4,5,5-tetramethyl-1,3,2-dioxaborolane (8.9 g, 36.9 mmol), potassium carbonate (10.2 g, 73.8 mmol), tetrabutylammonium bromide (2.37 g, 7.38 mmol), bis(triphenylphosphine)palladium(II) dichloride (0.52 g, 0.74 mmol), water (100 mL) and ethanol (10 mL) was refluxed for 3 hours. The reaction was cooled down and extracted with hexane (2×100 mL). The combined organic layers were concentrated under reduced pressure, then the resulting residue was purified over silica gel (eluent: hexane) to get 4-(3,5-di-tert-butyl-4-methoxyphenyl)-1H-indene (10.8 g, 88%) as colorless oil.

2-Bromo-4-(3,5-di-tert-butyl-4-methoxyphenyl)-1H-indene: A pre-cooled (5° C.) solution of 4-(3,5-di-tert-butyl-4-methoxyphenyl)-1H-indene (10.5 g, 31.4 mmol) in dimethyl sulfoxide (100 mL) and water (1 mL) was treated in one portion with N-bromosuccinimide (8.3 g, 47.2 mmol), and the reaction was stirred at room temperature overnight. The mixture was poured into water (500 mL) and extracted with toluene (2×200 mL). The combined organic phases were washed with water (100 mL). Then to the solution, p-toluenesulfonoc acid monohydrate (1.2 g, 6.3 mmol) was added and the mixture was refluxed for 6 hours while removing water with a Dean-Stark trap. The mixture was cooled down and concentrated under reduced pressure. The residue was purified over silica gel (eluent: hexane) to get 2-bromo-4-(3,5-di-tert-butyl-4-methoxyphenyl)-1H-indene (7.21 g, 56%) as light yellow solid.

4-(3,5-di-tert-butyl-4-methoxyphenyl)-2-cyclopropyl indene: A solution of 2-bromo-4-(3,5-di-tert-butyl-4-methoxyphenyl)-1H-indene (2.80 g, 6.8 mmol) and [1,3-bis(2,6-diisopropylphenyl)imidazol-2-ylidene]triphenylphosphine Nickel(II) dichloride (95 mg, 0.14 mmol) was treated with cyclopropylmagnesium bromide solution (0.5 M in THF, 16.0 mL, 8.2 mmol), and the resulting mixture was refluxed for 5 hours. Then the reaction was poured into 50 mL of aqueous 0.5 N HCl and extracted with toluene (50 mL×2), the combined organic phases were washed with water (50 mL), dried over $MgSO_4$, and concentrated under reduced pressure. The resulting residue was purified over silica gel (eluent: hexane) to yield an off-white solid as product (1.40 g, 55%).

Lithium {1-[4-(3,5-di-tert-butyl-4-methoxyphenyl)-2-cyclopropyl indenide]}: A solution of 7-(3,5-di-tert-butyl-4-methoxyphenyl)-2-cyclopropyl-indene (1.35 g, 3.61 mmol) in diethyl ether (20 mL) was treated with n-BuLi (2.5 M, 1.5 mL, 3.79 mmol), and the reaction was stirred at room temperature for 3 h. Then all volatiles were evaporated. The residue was washed with hexane (5 mL×2) and dried under vacuum to the product as white solid (1.28 g, 93%).

Chlorodimethyl[4-(3,5-di-tert-butyl-4-methoxyphenyl)-2-cyclopropyl-indenyl]silane: A solution of Lithium 1-[4-(3,5-di-tert-butyl-4-methoxyphenyl)-2-cyclopropyl indenide] (0.65 g, 1.71 mmol) in diethyl ether (30 mL) was treated with $Me_2SiCl_2$ (1.30 g, 10.3 mmol), and the resulting slurry was stirred at room temperature for 5 h. All volatiles were evaporated and the residue was extracted with hexane (30 mL×3). The combined solution was concentrated to dryness and dried over under vacuum to give white color foam as the product (0.77 g, 96%).

Dimethylsilyl[4-(3,5-di-tert-butyl-4-methoxyphenyl)-2-cyclopropyl-indenyl]trifluoromethanesulfonate: A solution of chlorodimethyl[4-(3,5-di-tert-butyl-4-methoxyphenyl)-2-cyclopropyl-indenyl]silane (0.76 g, 1.64 mmol) in toluene (30 mL) was treated with silver trifluoromethanesulfonate (0.48 g, 1.80 mmol) while stirring, and the resulting white slurry was stirred at room temperature for 5 h. Toluene was removed under vacuum and the residue was extracted with hexane (30 mL×3). The combined solution was concentrated to dryness and dried over under vacuum to give white color foam as the product (0.93 g, 98%).

Bis(4-(3,5-di-tert-butyl-4-methoxyphenyl)-2-cyclopropyl-indenyl)dimethylsilane: A solution of dimethylsilyl[4-(3,5-di-tert-butyl-4-methoxyphenyl)-2-cyclopropyl-indenyl]trifluoromethanesulfonate (0.90 g, 1.55 mmol) in diethyl ether (30 mL) was treated with lithium 1-[4-(3,5-di-tert-butyl-4-methoxyphenyl)-2-cyclopropyl indenide] (0.59 g, 1.55 mmol, and the reaction was stirred at room temperature for 6 hours. The solvent was evaporated and the resulting residue was subjected to flash chromatography (silica gel, eluent:hexane) to give the product as a white color solid (0.96 g, 77%).

Dilithium dimethylsilyl bis(4-(3,5-di-tert-butyl-4-methoxyphenyl)-2-cyclopropyl indenide): A solution of bis (4-(3,5-di-tert-butyl-4-methoxyphenyl)-2-cyclopropyl-indenyl)-dimethylsilane (0.95 g, 1.18 mmol) in diethyl ether (20 mL) was treated with n-BuLi (2.5 M, 0.97 mL, 2.42 mmol), and the reaction was stirred at room temperature for 3 h. All volatiles were evaporated. The residue was washed with cool hexane (10 mL×2) and dried under vacuum to the product as white solid (0.89 g, 92%).

Dimethylsilyl bis(4-(3',5'-di-tert-butyl-4'-methoxyphenyl)-2-cyclopropyl-indenyl)zirconium dichloride: A solution of the dilithium dimethylsilyl bis(4-(3,5-di-tert-butyl-4-methoxyphenyl)-2-cyclopropyl indenide) (0.86 g, 1.05 mmol) in diethyl ether (30 mL) was treated with $ZrCl_4$ (0.24 g, 1.05 mmol). The mixture was stirred at room temperature overnight. All the volatiles were evaporated to dryness. The residue was extracted with toluene (40 mL). The extract solution was concentrated and the residue was washed with 10 mL of hexane to get a crude product (0.72 g) as rac/meso ratio of 2.0:1. The crude product was recrystallized from 20 mL of hexane and 1.5 mL of toluene to give 433 mg of metallocene as rac/meso ratio of 4.8:1. Then the product was recrystallized from 20 mL of hexane and 1.0 mL of toluene to afford 261 mg of metallocene with rac/meso ratio of 8.5:1. The product was further recrystallized from 15 mL of hexane and 0.5 mL of toluene to afford dimethylsilyl bis(4-(3,5-di-tert-butyl-4-methoxyphenyl)-2-cyclopropyl-indenyl)zirconium dichloride (containing ca. 0.44 equiv. of hexane and ca. 0.07 equiv. of toluene residue) with rac/meso ratio of 15:1 (0.121 g, 11.4%). $^1$H NMR (400 MHz, $C_6D_6$, 23° C.), rac: δ 7.96 (m, 4H), 7.48 (m, 4H), 6.97 (s, 2H), 6.89 (m, 2H), 3.37 (s, 6H), 1.83 (m, 2H), 1.59 (s, $^tBu×4$, 36H), 0.96 (s, $SiMe_2$, 6H), 0.90-0.81 (m, 2H), 0.65 (m, 2H), 0.50 (m, 2H), 0.10 (m, 2H).

Synthesis of rac-dimethylsilyl (4-o-biphenyl-2-cyclopropyl-indenyl)(2-m ethyl-4-(3',5'-di-tert-butyl-4'-methoxy-phenyl)-indenyl)zirconium dichloride (Catalyst 5)

Indene Synthesis:

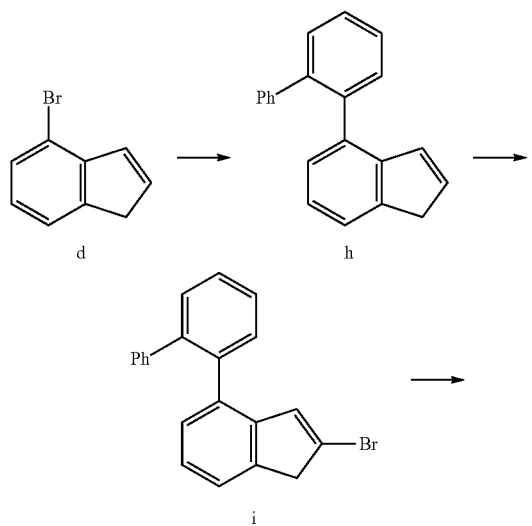

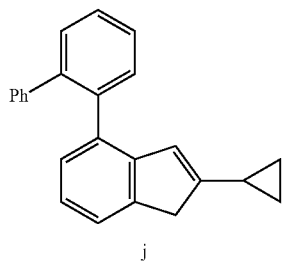

4-([1,1'-Biphenyl]-2 yl)-1H-indene (h): A mixture of compound d (40 g, 205 mmol, 1 equiv), (biphenyl-2-yl) boronic acid (81.2 g, 410 mmol, 2 equiv), powdered potassium carbonate (85 g, 615 mmol, 3 equiv), and bis(triphenylphosphine)palladium(II)dichloride (7.2 g, 10.3 mmol, 0.05 equiv), 1,4-dioxane (300 mL) and water (150 mL) was heated overnight at 80° C. The reaction was poured into 500 mL of water and extracted with ethyl acetate (3×400 mL). The combined organic layers were washed with saturated brine (300 mL), dried over sodium sulfate, and concentrated under reduced pressure. The resulting residue was purified over silica gel (400 g) eluting with heptanes to give compound (h) (50 g, 91% yield) as a light-yellow oil that slowly turned to an off-white solid on standing.

4-([1,1'-Biphenyl]-2-yl)-2-bromo-1H-indene (i): A cold solution (5° C.) of compound h (40 g, 149 mmol, 1 equiv), dimethyl sulfoxide (400 mL) and water (5 mL) was treated in one portion with N-bromosuccinimide (39.8 g, 224 mmol, 1.5 equiv). The bath was removed and the reaction allowed to stir at room temperature overnight. The reaction was poured into water (1 L) and extracted with ethyl acetate (2×500 mL). The combined organic layers were washed with saturated brine (1 L), dried over sodium sulfate, and concentrated under reduced pressure. The resulting residue was dissolved in 500 mL of toluene and p-toluenesulfonic acid (5.6 g, 29.4 mmol, 0.2 equiv) was added. This mixture was refluxed for 20 hours while removing water with a Dean-Stark trap. The reaction was cooled to room temperature and concentrated under reduced pressure. The resulting residue was purified over silica gel (1 Kg), eluting with heptanes to give compound i (39 g, 75% yield) as a light yellow solid.

4-([1,1'-Biphenyl]-2-yl)-2-cyclopropyl-1H-indene (j): A solution of compound i (10 g, 28.8 mmol, 1 equiv) and anhydrous toluene (100 mL) was treated with bis(triphenylphosphine)-palladium(II)dichloride (2.35 g, 2.9 mmol, 0.1 equiv). After stirring for 10 minutes, 0.5 M cyclopropylmagnesium bromide in tetrahydrofuran (300 mL, 149.7 mmol, 5.2 equiv) was added dropwise. The reaction was heated at 60° C. overnight. Additional bis(triphenylphosphine)-palladium(II)dichloride (2.35 g, 2.9 mmol, 0.1 equiv) was added and the reaction heated at 60° C. for an additional 24 hours. The reaction was concentrated under reduced pressure and the residue partitioned between water (1 L) and ethyl acetate (1 L). The layers were separated and the aqueous layer washed with ethyl acetate (1 L). The combined organic layers were washed with saturated brine (1 L), dried over sodium sulfate, and concentrated under reduced pressure. The resulting residue was purified over silica gel (200 g) eluting with heptanes to give compound j (3.3 g, 37% yield) as a light yellow oil.

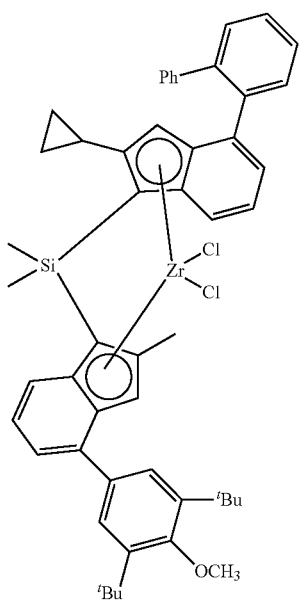

Lithium[1-(4-o-biphenyl-2-cyclopropyl indenide)]: A solution of 7-o-biphenyl-2-cyclopropyl-indene (j) (2.538 g, 8.229 mmol) in diethyl ether (40 mL) was precooled at −35° C. for 0.5 h. n-BuLi (2.5 M, 3.3 mL, 8.25 mmol) was added. The solution was stirred at room temperature for 18 h. All volatiles were evaporated. The yellow solid was washed with pentane (5 mL twice, 10 mL once) and dried under vacuum to give the lithium compound (2.11 g).

Lithium {1-[2-methyl-4-(3',5'-di-tert-butyl-4'-methoxy-phenyl)indenide)]}: A solution of 2-methyl-7-(3',5'-di-tert-butyl-4'-methoxy-phenyl)-indene (7.15 g, 20.515 mmol) in diethyl ether (50 mL) was precooled at −35° C. for 20 min. n-BuLi (2.5 M, 8.5 mL, 21.25 mmol) was added. The solution was stirred at room temperature for 4 hours. All volatiles were evaporated. The residue was washed with pentane (20 mL×3) and dried under vacuum to give a crude product containing 0.06 equiv. of $Et_2O$ (8.05 g).

Chlorodimethyl[4-o-biphenyl-2-cyclopropyl-indenyl]silane: A solution of lithium [1-(4-o-biphenyl-2-cyclopropyl indenide)] (0.87 g, 2.768 mmol) in diethyl ether (30 mL) and THF (10 mL) was precooled at −35° C. for 30 min. $Me_2SiCl_2$ (5.8 g, 44.94 mmol) was added and the slurry was stirred at room temperature for 21 h. All volatiles were evaporated. The residue was extracted with pentane (50 mL) and the filtrate was concentrated to dryness under vacuum to give the product (1.037 g).

Dimethylsilyl[4-o-biphenyl-2-cyclopropyl-indenyl]trifluoromethanesulfonate: A solution of silver trifluoromethanesulfonate (0.67 g, 2.618 mmol) in toluene (15 mL) was added to a stirring solution of above product (1.02 g, 2.544 mmol) in toluene (10 mL). The slurry was stirred at room temperature for 3 h. Toluene was removed under vacuum and the residue was extracted with hexane (50 mL). The pentane filtrate was concentrated under vacuum to give the product (1.13 g).

(4-o-Biphenyl-2-cyclopropyl-indenyl)(2-methyl-4-(3',5'-di-tert-butyl-4'-methoxy-phenyl)-indenyl)dimethylsilane: A precooled solution of lithium {1-[2-methyl-4-(3',5'-di-tert-butyl-4'-methoxy-phenyl)indenide]}$(Et_2O)_{0.06}$ (0.71 g, 1.978 mmol) in diethyl ether (20 mL) was added to a precooled solution of dimethylsilyl[4-o-biphenyl-2-cyclopropyl-indenyl]trifluoromethanesulfonate (1.01 g, 1.963 mmol) in diethyl ether (15 mL). The reaction was stirred at room temperature for 21 h. Diethyl ether was evaporated. To the residue was added hexane (40 mL). The hexane slurry was filtered through Celite™ on a frit. The frit was washed with additional hexane (20 mL once, 10 mL once). All filtrates were combined and were concentrated under vacuum to give the crude product (1.515 g).

Dilithium dimethylsilyl (4-o-biphenyl-2-cyclopropyl indenide)(2-methyl-4-(3',5'-di-tert-butyl-4'-methoxy phenyl)indenide): n-BuLi (2.5 M, 1.8 mL, 4.5 mmol) was added to a precooled solution of the above crude product (1.5 g) in diethyl ether (30 mL). The solution was stirred at room temperature for 23 h. All volatiles were removed under vacuum. The residue was washed with hexane (30 mL once, 20 mL twice) and dried under vacuum to give the crude product (1.25 g).

Dimethylsilyl (4-o-biphenyl-2-cyclopropyl-indenyl)(2-methyl-4-(3',5'-di-tert-butyl-4'-methoxy-phenyl)-indenyl) zirconium dichloride: A precooled solution of the above crude product (1.2 g) in toluene (30 mL) was added to $ZrCl_4$ (0.386 g, 1.656 mmol). Additional cold toluene (20 mL) was added. The mixture was stirred at room temperature for 16 h. The mixture was concentrated to about 35 mL and was filtered through Celite™ on a frit. The Celite™ was washed with additional toluene (5 mL). All filtrates were combined and were concentrated to dryness. $Et_2O$ (20 mL) was added and the mixture was put into −35° C. freezer. After 2 h the mixture was concentrated to dryness again. The residue was extracted with pentane (20 mL four times). Pentane filtrates were combined and evaporated to dryness. $Et_2O$ (10 mL) was added and the solution was evaporated to dryness again. To the residue was added pentane (20 mL). The slurry was stirred at room temperature for 3 d. The precipitates were separated, washed with pentane (10 mL twice) and dried in vacuo (0.185 g, rac/meso=4/1). Further fractional crystallization from hexane/toluene afforded the product (0.055 g, rac/meso=79/1). $^1$H NMR (400 MHz, $CD_2Cl_2$, 23° C.): rac: δ 7.67 (m, 1H), 7.58 (m, 2H), 7.48 (s, 2H), 7.43 (m, 3H), 7.28 (m, 1H), 7.15 (m, 1H), 7.08 (m, 5H), 7.0 (m, 1H), 6.96 (m, 1H), 6.84 (s, 1H), 5.99 (s, 1H), 3.71 (s, 3H), 2.22 (s, 3H), 1.90 (m, 1H), 1.43 ($^t$Bu×2, 18 H), 1.33 (s, 3H), 1.32 (s, 3H), 0.94 (m, 1H), 0.70-0.60 (m, 2H), 0.15 (m, 1H).

Synthesis of rac-dimethylsilyl (4-o-biphenyl-2-cyclopropyl-indenyl)(4-(3',5'-di-tert-butylphenyl)-2-methyl-indenyl)zirconium dichloride (Catalyst 6, Comparative)

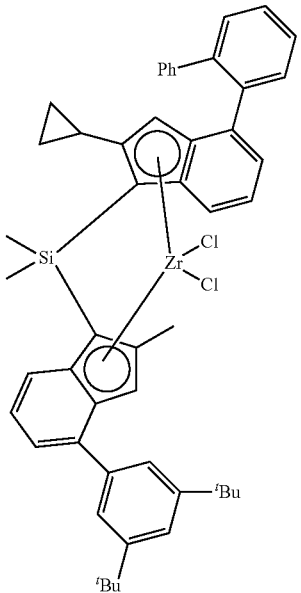

Lithium {1-[4-(3',5'-di-tert-butylphenyl)-2-methyl indenide]}: A solution of 7-(3,5-di-tert-butylphenyl)-2-methyl-indene (5.46 g, 17.14 mmol) in diethyl ether (50 mL) was precooled at −35° C. for 0.5 h. n-BuLi (2.5 M, 7 mL, 17.5 mmol) was added. The solution was stirred at room temperature for 17 h. All volatiles were evaporated. The residue was washed with hexane (10 mL×4) and dried under vacuum to give the crude product (5.7 g).

Chlorodimethyl[4-(3',5'-di-tert-butylphenyl)-2-methyl-indenyl]silane: A solution of the above crude product (1.4 g, 4.315 mmol) in diethyl ether (20 mL) was precooled at −35° C. for 30 min. Me$_2$SiCl$_2$ (8 g, 61.99 mmol) was added and the white slurry was stirred at room temperature for 17 h. All volatiles were evaporated. The residue was extracted with pentane (20 mL) and the filtrate was concentrated to dryness under vacuum to give the product (1.74 g, 98%).

Dimethylsilyl[4-(3',5'-di-tert-butylphenyl)-2-methyl-indenyl]trifluoromethanesulfonate: A solution of chlorodimethyl[4-(3',5'-di-tert-butylphenyl)-2-methyl-indenyl]silane (1.71 g, 4.16 mmol) in toluene (10 mL) was added to a solution of silver trifluoromethanesulfonate (1.1 g, 4.28 mmol) in toluene (5 mL) with stirring. The white slurry was stirred at room temperature for 3 h. Toluene was removed under vacuum and the residue was extracted with pentane (25 mL). The pentane filtrate was concentrated under vacuum to give the product (1.88 g).

(4-o-Biphenyl-2-cyclopropyl-indenyl)(4-(3',5'-di-tert-butylphenyl)-2-methyl-indenyl)dimethylsilane: A precooled solution of dimethylsilyl[4-(3',5'-di-tert-butylphenyl)-2-methyl-1H-inden-1-yl]trifluoromethanesulfonate (0.71 g, 1.353 mmol) in diethyl ether (10 mL) was added to a precooled mixture of lithium[1-(4-o-biphenyl-2-cyclopropyl indenide)] (0.435 g, 1.384 mmol) in diethyl ether (20 mL). The solution was stirred at room temperature for 17 h. Diethyl ether was evaporated. The residue was extracted with pentane (30 mL) and the pentane filtrate was concentrated under vacuum to give the crude product as a white solid (0.9 g).

Dilithium dimethylsilyl (4-o-biphenyl-2-cyclopropyl indenide) (4-(3',5'-di-tert-butylphenyl)-2-methyl indenide): n-BuLi (2.5 M, 1 mL, 2.5 mmol) was added to a precooled solution of the above product (0.86 g, 1.259 mmol) in diethyl ether (25 mL). The solution was stirred at room temperature for 22 h. All volatiles were removed under vacuum. The residue was washed with pentane (10 mL×2) and dried under vacuum to give the dilithium compound as an Et$_2$O adduct (0.915 g).

Dimethylsilyl (4-o-biphenyl-2-cyclopropyl-indenyl)(4-(3',5'-di-tert-butylphenyl)-2-methyl-indenyl)zirconium dichloride: A precooled solution of the above [dilithium dimethylsilyl (4-o-biphenyl-2-cyclopropyl indenide) (4-(3',5'-di-tert-butylphenyl)-2-methyl indenide)][Et$_2$O] (0.9 g, 1.17 mmol) in Et$_2$O (15 mL) was added to a precooled slurry of ZrCl$_4$ (0.275 g, 1.18 mmol) in Et$_2$O (15 mL). The mixture was stirred at room temperature for 20 h. The solution was evaporated to dryness. The residue was washed with pentane (15 mL once and 5 mL once) and then extracted with toluene (20 mL). The toluene filtrates were evaporated to dryness and washed with diethyl ether and then pentane to afford 0.11 g (11%) of the metallocene with a rac/meso-ratio of 5:1. The product was further washed with diethyl ether to give 0.04 g (4.1%) of dimethylsilyl (4-o-biphenyl-2-cyclopropyl-indenyl)(4-(3',5'-di-tert-butylphenyl)-2-methyl-indenyl)zirconium dichloride with a rac/meso ratio of 33:1. $^1$H NMR (400 MHz, CD$_2$Cl$_2$, 23° C.): rac: δ 7.67 (m, 1H), 7.59 (m, 2H), 7.4 (m, 6H), 7.33 (m, 1H), 7.15 (m, 1H), 7.08 (m, 5H), 7.01 (m, 1H), 6.96 (m, 1H), 6.85 (s, 1H), 6.00 (s, 1H), 2.22 (s, 3H), 1.89 (m, 1H), 1.34-1.32 ($^t$Bu×2 overlapped with SiMe$_2$, 24H), 0.94 (m, 1H), 0.73-0.60 (m, 2H), 0.15 (m, 1H). Characteristic $^1$H NMR chemical shifts for meso: δ 5.83 (s, 1H), 2.38 (s, 3H), 1.90 (m, 1H), 1.46 (s, 3H, SiMe), 1.33 (s, 18H, $^t$Bu×2), 1.23 (s, 3H, SiMe).

Supported Catalysts

Supported rac-dimethylsilyl bis(2-methyl-4-(3',5'-di-tert-butyl-4'-methoxy-phenyl)-indenyl)zirconium dichloride (Catalyst A) 43.0 mg, 0.0420 mmol of Catalyst 1 (with 1.2 equivalents of toluene therein) and 0.3854 g of 30 wt % MAO in toluene were stirred together in 2 mL of toluene for 1.5 h. In a small celstir 130° C. calcined silica pretreated with MAO (SMAO) (1.0499 g) was slurried in 20 mL of toluene and chilled. The transition metal catalyst was added to the silica and stirred for 1 hour. The slurry was kept cool by placing in a freezer during the hour. The slurry was then stirred at 40° C. for 1 hour. Thereafter it was filtered, reslurried in 20 mL of toluene at 60° C. for 30 min and filtered again. The slurry was reslurried in 20 mL of toluene at 60° C. for an additional 30 min and filtered two additional times. The solid was washed with 25 mL of toluene and 10 mL of pentane. The solid was dried under vacuum overnight. 0.9177 g of pink solid was recovered.

The SMAO is typically prepared as follows: 130° C. Calcined Davison™ 948 Silica (20.8606 g, calcined at 130° C.) was slurried in 121 mL of toluene and chilled in the freezer (−35° C.). MAO (50.5542 g of a 30% wt solution in toluene) was added slowly in 3 parts with the silica slurry returned to the freezer for a few minutes (approx. 2 min) between additions. The slurry was stirred at room temperature for 2 hours, filtered with a fine glass frit filter, reslurried in 80 mL of toluene for 15 min at room temperature, and then filtered again. The solid was reslurried in 80 mL of toluene at 80° C. for 30 min and then filtered. The solid was reslurried in 80 mL of toluene at 80° C. for 30 min and then filtered a final time. The celstir and solid were washed out with 40 mL of toluene. The solid was then washed with pentane and dried under vacuum for 24 hours. Collected 28.9406 g of a free flowing white powder.

Supported rac-dimethylsilyl bis(2-methyl-4-(3',5'-di-tert-butyl-phenyl)-indenyl)zirconium dichloride (Catalyst B). Rac-dimethylsilyl bis(2-methyl-4-(3',5'-di-tert-butyl-phenyl)-indenyl)zirconium dichloride (Catalyst 7) (36 mg, 0.042 mmol) and MAO (0.3480 g of a 30% by weight solution in toluene) were mixed together with 2 mL of toluene and set to stir for 1 hr 10 min at room temperature. SMAO (1.0598 g) was slurried in 20 mL of toluene and chilled in the freezer (−35° C.). The catalyst solution was added to the slurry and stirred for 1 h. The slurry was occasionally placed in the freezer to maintain it slightly below room temperature. The slurry was stirred for 2 h at 40° C. then filtered, reslurried in 20 mL of toluene at 60° C. for 30 min and filtered again. The slurry was reslurried in 20 mL at 60° C. for another 30 min before filtering again, and then reslurried one final time at 60° C. for 30 min. The slurry was filtered one final time and the celstir washed out with 20 mL of toluene. The solid was washed with pentane and dried to give 0.9494 g of pink solid.

Supported Dimethylsilyl bis(4-(3',5'-di-tert-butyl-4'-methoxyphenyl)-2-cyclopropyl-indenyl)zirconium dichloride (Catalyst C). Dimethylsilyl bis(4-(3',5'-di-tert-butyl-4'-methoxyphenyl)-2-cyclopropyl-indenyl)zirconium dichloride (catalyst 4) (25.5 mg, 0.0252 mmol) and MAO (0.2141 g of a 30% by weight solution in toluene) were mixed together with 2 mL of toluene and set to stir for 1 h at room temperature. SMAO (0.6308 g) was slurried in 20 mL of toluene and chilled in the freezer (−35° C.) for 5 min.

The catalyst solution was added to the slurry and stirred for 1 h. The slurry was placed in the freezer to maintain it slightly below room temperature. The slurry was stirred for 2 h at 40° C. then filtered, reslurried in 20 mL of toluene at 60° C. for 30 min and filtered again. The slurry was reslurried in 20 mL at 60° C. for another 30 min before filtering again, and then reslurried one final time at 60° C. for 30 min. The slurry was filtered one final time and the celstir washed out with 20 mL of toluene. The solid was washed with pentane and dried under vacuum. Collected 0.5682 g of pink solid.

Supported dimethylsilyl bis(4-(3',5'-di-tert-butyl-phenyl)-2-cyclopropyl-indenyl)zirconium dichloride (Catalyst D). Dimethylsilyl bis(4-(3',5'-di-tert-butyl-phenyl)-2-cyclopropyl-indenyl)zirconium dichloride (catalyst 3) (31.0 mg, 0.0342 mmol) and MAO (0.2869 g of a 30% by weight solution in toluene) were mixed together with 2 mL of toluene and set to stir for 1 h at room temperature. SMAO (0.8565 g) was slurried in 20 mL of toluene and chilled in the freezer (−35° C.) for 5 min. The catalyst solution was added to the slurry and stirred for 1 h. The slurry was occasionally placed in the freezer to maintain it slightly below room temperature. The slurry was stirred for 2 h at 40° C. then filtered, reslurried in 20 mL of toluene at 60° C. for 30 min and filtered again. The slurry is reslurried in 20 mL at 60° C. for another 30 min before filtering again, and then reslurried one final time at 60° C. for 30 min. The slurry was filtered one final time and the celstir washed out with 20 mL of toluene. The solid was washed with pentane and dried under vacuum. Collected 0.8066 g of pink solid.

Supported dimethylsilyl (4-o-biphenyl-2-cyclopropyl-indenyl)(2-methyl-4-(3',5'-di-tert-butyl-4'-methoxy-phenyl)-indenyl)zirconium dichloride (Catalyst E). Dimethylsilyl (4-o-biphenyl-2-cyclopropyl-indenyl)(2-methyl-4-(3',5'-di-tert-butyl-4'-methoxy-phenyl)-indenyl) zirconium dichloride (catalyst 5) (22.4 mg, 0.0257 mmol) and MAO (0.22 g of a 30% by weight solution in toluene) were mixed together with 2 mL of toluene and set to stir for 1 h at room temperature. SMAO (0.6439 g) was slurried in 20 mL of toluene and chilled in the freezer (−35° C.) for 5 min. The catalyst solution was added to the slurry and stirred for 1 h. The slurry was placed in the freezer to maintain it slightly below room temperature. The slurry was stirred for 2 h at 40° C. then filtered, reslurried in 20 mL of toluene at 60° C. for 30 min and filtered again. The slurry was reslurried in 20 mL at 60° C. for another 30 min before filtering again, and then reslurried one final time at 60° C. for 30 min. The slurry was filtered one final time and the celstir washed out with 20 mL of toluene. The solid is washed with pentane and dried under vacuum overnight. Collected 0.5910 g of pink solid.

Supported dimethylsilyl (4-o-biphenyl-2-cyclopropyl-indenyl)(2-methyl-4-(3',5'-di-tert-butyl-phenyl)-indenyl)zirconium dichloride (Catalyst F). In a 20 mL vial, the metallocene dimethylsilyl (4-o-biphenyl-2-cyclopropyl-indenyl)(2-methyl-4-(3',5'-di-tert-butyl-phenyl)-indenyl) zirconium dichloride (catalyst 6) (19.4 mg, 0.0230 mmol) was stirred alongside MAO (30% by weight in toluene, 0.2125 g of solution) along with another 2 mL of toluene for 1 h. In a small celstir, SMAO (0.5747 g) was slurried in 20 mL of toluene. The celstir was chilled for 1 min in the freezer before the catalyst solution is added to the slurry. The slurry was stirred for 1 h while spending 1 min of every 10 min in the freezer. The slurry was then heated to 40° C. and stirred for 2 h. The slurry was then filtered, reslurried in 20 mL of toluene and stirred for an additional 30 min at 60° C. The slurry was then filtered, reslurried in 20 mL of toluene and stirred for an additional 30 min at 60° C. The slurry was then filtered, reslurried in 20 mL of toluene and stirred for an additional 30 min at 60° C. and then filtered for the final time. The celstir was washed out with 20 mL of toluene and the solid was dried under vacuum. Collected 0.5044 g of pink solid.

General Procedure for Small Scale Polymerization

Unless stated otherwise propylene homopolymerization and ethylene-propylene copolymerizations are carried out in a parallel pressure reactor, as generally described in U.S. Pat. No. 6,306,658, U.S. Pat. No. 6,455,316, WO00/09255, and Murphy et al., J. Am. Chem. Soc., 2003, 125, pp. 4306-4317, each of which is incorporated by reference herein in its entirety. Although specific quantities, temperatures, solvents, reactants, reactants ratios, pressures, and other variables may need to be adjusted from one reaction to the next, the following describes a typical polymerization performed in a parallel, pressure reactor.

Propylene Polymerization with Metallocene: Examples 1-18. A pre-weighed glass vial insert and disposable stirring paddle are fitted to each reaction vessel of the reactor (which contains 48 individual reaction vessels). The reactor is then closed and propylene is introduced as a gas to each vessel. Thereafter, solvent (e.g., iso hexane) is added to bring the total reaction volume, including subsequent additions, to 5 mL and the reactor vessels are heated to their set temperature (typically about 50° C. to 110° C.).

The contents of the vessel are stirred at 800 rpm. An activator solution of 100-1000 molar equivalents of methyl alumoxane (MAO) in toluene is then injected into the reaction vessel along with 500 micro liters of toluene, followed by a toluene solution of catalyst (typically at a concentration of 0.50 mM in toluene which usually provides about 20 to 40 nmol of catalyst) and another aliquot of toluene (500 microliters). Equivalence is determined based on mol equivalents relative to moles of the transition metal in the transition metal complex. The reaction in then allowed to proceed until a predetermined pressure drop is obtained. Alternatively, the reaction may be allowed to proceed for a pre-determined amount of time. Thereafter, the reaction is quenched by pressurizing the reaction vessel with compressed air. After the polymerization reaction, the glass vial insert containing the polymer product and solvent is removed from the pressure cell and the inert atmosphere glove box, and the volatile components are removed using a Genevac HT-12 centrifuge and Genevac VC300D vacuum evaporator operating at elevated temperature and reduced pressure. The vial is then weighed to determine the yield of polymer product. The resultant polymer is analyzed by Rapid GPC to determine the molecular weight and by DSC to determine the melting point.

Ethylene Propylene Copolymerization with Supported Catalyst. A pre-weighed glass vial insert and disposable stirring paddle were fitted to each reaction vessel of the reactor, which contains 48 individual reaction vessels. The reactor was then closed and propylene gas was introduced to each vessel to purge the nitrogen out of the system. If any modules receive hydrogen, it is added in now during the purge process. The solvent (typically isohexane) is added next according to the set total reaction volume, including the following additions, to 5 mL usually. At this time scavenger and/or co-catalyst and/or a chain transfer agent, such as tri-n-octylaluminum in toluene (100-1000 nmol) was added. The contents of the vessels are now stirred at 800 rpm. The propylene is now added as gas to a set pressure. Now the reactor vessels are heated to their set run temperature (usually between 50° C. and 110° C.). The ethylene is now added as a comonomer and it will be added as a gas to a pre-determined pressure (typically 10-100 psi) above the pressure of the propylene while the reactor vessels were heated to a set run temperature. The slurry catalysts are vortexed to suspend the catalyst particles into a solution. The buffer toluene (typically 100 microliters), the toluene solution of catalyst (typically 3 mg/ml concentration), and another aliquot of toluene (500 microliters) is injected into the reactors now. The reaction was then allowed to proceed until a pre-determined amount of pressure had been taken up by the reaction. Alternatively, the reaction may be allowed to proceed for a set amount of time. At this point, the reaction was quenched by pressurizing the vessel with compressed air. After the polymerization reaction, the glass vial insert containing the polymer product and solvent was removed from the pressure cell and the inert atmosphere glove box, and the volatile components were removed using a Genevac HT-12 centrifuge and Genevac VC3000D vacuum evaporator operating at elevated temperature and reduced pressure. The vial was then weighed to determine the yield of the polymer product. The resultant polymer was analyzed by Rapid GPC (see below) to determine the molecular weight and by DSC (see below) to determine melting point.

To determine various molecular weight related values by GPC, high temperature size exclusion chromatography was performed using an automated "Rapid GPC" system as generally described in U.S. Pat. Nos. 6,491,816; 6,491,823; 6,475,391; 6,461,515; 6,436,292; 6,406,632; 6,175,409; 6,454,947; 6,260,407; and 6,294,388; each of which is fully incorporated herein by reference for US purposes. This apparatus has a series of three 30 cm×7.5 mm linear columns, each containing PLgel 10 um, Mix B. The GPC system was calibrated using polystyrene standards ranging from 580-3,390,000 g/mol. The system was operated at an eluent flow rate of 2.0 mL/minutes and an oven temperature of 165° C. 1,2,4-trichlorobenzene was used as the eluent. The polymer samples were dissolved in 1,2,4-trichlorobenzene at a concentration of 0.1-0.9 mg/mL. 250 uL of a polymer solution was injected into the system. The concentration of the polymer in the eluent was monitored using a Polymer Char IR4 detector. The molecular weights presented are relative to linear polystyrene standards and are uncorrected.

Differential Scanning calorimetry (DSC Procedure-1) measurements were performed on a TA-Q200 instrument to determine the melting point of the polymers. Samples were pre-annealed at 220° C. for 15 minutes and then allowed to cool to room temperature overnight. The samples were then heated to 220° C. at a rate of 100° C./minutes and then cooled at a rate of 50° C./min. Melting points were collected during the heating period.

The amount of ethylene incorporated in the polymers (weight %) was determined by rapid FT-IR spectroscopy on a Bruker Vertex 70 IR in reflection mode. Samples were prepared in a thin film format by evaporative deposition techniques. Weight percent ethylene was obtained from the ratio of peak heights at 729.8 and 1157.9 cm$^{-1}$. This method was calibrated using a set of ethylene/propylene copolymers with a range of known wt % ethylene content.

General Procedure for Propylene Polymerization with Supported Catalyst in 2 L Reactor The supported catalyst is slurried into dry Hydrobrite™ oil to yield a slurry containing 5 wt. % of supported catalyst. A 2 L autoclave reactor is charged with propylene (600 mL), hydrogen (provided from a 183 mL container under pressure under the pressure indicated in Table 3) and tri-n-octylaluminum, 1.0 mL of a 4.76 vol. % hexane solution. Thereafter, the reactor temperature is raised to 70° C. The desired amount of supported catalyst-containing slurry is then injected into the reactor together with 200 mL of propylene. The polymerization is allowed to proceed for a predetermined period, typically 60 min. The reactor is then cooled and vented.

Melt Flow Rate (MFR) is determined in accordance with ASTM D-1238 under a load of 2.16 kg and at a temperature of 230° C. (i.e., Condition L).

Mw, Mn and Mw/Mn are determined by using a High Temperature Gel Permeation Chromatography (Polymer Laboratories), equipped with a differential refractive index detector (DRI). Three Polymer Laboratories PLgel 10 μm Mixed-B columns are used. The nominal flow rate is 1.0 mL/min, and the nominal injection volume is 300 μL. The various transfer lines, columns, and differential refractometer (the DRI detector) are contained in an oven maintained at 160° C. Solvent for the experiment is prepared by dissolving 6 grams of butylated hydroxytoluene as an antioxidant in 4 liters of Aldrich reagent grade 1, 2, 4 trichlorobenzene (TCB). The TCB mixture is then filtered through a 0.1 μm Teflon filter. The TCB is then degassed with an online degasser before entering the GPC instrument. Polymer solutions are prepared by placing dry polymer in glass vials, adding the desired amount of TCB, then heating the mixture at 160° C. with continuous shaking for about 2 hours. All quantities are measured gravimetrically. The injection concentration is from 0.5 to 2.0 mg/ml, with lower concentrations being used for higher molecular weight samples. Prior to running each sample, the DRI detector is purged. Flow rate in the apparatus is then increased to 1.0 ml/minute, and the DRI is allowed to stabilize for 8 hours before injecting the first sample. The molecular weight is determined by combining universal calibration relationship with the column calibration which is performed with a series of monodispersed polystyrene (PS) standards. The MW is calculated at each elution volume with following equation:

$$\log M_X = \frac{\log(K_X/K_{PS})}{a_X+1} + \frac{a_{PS}+1}{a_X+1}\log M_{PS}$$

where the variables with subscript "X" stand for the test sample while those with subscript "PS" stand for polystyrene. In this method, $a_{PS}$=0.67 and $K_{PS}$=0.000175 while $a_X$ and $K_X$ are obtained from published literature. Specifically, a and K=0.695 and 0.000579 for ethylene polymer and 0.705 and 0.0002288 for propylene polymer.

The concentration, c, at each point in the chromatogram is calculated from the baseline-subtracted DRI signal, $I_{DRI}$, using the following equation:

$$c = K_{DRI}I_{DRI}/(dn/dc)$$

where $K_{DRI}$ is a constant determined by calibrating the DRI, and (dn/dc) is the refractive index increment for the system. Specifically, dn/dc=0.109 for both propylene polymer and ethylene polymer.

The mass recovery is calculated from the ratio of the integrated area of the concentration chromatography over elution volume and the injection mass, which is equal to the pre-determined concentration multiplied by injection loop volume.

All molecular weights are reported in g/mol unless otherwise noted. In the event of conflict between the GPC-DRI procedure and the "Rapid GPC," the GPC-DRI procedure immediately above shall be used. Further details regarding methods of determining Mw, Mn, MWD are described in US 2006/0173123 pages 24-25, paragraphs [0334] to [0341].

Differential Scanning calorimetry (DSC-Procedure-2). Melting Temperature, $T_m$, is measured by differential scanning calorimetry ("DSC") using a DSCQ200 unit. The sample is first equilibrated at 25° C. and subsequently heated to 220° C. using a heating rate of 10° C./min (first heat). The sample is held at 220° C. for 3 min. The sample is subsequently cooled down to −100° C. with a constant cooling rate of 10° C./min (first cool). The sample is equilibrated at −100° C. before being heated to 220° C. at a constant heating rate of 10° C./min (second heat). The exothermic peak of crystallization (first cool) is analyzed using the TA Universal Analysis software and the corresponding to 10° C./min cooling rate is determined The endothermic peak of melting (second heat) is also analyzed using the TA Universal Analysis software and the peak melting temperature ($T_m$) corresponding to 10° C./min heating rate is determined. In the event of conflict between the DSC Procedure-1 and DSC procedure-2, DSC procedure-2 shall be used.

1% Secant flexural modulus is measured using an ISO 37-Type 3 bar, with a crosshead speed of 1.0 mm/min and a support span of 30.0 mm using an Instron machine according to ASTM D 790 (A, 1.0 mm/min)

Polymerization data are reported in Tables 1-5.

TABLE 1

Small Scale Solution Propylene Polymerization Using 0.025 μmol of Catalyst and 500 molar equivalents of MAO. Conditions: isohexane solvent, total volume = 5 mL.

| Example | Catalyst | $T_p$ (° C.) | Propylene (mmol) | $M_n$ (kg/mol) | $M_w$ (kg/mol) | $M_w/M_n$ | $T_m$ (° C.) | Quench Time (sec) | Yield (g) | Activity (g/mmol · hr) |
|---|---|---|---|---|---|---|---|---|---|---|
| 1 | 1 | 50 | 4.777 | 564 | 1173 | 2.1 | 160.7 | 148 | 0.1718 | 167157 |
| 2 | 1 | 50 | 9.553 | 564 | 1370 | 2.4 | 160.2 | 143 | 0.2426 | 244267 |
| 3 | 2 | 50 | 4.777 | 303 | 632 | 2.1 | 157.0 | 84 | 0.1501 | 257314 |
| 4 | 2 | 50 | 9.553 | 188 | 572 | 3.0 | 158.0 | 124 | 0.3358 | 389961 |
| 5 | 3 | 50 | 4.777 | 348 | 640 | 1.8 | 161.2 | 118 | 0.1179 | 143878 |
| 6 | 3 | 50 | 9.553 | 229 | 568 | 2.5 | 159.9 | 126 | 0.2592 | 296229 |
| 7 | 1 | 70 | 4.777 | 354 | 643 | 1.8 | 158.7 | 93 | 0.1174 | 181781 |
| 8 | 1 | 70 | 9.553 | 226 | 589 | 2.6 | 157.6 | 122 | 0.2683 | 316682 |
| 9 | 2 | 70 | 4.777 | 146 | 298 | 2.0 | 155.8 | 73 | 0.1129 | 222707 |
| 10 | 2 | 70 | 9.553 | 141 | 331 | 2.3 | 155.4 | 64 | 0.2159 | 485775 |
| 11 | 3 | 70 | 4.777 | 145 | 292 | 2.0 | 157.8 | 94 | 0.1102 | 168817 |
| 12 | 3 | 70 | 9.553 | 130 | 295 | 2.3 | 157.2 | 92 | 0.2016 | 315548 |
| 13 | 1 | 100 | 4.777 | 83 | 163 | 2.0 | 152.6 | 97 | 0.0787 | 116833 |
| 14 | 1 | 100 | 9.553 | 103 | 196 | 1.9 | 153.3 | 76 | 0.1199 | 227179 |
| 15 | 2 | 100 | 4.777 | 37 | 69 | 1.9 | 148.8 | 63 | 0.0751 | 171657 |
| 16 | 2 | 100 | 9.553 | 45 | 91 | 2.1 | 150.3 | 56 | 0.1208 | 310629 |
| 17 | 3 | 100 | 4.777 | 44 | 84 | 1.9 | 148.8 | 126 | 0.0707 | 80800 |
| 18 | 3 | 100 | 9.553 | 57 | 104 | 1.8 | 150.8 | 88 | 0.1047 | 171327 |

TABLE 2

Small Scale Solution Propylene Polymerization Using 0.025 μmol of Catalyst 1 or 7 and 500 molar equivalents of MAO. Conditions: isohexane solvent, propylene (introduced to each vessel as gas) added = 9.553 mmol, total volume = 5 mL.

| Example | Catalyst | Tp (° C.) | Mw (kg/mol) | Mw/Mn | Tm (° C.) | Quench Time (sec) | Yield (g) | Activity (g/mmol · hr) | Average Activity (g/mmol · hr) | Average Tm (° C.) | Average Mw (kg/mol) |
|---|---|---|---|---|---|---|---|---|---|---|---|
| 19 | 1 | 50 | 1755 | 2.5 | 159.7 | 187 | 0.1937 | 149159 | | | |
| 20 | 1 | 50 | 1631 | 2.3 | 158.9 | 196 | 0.194 | 142531 | | | |
| 21 | 1 | 50 | 1603 | 2.2 | 160.5 | 185 | 0.186 | 144778 | | | |
| 22 | 1 | 50 | 1431 | 2.8 | 158.7 | 270 | 0.2808 | 149760 | 146557 | 159.5 | 1605 |
| 23 | 7 | 50 | 1722 | 1.9 | 160.4 | 268 | 0.2402 | 129063 | | | |
| 24 | 7 | 50 | 1414 | 2.6 | 158.4 | 315 | 0.2632 | 120320 | | | |
| 25 | 7 | 50 | 1837 | 2.7 | 159.5 | 208 | 0.158 | 109385 | | | |
| 26 | 7 | 50 | 1295 | 3.0 | 158.9 | 312 | 0.2904 | 134031 | 123200 | 159.3 | 1567 |
| 27 | 1 | 70 | 668 | 2.2 | 157.9 | 127 | 0.2023 | 229380 | | | |
| 28 | 1 | 70 | 622 | 2.4 | 158.2 | 116 | 0.2163 | 268510 | | | |
| 29 | 1 | 70 | 741 | 2.3 | 157.4 | 125 | 0.2021 | 232819 | | | |
| 30 | 1 | 70 | 628 | 2.5 | 157.9 | 128 | 0.2467 | 277538 | 252062 | 157.9 | 665 |
| 31 | 7 | 70 | 621 | 2.3 | 157.2 | 146 | 0.2382 | 234937 | | | |
| 32 | 7 | 70 | 685 | 2.3 | 157.2 | 127 | 0.2418 | 274167 | | | |
| 33 | 7 | 70 | 810 | 2.1 | 157.4 | 115 | 0.1599 | 200223 | | | |
| 34 | 7 | 70 | 715 | 2.0 | 157.2 | 118 | 0.2138 | 260908 | 242559 | 157.3 | 708 |

TABLE 3

Propylene Polymerization with Supported Catalyst A in 2 L Reactor

| Example | Catalyst | Catalyst Amount (g) | Run Time (min) | $H_2$ Pressure (psi) | Yield (g) | Activity ($g_{polymer}/g_{cat}*hr$) | Primary $T_m$ (° C.) | MFR (dg/min) | 1% Sec. Modulus (MPa) | $M_w$ (kg/mol) | $M_w/M_n$ (kg/mol) |
|---|---|---|---|---|---|---|---|---|---|---|---|
| 35 | A | 0.0178 | 60 | 5 | 35.22 | 1979 | 158.2 | 2.1 | 1677 | | |
| 36 | A | 0.0177 | 60 | 0 | 6.83 | 384 | 154.8 | <0.085 | | 1328 | 2.76 |
| 37 | A | 0.1207 | 60 | 0 | 52.98 | 439 | | 0.108 | 1618 | | |
| 38 | A | 0.0179 | 60 | 10 | 24.77 | 1384 | 156.9 | 2.2 | 1643 | 614 | 3.84 |
| 39 | A | 0.0178 | 60 | 20 | 54.16 | 3043 | 157.3 | 52 | 1148 | 179 | 3.22 |

TABLE 4

Small Scale Ethylene Propylene Copolymerization Using 0.39 mg of Supported Catalysts. Conditions: isohexane solvent, propylene (introduced to each vessel as gas) added = 9.553 mmol, TONAL = 4 μmol, total volume = 5 mL.

| Example | Catalyst | Quench Time(s) | Yield (mg) | gPolymer/ gcat sup · hr | Mw (kg/mol) | Mw/ Mn | C2 wt % | Average Mw (kg/mol) | $T_m$ (° C.) |
|---|---|---|---|---|---|---|---|---|---|
| 40 | Catalyst B (comparative) | 2701 | 21.4 | 73 | 1054 | 2.6 | 0 | 996 | 153.0 |
| 41 | | 786 | 108.2 | 1271 | 216 | 2.3 | 13.3 | 224 | |
| 42 | | 257 | 116.7 | 4192 | 166 | 2.2 | 20.2 | 171 | |
| 43 | | 170 | 120.2 | 6527 | 181 | 2.4 | 27.0 | 180 | |
| 44 | | 138 | 120.7 | 8074 | 213 | 2.1 | 31.8 | 210 | |
| 45 | | 95 | 151.3 | 14701 | 239 | 2.1 | 40.3 | 249 | |
| 46 | | 2700 | 22.4 | 77 | 938 | 3.1 | 0 | | 153.4 |
| 47 | | 2183 | 106.8 | 452 | 231 | 2.2 | 13.2 | | |
| 48 | | 317 | 131.5 | 3829 | 175 | 2.2 | 19.7 | | |
| 49 | | 205 | 141.6 | 6376 | 179 | 2.4 | 25.7 | | |
| 50 | | 160 | 131.5 | 7587 | 206 | 2.2 | 30.3 | | |
| 51 | | 105 | 146.5 | 12879 | 258 | 2.3 | 40.0 | | |
| 52 | Catalyst A | 2700 | 18.8 | 64 | 1073 | 3.4 | 0 | 1076 | 153.9 |
| 53 | | 2701 | 73.8 | 252 | 364 | 2.4 | 13.7 | 352 | |
| 54 | | 2700 | 85.8 | 293 | 306 | 2.5 | 20.5 | 312 | |
| 55 | | 345 | 98.3 | 2630 | 272 | 2.5 | 25.9 | 276 | |
| 56 | | 176 | 95 | 4983 | 315 | 2.1 | 34.7 | 327 | |
| 57 | | 2701 | 64.1 | 219 | 347 | 2.1 | 46.8 | 351 | |
| 58 | | 2700 | 15.4 | 53 | 1078 | 3.0 | 0 | | 153.7 |
| 59 | | 2701 | 32.8 | 112 | 339 | 2.4 | 13.7 | | |
| 60 | | 2700 | 33.2 | 114 | 318 | 2.3 | 24.4 | | |
| 61 | | 221 | 98.8 | 4127 | 280 | 2.9 | 25.5 | | |
| 62 | | 1673 | 76.3 | 421 | 339 | 2.3 | 35.7 | | |
| 63 | | 131 | 90.7 | 6391 | 355 | 2.3 | 37.5 | | |
| 64 | Catalyst D (comparative) | 2701 | 37.1 | 127 | 449 | 2.9 | 0 | 441 | 153.3 |
| 65 | | 533 | 126.1 | 2184 | 86 | 2.0 | 12 | 88 | |
| 66 | | 280 | 126.5 | 4170 | 77 | 2.4 | 19.3 | 79 | |
| 67 | | 287 | 139.3 | 4480 | 82 | 2.2 | 28.3 | 84 | |
| 68 | | 165 | 152.9 | 8554 | 99 | 2.6 | 34.4 | 99 | |
| 69 | | 110 | 192.2 | 16129 | 136 | 2.0 | 46.8 | 134 | |
| 70 | | 2700 | 36 | 123 | 433 | 2.5 | 0 | | 152.6 |
| 71 | | 509 | 125.8 | 2281 | 90 | 2.8 | 14.4 | | |
| 72 | | 306 | 143.6 | 4332 | 81 | 1.9 | 20.3 | | |
| 73 | | 238 | 150.9 | 5853 | 85 | 2.1 | 26.6 | | |
| 74 | | 188 | 194.2 | 9535 | 99 | 2.3 | 30.9 | | |
| 75 | | 108 | 185.5 | 15855 | 131 | 2.0 | 42 | | |
| 76 | Catalyst C | 2700 | 49.3 | 169 | 444 | 3.1 | 0 | 435 | 153.3 |
| 77 | | 425 | 114.5 | 2487 | 110 | 2.4 | 13.6 | 119 | |
| 78 | | 245 | 130.9 | 4932 | 110 | 2.0 | 23.5 | 113 | |
| 79 | | 149 | 159.7 | 9894 | 136 | 1.9 | 27.5 | 130 | |
| 80 | | 130 | 219 | 15550 | 155 | 2.0 | 37 | 156 | |
| 81 | | 77 | 223.3 | 26769 | 191 | 2.3 | 45.9 | 196 | |
| 82 | | 2701 | 51.8 | 177 | 425 | 3.0 | 0 | | 154.6 |
| 83 | | 454 | 136.6 | 2777 | 128 | 2.4 | 11.7 | | |
| 84 | | 257 | 146.2 | 5251 | 115 | 2.3 | 20.4 | | |
| 85 | | 159 | 163.7 | 9504 | 124 | 1.9 | 28.5 | | |
| 86 | | 138 | 213.1 | 14254 | 156 | 2.1 | 36.2 | | |
| 87 | | 88 | 296.2 | 31070 | 201 | 2.2 | 42.8 | | |

TABLE 5

Small Scale Ethylene Propylene Copolymerization Using 0.39 mg of Supported Catalysts.
Conditions: isohexane solvent, propylene (introduced to each vessel as gas)
added = 9.553 mmol, TONAL = 0.4 μmol, total volume = 5 mL.

| Example | Catalyst | Quench Time(s) | Yield (mg) | gPolymer/ gcat- sup · hr | Mw (kg/mol) | Mw/ Mn | C2 wt % | Average Mw (kg/mol) | $T_m$ (° C.) |
|---|---|---|---|---|---|---|---|---|---|
| 88 | Catalyst F (comparative) | 2700 | 24.6 | 84 | 998 | 2.6 | 0 | 991 | 151.5 |
| 89 | | 1070 | 116.7 | 1007 | 258 | 2.1 | 11.5 | 251 | |
| 90 | | 417 | 107.8 | 2386 | 169 | 2.2 | 18.8 | 172 | |
| 91 | | 216 | 135.2 | 5778 | 196 | 2.0 | 28.3 | 196 (one datum) | |
| 92 | | 281 | 103.2 | 3390 | 238 | 1.9 | 33.1 | 238 (one datum) | |
| 93 | | 2702 | 24.4 | 83 | 984 | 2.9 | 0 | | 151.8 |
| 94 | | 832 | 118.5 | 1315 | 244 | 2.2 | 11.6 | | |
| 95 | | 313 | 125.4 | 3698 | 174 | 2.2 | 17.6 | | |
| 96 | Catalyst E | 2702 | 26.1 | 89 | 972 | 3.5 | 0 | 939 | 151.5 |
| 97 | | 2095 | 113.1 | 498 | 254 | 2.4 | 12.4 | 272 | |
| 98 | | 388 | 115.4 | 2745 | 198 | 2.3 | 17.9 | 209 | |
| 99 | | 231 | 106.8 | 4268 | 217 | 2.2 | 28.7 | 218 | |
| 100 | | 262 | 80.7 | 2843 | 261 | 2.0 | 35.5 | 252 | |
| 101 | | 2701 | 22.2 | 76 | 905 | 4.3 | 0 | | 151.8 |
| 102 | | 2702 | 101.8 | 348 | 290 | 2.9 | 13.0 | | |
| 103 | | 408 | 108.8 | 2462 | 219 | 2.4 | 18.1 | | |
| 104 | | 190 | 119.5 | 5806 | 219 | 2.1 | 27.3 | | |
| 105 | | 155 | 131.8 | 7849 | 242 | 2.1 | 34.8 | | |

Figure 2:
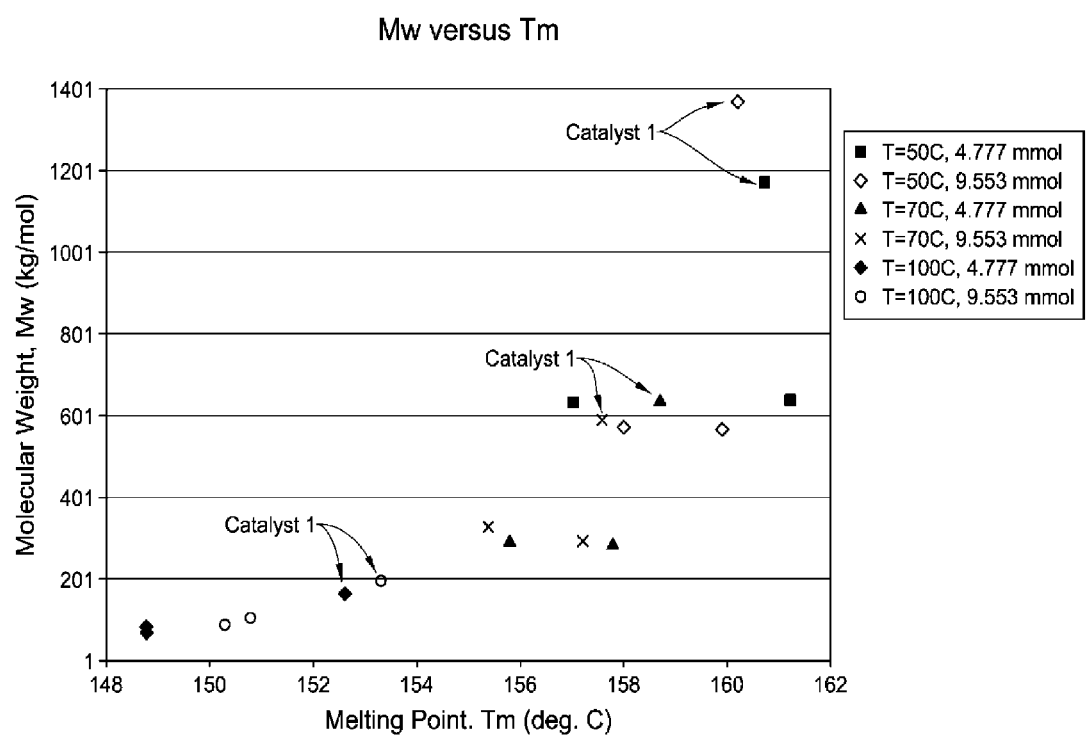
FIG. 2 is a graphical representation of the molecular weight versus melting point of polypropylenes.
Figure 3:
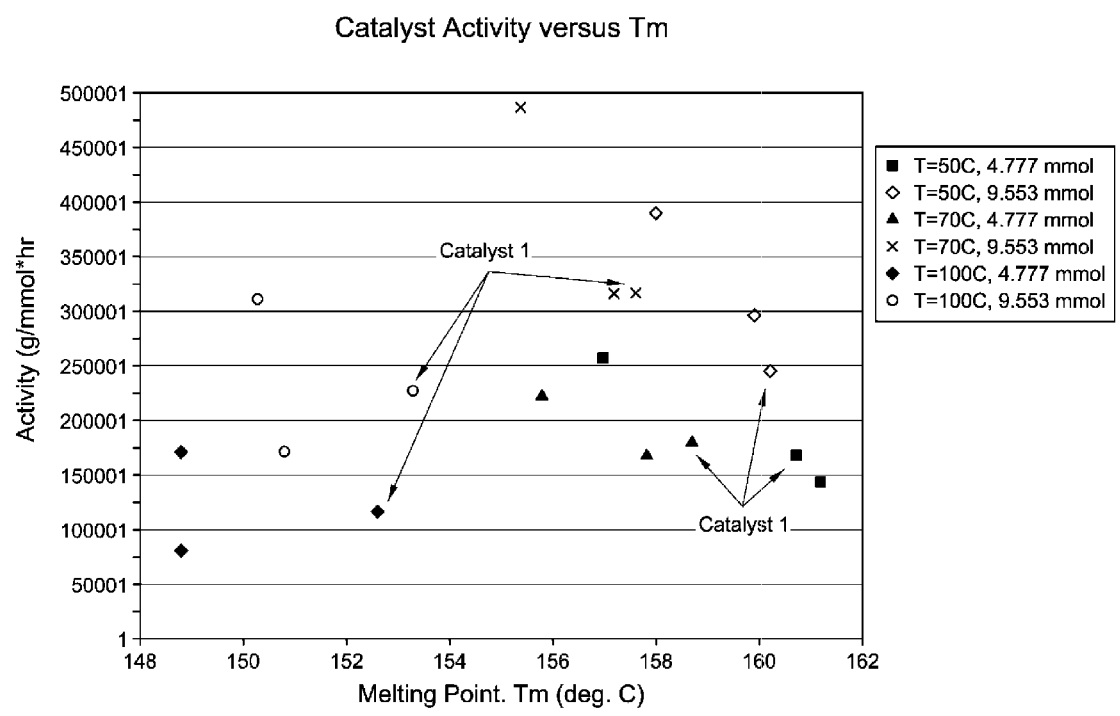
FIG. 3 is a graphical representation of the catalyst activity versus melting point of polypropylenes.

As illustrated in FIG. 2, the polymers made with Catalyst 1 have high melting points as well as high molecular weight. FIG. 3 illustrates that Catalyst 1 strikes a balance between catalyst activity and higher melting point. In other words, the melting point of the polymer may be increased without reduction in the catalyst activity.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law. Likewise whenever a composition, an element or a group of elements is preceded with the transitional phrase "comprising", it is understood that we also contemplate the same composition or group of elements with transitional phrases "consisting essentially of," "consisting of", "selected from the group of consisting of," or "is" preceding the recitation of the composition, element, or elements and vice versa.

What is claimed is:

1. A transition metal complex for use in alkene polymerization represented by the formula (I):

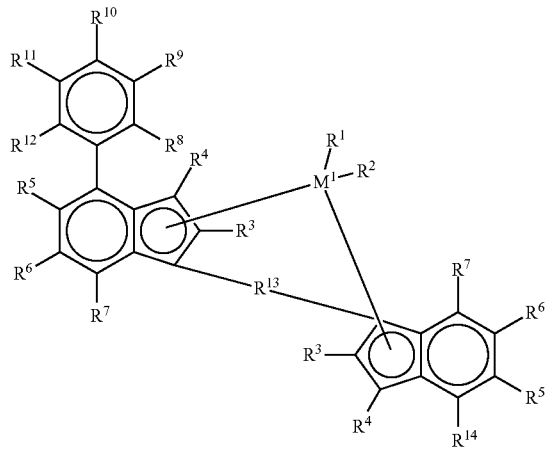

(I)

wherein $M^1$ is selected from the group consisting of titanium, zirconium, hafnium, vanadium, niobium, tantalum, chromium, molybdenum and tungsten;

$R^1$ and $R^2$ are identical or different, and are each a hydrogen atom, a $C_1$-$C_{10}$ alkyl group, a $C_1$-$C_{10}$ alkoxy group, a $C_6$-$C_{10}$ aryl group, a $C_6$-$C_{10}$ aryloxy group, a $C_2$-$C_{10}$ alkenyl group, a $C_2$-$C_{40}$ alkenyl group, a $C_7$-$C_{40}$ arylalkyl group, a $C_7$-$C_{40}$ alkylaryl group, a $C_8$-$C_{40}$ arylalkenyl group, an OH group or a halogen atom, or a conjugated diene which is optionally substituted with one or more hydrocarbyl, tri (hydrocarbyl) silyl groups or tri (hydrocarbyl) silylhydrocarbyl groups, said diene having up to 30 atoms not counting hydrogen;

$R^3$ to $R^7$ are identical or different and are each a hydrogen atom, a halogen atom, a $C_1$-$C_{10}$ alkyl group which is optionally halogenated, a $C_6$-$C_{10}$ aryl group which is optionally halogenated, a $C_2$-$C_{10}$ alkenyl group, a $C_7$-$C_{40}$ arylalkyl group, a $C_7$-$C_{40}$ alkylaryl group, a $C_8$-$C_{40}$ arylalkenyl group, a —$NR'_2$, —SR', —OR, —$OSiR'_3$ or —$PR'_2$ radical, wherein R' is one of a hydrogen atom, halogen atom, a $C_1$-$C_{10}$ alkyl group, or a $C_6$-$C_{10}$ aryl group or two or more adjacent radicals $R^5$ to $R^7$ together with the atoms of the indenyl group connecting them form one or more rings;

$R^{13}$ is —$B(R^{15})$—, —$Al(R^{15})$—, —O—, —S—, —SO—, —SO2-, —$N(R^{15})$—, —CO—, —$P(R^{15})$—, or —$P(O)(R^{15})$—, an amidoborane radical or meets one of the following:

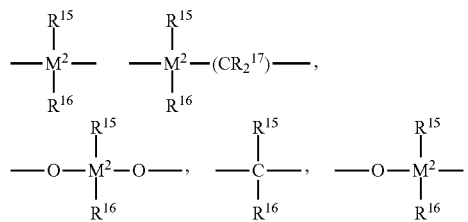

wherein $R^{15}$, $R^{16}$, $R^{17}$ are identical or different and are a hydrogen atom, a halogen atom, a $C_1$-$C_{20}$ alkyl group, a $C_1$-$C_{20}$ fluoroalkyl or silaalkyl group, a $C_6$-$C_{30}$ aryl group, a $C_6$-$C_{30}$ fluoroaryl group, a $C_1$-$C_{20}$ alkoxy group, a $C_2$-$C_{20}$ alkenyl group, a $C_7$-$C_{40}$ arylalkyl group, a $C_8$-$C_{40}$ arylalkenyl group, a $C_7$-$C_{40}$ alkylaryl group, or one $R^{15}$ and one $R^{16}$, together with the atoms in $R^{13}$ connecting them, form a ring; $M^2$ is one or more of carbon, silicon, germanium or tin;

$R^8$ and $R^{12}$ are identical or different and are each a hydrogen atom, a halogen atom, a $C_3$-$C_{10}$ alkyl group which is optionally halogenated, a $C_6$-$C_{10}$ aryl group which is optionally halogenated, a $C_2$-$C_{10}$ alkenyl group, a $C_7$-$C_{40}$ arylalkyl group, a $C_7$-$C_{40}$ alkylaryl group, a $C_8$-$C_{40}$ arylalkenyl group, a —$NR'_2$, —SR', —OR, —$OSiR'_3$ or —$PR'_2$ radical, wherein R' is one of a hydrogen atom, halogen atom, a $C_1$-$C_{10}$ alkyl group, or a $C_6$-$C_{10}$ aryl group;

$R^9$ and $R^{11}$ are identical or different and selected from $C_2$-$C_{20}$ alkyl group which is optionally halogenated, a $C_6$-$C_{10}$ aryl group which is optionally halogenated, a $C_2$-$C_{10}$ alkenyl group, a $C_7$-$C_{20}$ arylalkyl group, a $C_7$-$C_{20}$ alkylaryl group, a $C_8$-$C_{20}$ arylalkenyl group;

$R^{10}$ is selected from $(XR'_n)^-$, wherein X is a Group 14-17 heteroatom having an atomic weight of 13 to 79 and R' is one of a hydrogen atom, halogen atom, a $C_1$-$C_{10}$ alkyl group, or a $C_6$-$C_{10}$ aryl group and n is 0, 1, 2, or 3; and $R^{14}$ is an unsubstituted phenyl or a substituted phenyl, where the substituted phenyl is:
1) substituted at the 3' and 5' positions by radicals which are identical or different and selected from $C_2$-$C_{20}$ alkyl group which is optionally halogenated, a $C_6$-$C_{10}$ aryl group which is optionally halogenated, a $C_2$-$C_{10}$ alkenyl group, a $C_7$-$C_{20}$ arylalkyl group, a $C_7$-$C_{20}$ alkylaryl group, a $C_8$-$C_{20}$ arylalkenyl group, or
2) substituted at the 2-position by an $R^{3'}$ group, wherein $R^{3'}$ is a halogen atom, a $C_1$-$C_{10}$ alkyl group which is optionally halogenated, a $C_6$-$C_{10}$ aryl group which is optionally halogenated, a $C_2$-$C_{10}$ alkenyl group, a $C_7$-$C_{40}$ arylalkyl group, a $C_7$-$C_{40}$ alkylaryl group, a $C_8$-$C_{40}$ arylalkenyl group, a —$NR'_2$, —SR', —OR', —$OSiR'_3$ or —$PR'_2$ radical, wherein R is one of a halogen atom, a $C_1$-$C_{10}$ alkyl group, or a $C_6$-$C_{10}$ aryl group.

2. The transition metal complex of claim 1, wherein $R^{10}$ is —$NR'_2$, —SR', —OR', —$OSiR'_3$, —$SiR'_3$, or —$PR'_2$, wherein R' is one of a hydrogen atom, halogen atom, a $C_1$-$C_{10}$ alkyl group, or a $C_6$-$C_{10}$ aryl group.

3. The transition metal complex of claim 1, wherein $R^{10}$ is selected from —$NR'_2$, —SR', —OR', —$OSiR'_3$, or —$PR'_2$, wherein R' is one of a hydrogen atom, halogen atom, a $C_1$-$C_{10}$ alkyl group, or a $C_6$-$C_{10}$ aryl group.

4. The transition metal complex of claim 1, wherein $R^{10}$ is —SR', —OR', or —$OSiR'_3$, wherein R' is one of a hydrogen atom, halogen atom, a $C_1$-$C_{10}$ alkyl group, or a $C_6$-$C_{10}$ aryl group.

5. The transition metal complex of claim 1, wherein $R^{10}$ is —$NR'_2$ or —$PR'_2$ radical, wherein R' is one of a hydrogen atom, halogen atom, a $C_1$-$C_{10}$ alkyl group, or a $C_6$-$C_{10}$ aryl group.

6. The transition metal complex of claim 1, wherein $R^3$ is a $C_1$-$C_{10}$ alkyl group or a $C_6$-$C_{10}$ aryl group.

7. The transition metal complex of claim 1, wherein $R^9$ and $R^{11}$ are each selected from the group consisting of n-butyl, iso-butyl, and tert-butyl groups and $R^{10}$ is OR' wherein R' is a $C_1$-$C_{10}$ alkyl group.

8. A transition metal complex for use in alkene polymerization represented by the formula (II):

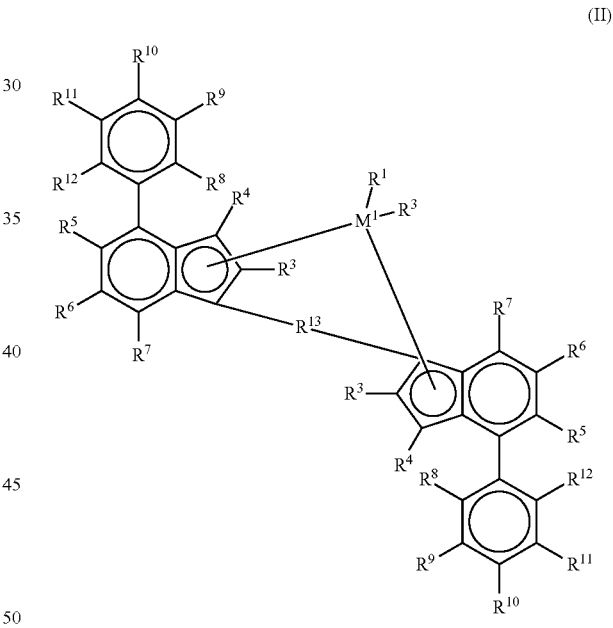

(II)

wherein $M^1$ is selected from the group consisting of titanium, zirconium, hafnium, vanadium, niobium, tantalum, chromium, molybdenum, and tungsten;

$R^1$ and $R^2$ are identical or different, and are each a hydrogen atom, a $C_1$-$C_{10}$ alkyl group, a $C_1$-$C_{10}$ alkoxy group, a $C_6$-$C_{10}$ aryl group, a $C_6$-$C_{10}$ aryloxy group, a $C_2$-$C_{10}$ alkenyl group, a $C_2$-$C_{40}$ alkenyl group, a $C_7$-$C_{40}$ arylalkyl group, a $C_7$-$C_{40}$ alkylaryl group, a $C_8$-$C_{40}$ arylalkenyl group, an OH group or a halogen atom, or a conjugated diene which is optionally substituted with one or more hydrocarbyl, tri (hydrocarbyl) silyl groups or tri (hydrocarbyl) silylhydrocarbyl groups, said diene having up to 30 atoms not counting hydrogen;

$R^3$ to $R^7$ are identical or different and are each a hydrogen atom, a halogen atom, a $C_1$-$C_{10}$ alkyl group which is optionally halogenated, a $C_6$-$C_{10}$ aryl group which is optionally halogenated, a $C_2$-$C_{10}$ alkenyl group, a $C_7$-$C_{40}$ arylalkyl group, a $C_7$-$C_{40}$ alkylaryl group, a $C_8$-$C_{40}$ arylalkenyl group, a —NR'$_2$, —SR', —OR, —OSiR'$_3$ or —PR'$_2$ radical, wherein R' is one of a hydrogen atom, halogen atom, a $C_1$-$C_{10}$ alkyl group, or a $C_6$-$C_{10}$ aryl group or two or more adjacent radicals $R^5$ to $R^7$ together with the atoms of the indenyl group connecting them form one or more rings;

$R^{13}$ is —B($R^{15}$)—, —Al($R^{15}$)—, —O—, —S—, —SO—, —SO2-, —N($R^{15}$)—, —CO—, —P($R^{15}$)—, or —P(O)($R^{15}$)—, an amidoborane radical or meets one of the following:

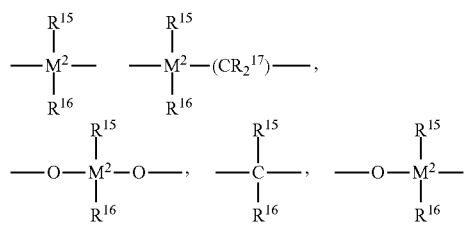

wherein $R^{15}$, $R^{16}$, $R^{17}$ are identical or different and are a hydrogen atom, a halogen atom, a $C_1$-$C_{20}$ alkyl group, a $C_1$-$C_{20}$ fluoroalkyl or silaalkyl group, a $C_6$-$C_{30}$ aryl group, a $C_6$-$C_{30}$ fluoroaryl group, a $C_1$-$C_{20}$ alkoxy group, a $C_2$-$C_{20}$ alkenyl group, a $C_7$-$C_{40}$ arylalkyl group, a $C_8$-$C_{40}$ arylalkenyl group, a $C_7$-$C_{40}$ alkylaryl group, or one $R^{15}$ and one $R^{16}$, together with the atoms in $R^{13}$ connecting them form a ring, $M^2$ is one or more of carbon, silicon, germanium or tin;

each $R^8$ and $R^{12}$ are identical or different and are each a hydrogen atom, a halogen atom, a $C_3$-$C_{10}$ alkyl group which is optionally halogenated, a $C_6$-$C_{10}$ aryl group which is optionally halogenated, a $C_2$-$C_{10}$ alkenyl group, a $C_7$-$C_{40}$ arylalkyl group, a $C_7$-$C_{40}$ alkylaryl group, a $C_8$-$C_{40}$ arylalkenyl group, a —NR'$_2$, —SR', —OR, —OSiR'$_3$ or —PR'$_2$ radical, wherein R' is one of a hydrogen atom, halogen atom, a $C_1$-$C_{10}$ alkyl group, or a $C_6$-$C_{10}$ aryl group;

each $R^9$ and $R^{11}$ are identical or different and are each a $C_2$-$C_{20}$ alkyl group which is optionally halogenated, a $C_6$-$C_{10}$ aryl group which is optionally halogenated, a $C_2$-$C_{10}$ alkenyl group, a $C_7$-$C_{20}$ arylalkyl group, a $C_7$-$C_{20}$ alkylaryl group, or a $C_8$-$C_{20}$ arylalkenyl group; and each $R^{10}$ is individually selected from (XR'$_n$)$^-$, wherein X is a Group 14-17 heteroatom having an atomic weight of 13 to 79 and R' is one of a hydrogen atom, halogen atom, a $C_1$-$C_{10}$ alkyl group, or a $C_6$-$C_{10}$ aryl group and n is 0, 1 2, or 3.

9. The transition metal complex of claim 8, wherein each $R^{10}$ is individually —NR'$_2$, —SR', —OR', —OSiR'$_3$, —SiR'$_3$, or —PR'$_2$, wherein R' is one of a hydrogen atom, halogen atom, a $C_1$-$C_{10}$ alkyl group, or a $C_6$-$C_{10}$ aryl group.

10. The transition metal complex of claim 8, wherein each $R^{10}$ is individually —NR'$_2$, —SR', —OR', —OSiR'$_3$, or —PR'$_2$, wherein R' is one of a hydrogen atom, halogen atom, a $C_1$-$C_{10}$ alkyl group, or a $C_6$-$C_{10}$ aryl group.

11. The transition metal complex of claim 8, wherein each $R^{10}$ is individually —SR', —OR', or —OSiR'$_3$, wherein R' is one of a hydrogen atom, halogen atom, a $C_1$-$C_{10}$ alkyl group, or a $C_6$-$C_{10}$ aryl group.

12. The transition metal complex of claim 9, wherein each $R^{10}$ is individually —NR'$_2$ or —PR'$_2$ radical, wherein R' is one of a hydrogen atom, halogen atom, a $C_1$-$C_{10}$ alkyl group, or a $C_6$-$C_{10}$ aryl group.

13. The transition metal complex of claim 8, wherein each $R^9$ and each $R^{11}$ is selected from the group consisting of n-butyl, iso-butyl, and tert-butyl groups and each $R^{10}$ is OR' wherein R' is a $C_1$-$C_{10}$ alkyl group.

14. The transition metal complex of claim 8, wherein each $R^1$ and $R^2$ are the same or different and are each a halogen atom;
   wherein each $R^3$ are the same or different and are each a $C_1$-$C_{10}$ alkyl group;
   wherein each $R^4$, $R^5$, $R^6$, and $R^7$ are the same or different and are each a hydrogen atom or $C_1$-$C_{10}$ alkyl group; and
   wherein each $R^8$ and $R^{12}$ are each a hydrogen atom; $R^{13}$ is —SiR''$_2$— wherein each R'' are the same or different and are each a hydrogen or methyl; wherein each $R^9$ and $R^{11}$ is a tert-butyl group; and wherein each $R^{10}$ is a methoxy group.

15. A catalyst system comprising an activator and the transition metal complex of claim 1.

16. The catalyst system of claim 15, wherein the activator comprises an alumoxane.

17. The catalyst system of claim 15, wherein the activator comprises a non-coordinating anion.

18. A polymerization process comprising a) contacting one or more alkene monomers with a catalyst system comprising: i) an activator and ii) the transition metal complex of claim 1.

19. The process of claim 18, wherein the activator comprises an alumoxane.

20. The process of claim 18, wherein the activator comprises a non-coordinating anion.

21. The process of claim 18, wherein the one or more alkene monomers comprises propylene.

22. The process of claim 18, wherein the catalyst compound is supported.

23. The process of claim 18 further comprising obtaining polymer.

24. The process of claim 23, wherein the polymer comprises a polypropylene having a melting point of 152.0° C. to about 162.0° C., an $M_w$ 60,000 to 1,400,000 g/mol; and an Mw/Mn of 1.5 to 3.5.

25. A bridged bis(4-phenyl-indenyl) transition metal complex wherein:
   at least one of the 4-phenyl rings being substituted at the 3' and 5' positions by radicals which are identical or different and selected from $C_2$-$C_{20}$ alkyl groups which are optionally halogenated, a $C_6$-$C_{10}$ aryl group which is optionally halogenated, a $C_2$-$C_{10}$ alkenyl group, a $C_7$-$C_{40}$ arylalkyl group, a $C_7$-$C_{20}$ alkylaryl group, a $C_8$-$C_{20}$ arylalkenyl group;
   wherein both of the phenyl rings substituted at the 3' and 5' positions are also substituted at the 4' position with a group of the formula (XR'$_n$)$^-$, wherein X is a Group 14-17 heteroatom having an atomic weight of 13 to 79 and R' is one of a hydrogen atom, halogen atom, a $C_1$-$C_{10}$ alkyl group, or a $C_6$-$C_{10}$ aryl group and n is 0, 1, 2 or 3; and
   optionally, wherein one or more of the remaining positions on the phenyl and/or indenyl ring(s) of the transition metal complex are substituted.

26. The transition metal complex of claim 1, wherein $R^3$ is selected from hydrogen and cyclopropyl; each of $R^9$ and $R^{11}$ is selected from the group consisting of n-butyl, isobutyl, and tert-butyl groups; and $R^{10}$ is a methoxy, ethoxy, n-propoxy, isopropoxy, n-butoxy, iso-butoxy, sec-butoxy, or t-butoxy group.

27. The process of claim 18, wherein the one or more alkene monomers comprise ethylene and propylene.

28. The process of claim 23, wherein both $R^{10}$ groups are the same or different group and are represented by the formula: $(XR'_n)^-$, wherein X is a Group 14, 15, 16 or 17 heteroatom having an atomic weight of 13 to 79 and R' is one of a hydrogen atom, halogen atom, a $C_1$-$C_{10}$ alkyl group, or a $C_6$-$C_{10}$ aryl group and n is 0, 1, 2 or 3, and the polymers produced using the transition metal complex have at least 20% higher Mw as compared to polymer produced by the same transition metal complex, except that both $R^{10}$ groups are hydrogen, combined with the same activator and polymerized under the same conditions with the same monomers.

29. The process of claim 28, wherein the one or more alkene monomers comprise ethylene and propylene.

30. The process of claim 18, wherein alkyl aluminum scavenger is present and the ratio of aluminum in alkyl aluminum scavenger to transition metal of the transition metal complex is 100:1 or less.

31. The transition metal complex of claim 1, wherein each $R^3$ is a cyclopropyl group; and each $R^{10}$ is an ethoxy group.

32. The process of claim 28, wherein the one or more alkene monomers consist essentially of ethylene and propylene.

33. The transition metal complex of claim 1, wherein each $R^9$ and $R^{11}$ is a t-butyl group, $R^{10}$ is —OR', wherein R' is one of a hydrogen atom, halogen atom, a $C_1$-$C_{10}$ alkyl group, or a $C_6$-$C_{10}$ aryl group, and $R^{14}$ is a substituted phenyl.

34. A bridged bis(4-phenyl-indenyl) transition metal complex wherein:
the first 4-phenyl ring is substituted at the 3' and 5' positions by radicals which are identical or different and selected from $C_2$-$C_{20}$ alkyl groups which are optionally halogenated, a $C_6$-$C_{10}$ aryl group which is optionally halogenated, a $C_2$-$C_{10}$ alkenyl group, a $C_7$-$C_{40}$ arylalkyl group, a $C_7$-$C_{20}$ alkylaryl group, a $C_8$-$C_{20}$ arylalkenyl group, and is also substituted at the 4' position with a group of the formula $(XR'_n)^-$, wherein X is a Group 14-17 heteroatom having an atomic weight of 13 to 79 and R' is one of a hydrogen atom, halogen atom, a $C_1$-$C_{10}$ alkyl group, or a $C_6$-$C_{10}$ aryl group and n is 0, 1, 2 or 3;
the second 4-phenyl ring is substituted at the 4' position with, a halogen atom, a $C_5$-$C_{10}$ alkyl group which is optionally halogenated, $C_3$ alkyl group which is optionally halogenated, a $C_2$-$C_{10}$ alkenyl group, a —NR'$_2$, —SR', —OR, —OSiR'$_3$ or —PR'$_2$ radical, wherein R' is as defined above; and
optionally, wherein one or more of the remaining positions on the phenyl and/or indenyl ring(s) of the transition metal complex are substituted.

35. A catalyst system comprising an activator and the transition metal complex of claim 8.

36. The catalyst system of claim 35, wherein the activator comprises an alumoxane.

37. The catalyst system of claim 35, wherein the activator comprises a non-coordinating anion.

38. A polymerization process comprising a) contacting one or more alkene monomers with a catalyst system comprising: i) an activator and ii) the transition metal complex of claim 8.

39. The process of claim 38, wherein the activator comprises an alumoxane.

40. The process of claim 38, wherein the activator comprises a non-coordinating anion.

41. The process of claim 38, wherein the one or more alkene monomers comprises propylene.

42. The process of claim 38, wherein the catalyst compound is supported.

43. The process of claim 38 further comprising obtaining polymer.

44. The process of claim 43, wherein the polymer comprises a propylene polymer having a melting point of 152.0° C. to about 162.0° C., an $M_w$ 60,000 to 1,400,000 g/mol; and an Mw/Mn of 1.5 to 3.5.

45. The transition metal complex of claim 1, wherein $R^{14}$ is —NR'$_2$, —SR', —OR', —OSiR'$_3$, —SiR'$_3$, or —PR'$_2$, wherein R' is one of a hydrogen atom, halogen atom, a $C_1$-$C_{10}$ alkyl group, or a $C_6$-$C_{10}$ aryl group.

46. The transition metal complex of claim 1, wherein $R^{10}$ is —NR'$_2$, —SR', —OR', —OSiR'$_3$, —SiR'$_3$, or —PR'$_2$, and $R^{14}$ is —NR'$_2$, —SR', —OR', —OSiR'$_3$, —SiR'$_3$, or —PR'$_2$, wherein R' is one of a hydrogen atom, halogen atom, a $C_1$-$C_{10}$ alkyl group, or a $C_6$-$C_{10}$ aryl group.

47. The process of claim 38, wherein the one or more alkene monomers comprise ethylene and propylene.

48. The process of claim 38, wherein alkyl aluminum scavenger is present and the ratio of aluminum in alkyl aluminum scavenger to transition metal of the transition metal complex is 100:1 or less.

49. The transition metal complex of claim 1, wherein $R^{10}$ is —NR'$_2$, —SR', —OSiR'$_3$, —SiR'$_3$, or —PR'$_2$, and $R^{14}$ is —NR'$_2$, —SR', —OSiR'$_3$, —SiR'$_3$, or —PR'$_2$, wherein R' is one of a hydrogen atom, halogen atom, a $C_1$-$C_{10}$ alkyl group, or a $C_6$-$C_{10}$ aryl group.

50. The transition metal complex of claim 1, wherein $R^{10}$ and $R^{14}$ are —OR'$_2$, wherein R' is one of a hydrogen atom, halogen atom, a $C_1$-$C_{10}$ alkyl group, or a $C_6$-$C_{10}$ aryl group.

51. A transition metal complex for use in alkene polymerization represented by the formula (II):

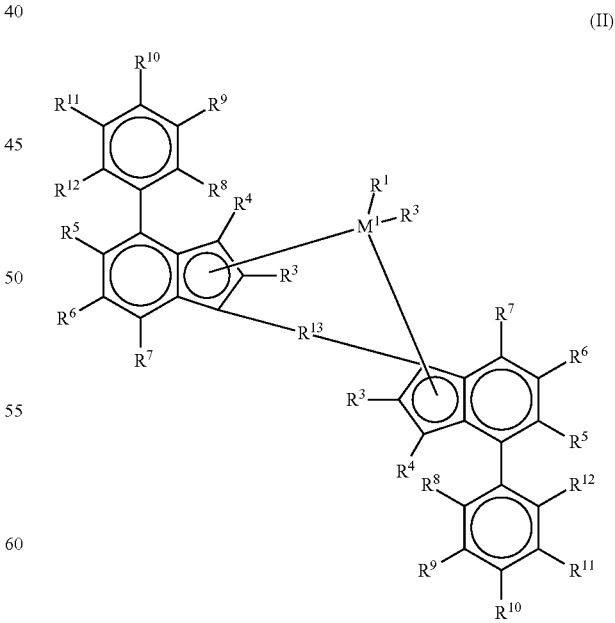

wherein $M^1$ is selected from the group consisting of titanium, zirconium, hafnium, vanadium, niobium, tantalum, chromium, molybdenum, and tungsten;

$R^1$ and $R^2$ are identical or different, and are each a hydrogen atom, a $C_1$-$C_{10}$ alkyl group, a $C_1$-$C_{10}$ alkoxy group, a $C_6$-$C_{10}$ aryl group, a $C_6$-$C_{10}$ aryloxy group, a $C_2$-$C_{10}$ alkenyl group, a $C_2$-$C_{40}$ alkenyl group, a $C_7$-$C_{40}$ arylalkyl group, a $C_7$-$C_{40}$ alkylaryl group, a $C_8$-$C_{40}$ arylalkenyl group, an OH group or a halogen atom, or a conjugated diene which is optionally substituted with one or more hydrocarbyl, tri(hydrocarbyl)silyl groups or tri(hydrocarbyl)silylhydrocarbyl groups, said diene having up to 30 atoms not counting hydrogen;

$R^3$ to $R^7$ are identical or different and are each a hydrogen atom, a halogen atom, a $C_1$-$C_{10}$ alkyl group which is optionally halogenated, a $C_6$-$C_{10}$ aryl group which is optionally halogenated, a $C_2$-$C_{10}$ alkenyl group, a $C_7$-$C_{40}$ arylalkyl group, a $C_7$-$C_{40}$ alkylaryl group, a $C_8$-$C_{40}$ arylalkenyl group, a —NR'$_2$, —SR', —OR, —OSiR'$_3$ or —PR'$_2$ radical, wherein R' is one of a hydrogen atom, halogen atom, a $C_1$-$C_{10}$ alkyl group, or a $C_6$-$C_{10}$ aryl group or two or more adjacent radicals $R^5$ to $R^7$ together with the atoms of the indenyl group connecting them form one or more rings;

$R^{13}$ is —B($R^{15}$)—, —Al($R^{15}$)—, —O—, —S—, —SO—, —SO2-, —N($R^{15}$)—, —CO—, —P($R^{15}$)—, or —P(O)($R^{15}$)—, an amidoborane radical or meets one of the following:

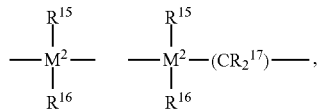

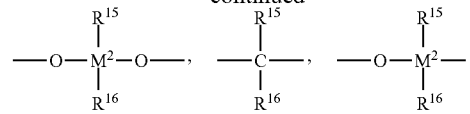

wherein $R^{15}$, $R^{16}$, $R^{17}$ are identical or different and are a hydrogen atom, a halogen atom, a $C_1$-$C_{20}$ alkyl group, a $C_1$-$C_{20}$ fluoroalkyl or silaalkyl group, a $C_6$-$C_{30}$ aryl group, a $C_6$-$C_{30}$ fluoroaryl group, a $C_1$-$C_{20}$ alkoxy group, a $C_2$-$C_{20}$ alkenyl group, a $C_7$-$C_{40}$ arylalkyl group, a $C_8$-$C_{40}$ arylalkenyl group, a $C_7$-$C_{40}$ alkylaryl group, or one $R^{15}$ and one $R^{16}$, together with the atoms in $R^{13}$ connecting them form a ring, $M^2$ is one or more of carbon, silicon, germanium or tin;

each $R^8$ and $R^{12}$ are identical or different and are each a hydrogen atom, a halogen atom, a $C_3$-$C_{10}$ alkyl group which is optionally halogenated, a $C_6$-$C_{10}$ aryl group which is optionally halogenated, a $C_2$-$C_{10}$ alkenyl group, a $C_7$-$C_{40}$ arylalkyl group, a $C_7$-$C_{40}$ alkylaryl group, a $C_8$-$C_{40}$ arylalkenyl group, a —NR'$_2$, —SR', —OR, —OSiR'$_3$ or —PR'$_2$ radical, wherein R' is one of a hydrogen atom, halogen atom, a $C_1$-$C_{10}$ alkyl group, or a $C_6$-$C_{10}$ aryl group;

each $R^9$ and $R^{11}$ are identical or different and are each a $C_2$-$C_{20}$ alkyl group; and each $R^{10}$ is individually —OR', wherein R' is a $C_1$-$C_{10}$ alkyl group or a $C_6$-$C_{10}$ aryl group.

* * * * *